US005549897A

United States Patent [19]

Barenkamp et al.

[11] Patent Number: 5,549,897

[45] Date of Patent: Aug. 27, 1996

[54] HIGH MOLECULAR WEIGHT SURFACE PROTEINS OF NON-TYPEABLE HAEMOPHILUS

[75] Inventors: Stephen J. Barenkamp, Webster Grove; Joseph W. St. Geme, III, St. Louis, both of Mo.

[73] Assignees: St. Louis University; Washington University, both of St. Louis, Mo.

[21] Appl. No.: 38,682

[22] Filed: Mar. 16, 1993

[30] Foreign Application Priority Data

Mar. 16, 1992 [GB] United Kingdom .................... 9205704

[51] Int. Cl.[6] .......................... A61K 39/102; A61K 38/16

[52] U.S. Cl. ....................... 424/256 N; 435/851; 530/350

[58] Field of Search ............................ 424/92, 88, 256.1; 435/851; 530/350

[56] References Cited

PUBLICATIONS

Barenkamp S. J., Pediatr Res 29(4 part 2) 1991 p. 167A Abstract #985.

Van Regenmortel, Immunology Today 10(8):266–272, 1989.

Dick et al, Contrib Microbiol. Immunol 10:48–114, 1989.

Roitt et al, eds *Immunology,* C. V. Mosby Co, St. Louis, Gowe–Medical Publishing, London, 1985 pp. 8.3–8.4.

Boslego et al Vaccine 9:154–162, 1991.

Pediatr. Infect. Dis. J., 9:333–339, 1990.

The Journal of Infectious Diseases, vol. 165(Suppl.), issued Aug. 1992, S. J. Barenkamp, "Outer Membrane Protein and Lipopolysaccharides of Nontypeable *Haemophilus influenzae*", pp. S181–S184, see entire document.

Infection and Immunity, vol. 56(1), issued Jan. 1988, E. J. Hansen, "Immune Enhancement of Pulmonary Clearance on Nontypable *Haemophilus influenzae,*" pp. 182–190, see entire document, especially Figs. 3 and 4.

Infection and Immunity, vol. 60(4), issued Apr. 1992, S. J. Barenkamp et al, "Cloning, Expression and DNA Sequence Analysis of Genes Encoding Nontypeable *Haemophilus influenzae* High –Molecular–Weight Surface–Exposed Proteins Related to Filamentous Hemagglutinin of *Bordetella pertussis,*" pp. 1302–1313, see entire document.

Infection and Immunity, vol. 52(2), issued May 1986, S. J. Barenkamp, "Protection by Serum Antibodies in Experimental Nontypable *Haemphilus influenzae* Otitis Media", pp. 572–578, see Figs. 1 and 2.

Proceedings of the National Academy of Sciences USA, vol. 80, issued Mar. 1983, R. A. Young et al, "Efficient Isolation of Genes by Using Antibody Probes, "pp. 1194–1198, see entire document.

Journal of Molecular Biology, vol. 157, issued 1982, J. Kyte et al, "A Simple Method for Displaying the Hydrophatic Character of a Protein", pp. 105–132, see entire document.

Proceedings of the National Academy of Sciences, vol. 78(6), issued Jun. 1981, T. P. Hopp et al, "Prediction of Protein Antigenic Determinants from Amino Acid Sequences", pp. 3824–3828, see entire document.

Infection and Immunity, vol. 45(3), issued Sep. 1984, R. Schneerson et al, "Serum Antibody Responses of Juvenile and Infant Rhesus Monkeys Injected with *Haemophilus influenzae* Type b and Pneumoccus Type 6A Capsular Polysaccharide–Protein Conjugates", pp. 582–591, see entire document.

*Primary Examiner*—James C. Housel
*Assistant Examiner*—Julie Krsek-Staples
*Attorney, Agent, or Firm*—Shoemaker and Mattare, Ltd.

[57] ABSTRACT

High molecular weight surface proteins of non-typeable *Haemophilus influenzae* which exhibit immunogenic properties and genes encoding the same are described. Specifically, genes coding for two immunodominant high molecular weight proteins, HMW1 and HMW2, have been cloned, expressed and sequenced, while genes coding for high molecular proteins HMW3 and HMW4 have been cloned, expressed and partially sequenced.

3 Claims, 68 Drawing Sheets

FIG. 1A. DNA SEQUENCE OF HIGH MOLECULAR WEIGHT PROTEIN I (HMW1)

```
  1  ACAGCGTTCT CTTAATACTA GTACAAACCC ACAATAAAAT ATGACAAACA
 51  ACAATTACAA CACCTTTTTT GCAGTCTATA TGCAAATATT TTAAAAAATA
101  GTATAAATCC GCCATATAAA ATGGTATAAT CTTTCATCTT TCATCTTTCA
151  TCTTTCATCT TTCATCTTTC ATCTTTCATC TTTCATCTTT CATCTTTCAT
201  CTTTCATCTT TCATCTTTCA TCTTTCATCT TTCATCTTTC ACATGCCCTG
251  ATGAACCGAG GGAAGGGAGG GAGGGGCAAG AATGAAGAGG GAGCTGAACG
301  AACGCAAATG ATAAAGTAAT TTAATTGTTC AACTAACCTT AGGAGAAAAT
351  ATGAACAAGC TATATCGTCT CAAATTCAGC AAACGCCTGA ATGCTTTGGT
401  TGCTGTGTCT GAATTGGCAC GGGGTTGTGA CCATTCCACA GAAAAAGGCA
451  GCGAAAAACC TGCTCGCATG AAAGTGCGTC ACTTAGCGTT AAAGCCACTT
501  TCCGCTATGT TACTATCTTT AGGTGTAACA TCTATTCCAC AATCTGTTTT
551  AGCAAGCGGC TTACAAGGAA TGGATGTAGT ACACGGCACA GCCACTATGC
601  AAGTAGATGG TAATAAAACC ATTATCCGCA ACAGTGTTGA CGATATCATT
651  AATTGGAAAC AATTTAACAT CGACCAAAAT GAAATGGTGC AGTTTTTACA
701  AGAAAACAAC AACTCCGCCG TATTCAACCG TGTTACATCT AACCAAATCT
```

FIG. 1B.

```
751   CCCAATTAAA AGGGATTTTA GATTCTAACG GACAAGTCTT TTTAATCAAC
801   CCAAATGGTA TCACAATAGG TAAAGACGCA ATTATTAACA CTAATGGCTT
851   TACGGCTTCT ACGCTAGACA TTTCTAACGA AAACATCAAG GCGCGTAATT
901   TCACCTTCGA GCAAACCAAA GATAAAGCGC TCGCTGAAAT TGTGAATCAC
951   GGTTTAATTA CTGTCGGTAA AGACGGCAGT GTAAATCTTA TTGGTGGCAA
1001  AGTGAAAAAC GAGGGTGTGA TTAGCGTAAA TGGTGGCAGC ATTTCTTTAC
1051  TCGCAGGGCA AAAAATCACC ATCAGCGATA TAATAAACCC AACCATTACT
1101  TACAGCATTG CCGCGCCTGA AAATGAAGCG GTCAATCTGG GCGATATTTT
1151  TGCCAAAGGC GGTAACATTA ATGTCCGTGC TGCCACTATT CGAAACCAAG
1201  GTAAACTTTC TGCTGATTCT GTAAGCAAAG ATAAAAGCGG CAATATTGTT
1251  CTTTCCGCCA AAGAGGGTGA AGCGGAAATT GGCGGTGTAA TTTCCGCTCA
1301  AAATCAGCAA GCTAAAGGCG GCAAGCTGAT GATTACAGGC GATAAAGTCA
1351  CATTAAAAAC AGGTGCAGTT ATCGACCTTT CAGGTAAAGA AGGGGGAGAA
1401  ACTTACCTTG GCGGTGACGA GCGCGGCGAA GGTAAAAAGG GCATTCAATT
1451  AGCAAAGAAA ACCTCTTTAG AAAAAGGCTC AACCATCAAT GTATCAGGCA
1501  AAGAAAAAGG CGGACGCGCT ATTGTGTGGG GCGATATTGC GTTAATTGAC
```

FIG. 1C.

| | | | | | |
|---|---|---|---|---|---|
| 1551 | GGCAATATTA | ACGCTCAAGG | TAGTGGTGAT | ATCGCTAAAA | CCGGTGGTTT |
| 1601 | TGTGGAGACG | TCGGGGCATG | ATTTATTCAT | CAAAGACAAT | GCAATTGTTG |
| 1651 | ACGCCAAAGA | GTGGTTGTTA | GACCCGGATA | ATGTATCTAT | TAATGCAGAA |
| 1701 | ACAGCAGGAC | GCAGCAATAC | TTCAGAAGAC | GATGAATACA | CGGGATCCGG |
| 1751 | GAATAGTGCC | AGCACCCCAA | AACGAAACAA | AGAAAAGACA | ACATTAACAA |
| 1801 | ACACAACTCT | TGAGAGTATA | CTAAAAAAAG | GTACCTTTGT | TAACATCACT |
| 1851 | GCTAATCAAC | GCATCTATGT | CAATAGCTCC | ATTAATTTAT | CCAATGGCAG |
| 1901 | CTTAACTCTT | TGGAGTGAGG | GTCGGAGCGG | TGGCGGCGTT | GAGATTAACA |
| 1951 | ACGATATTAC | CACCGGTGAT | GATACCAGAG | GTGCAAACTT | AACAATTTAC |
| 2001 | TCAGGCGGCT | GGGTTGATGT | TCATAAAAAT | ATCTCACTCG | GGGCGCAAGG |
| 2051 | TAACATAAAC | ATTACAGCTA | AACAAGATAT | CGCCTTTGAG | AAAGGAAGCA |
| 2101 | ACCAAGTCAT | TACAGGTCAA | GGGACTATTA | CCTCAGGCAA | TCAAAAAGGT |
| 2151 | TTTAGATTTA | ATAATGTCTC | TCTAAACGGC | ACTGGCAGCG | GACTGCAATT |
| 2201 | CACCACTAAA | AGAACCAATA | AATACGCTAT | CACAAATAAA | TTTGAAGGGA |
| 2251 | CTTTAAATAT | TTCAGGGAAA | GTGAACATCT | CAATGGTTTT | ACCTAAAAAT |
| 2301 | GAAAGTGGAT | ATGATAAATT | CAAAGGACGC | ACTTACTGGA | ATTTAACCTC |

FIG. 1D.

| | | | | | |
|---|---|---|---|---|---|
| 2351 | CTTAAATGTT | TCCGAGAGTG | GCGAGTTTAA | CCTCACTATT | GACTCCAGAG |
| 2401 | GAAGCGATAG | TGCAGGCACA | CTTACCCAGC | CTTATAATTT | AAACGGTATA |
| 2451 | TCATTCAACA | AAGACACTAC | CTTTAATGTT | GAACGAAATG | CAAGAGTCAA |
| 2501 | CTTTGACATC | AAGGCACCAA | TAGGGATAAA | TAAGTATTCT | AGTTTGAATT |
| 2551 | ACGCATCATT | TAATGGAAAC | ATTTCAGTTT | CGGGAGGGGG | GAGTGTTGAT |
| 2601 | TTCACACTTC | TCGCCTCATC | CTCTAACGTC | CAAACCCCCG | GTGTAGTTAT |
| 2651 | AAATTCTAAA | TACTTTAATG | TTTCAACAGG | GTCAAGTTTA | AGATTTAAAA |
| 2701 | CTTCAGGCTC | AACAAAAACT | GGCTTCTCAA | TAGAGAAAGA | TTTAACTTTA |
| 2751 | AATGCCACCG | GAGGCAACAT | AACACTTTTG | CAAGTTGAAG | GCACCGATGG |
| 2801 | AATGATTGGT | AAAGGCATTG | TAGCCAAAAA | AAACATAACC | TTTGAAGGAG |
| 2851 | GTAACATCAC | CTTTGGCTCC | AGGAAAGCCG | TAACAGAAAT | CGAAGGCAAT |
| 2901 | GTTACTATCA | ATAACAACGC | TAACGTCACT | CTTATCGGTT | CGGATTTTGA |
| 2951 | CAACCATCAA | AAACCTTTAA | CTATTAAAAA | AGATGTCATC | ATTAATAGCG |
| 3001 | GCAACCTTAC | CGCTGGAGGC | AATATTGTCA | ATATAGCCGG | AAATCTTACC |
| 3051 | GTTGAAAGTA | ACGCTAATTT | CAAAGCTATC | ACAAATTTCA | CTTTTAATGT |
| 3101 | AGGCGGCTTG | TTTGACAACA | AAGGCAATTC | AAATATTTCC | ATTGCCAAAG |
| 3151 | GAGGGGCTCG | CTTTAAAGAC | ATTGATAATT | CCAAGAATTT | AAGCATCACC |

FIG. 1E.

3201 ACCAACTCCA GCTCCACTTA CCGCACTATT ATAAGCGGCA ATATAACCAA
3251 TAAAAACGGT GATTTAAATA TTACGAACGA AGGTAGTGAT ACTGAAATGC
3301 AAATTGGCGG CGATGTCTCG CAAAAAGAAG GTAATCTCAC GATTTCTTCT
3351 GACAAAATCA ATATTACCAA ACAGATAACA ATCAAGGCAG GTGTTGATGG
3401 GGAGAATTCC GATTCAGACG CGACAAACAA TGCCAATCTA ACCATTAAAA
3451 CCAAAGAATT GAAATTAACG CAAGACCTAA ATATTTCAGG TTTCAATAAA
3501 GCAGAGATTA CAGCTAAAGA TGGTAGTGAT TTAACTATTG GTAACACCAA
3551 TAGTGCTGAT GGTACTAATG CCAAAAAAGT AACCTTTAAC CAGGTTAAAG
3601 ATTCAAAAAT CTCTGCTGAC GGTCACAAGG TGACACTACA CAGCAAAGTG
3651 GAAACATCCG GTAGTAATAA CAACACTGAA GATAGCAGTG ACAATAATGC
3701 CGGCTTAACT ATCGATGCAA AAAATGTAAC AGTAAACAAC AATATTACTT
3751 CTCACAAAGC AGTGAGCATC TCTGCGACAA GTGGAGAAAT TACCACTAAA
3801 ACAGGTACAA CCATTAACGC AACCACTGGT AACGTGGAGA TAACCGCTCA
3851 AACAGGTAGT ATCCTAGGTG GAATTGAGTC CAGCTCTGGC TCTGTAACAC
3901 TTACTGCAAC CGAGGGCGCT CTTGCTGTAA GCAATATTTC GGGCAACACC
3951 GTTACTGTTA CTGCAAATAG CGGTGCATTA ACCACTTTGG CAGGCTCTAC

FIG. 1F.

```
4001  AATTAAAGGA ACCGAGAGTG TAACCACTTC AAGTCAATCA GGCGATATCG
4051  GCGGTACGAT TTCTGGTGGC ACAGTAGAGG TTAAAGCAAC CGAAAGTTTA
4101  ACCACTCAAT CCAATTCAAA AATTAAAGCA ACAACAGGCG AGGCTAACGT
4151  AACAAGTGCA ACAGGTACAA TTGGTGGTAC GATTTCCGGT AATACGGTAA
4201  ATGTTACGGC AAACGCTGGC GATTTAACAG TTGGGAATGG CGCAGAAATT
4251  AATGCGACAG AAGGAGCTGC AACCTTAACT ACATCATCGG GCAAATTAAC
4301  TACCGAAGCT AGTTCACACA TTACTTCAGC CAAGGGTCAG GTAAATCTTT
4351  CAGCTCAGGA TGGTAGCGTT GCAGGAAGTA TTAATGCCGC CAATGTGACA
4401  CTAAATACTA CAGGCACTTT AACTACCGTG AAGGGTTCAA ACATTAATGC
4451  AACCAGCGGT ACCTTGGTTA TTAACGCAAA AGACGCTGAG CTAAATGGCG
4501  CAGCATTGGG TAACCACACA GTGGTAAATG CAACCAACGC AAATGGCTCC
4551  GGCAGCGTAA TCGCGACAAC CTCAAGCAGA GTGAACATCA CTGGGGATTT
4601  AATCACAATA AATGGATTAA ATATCATTTC AAAAAACGGT ATAAACACCG
4651  TACTGTTAAA AGGCGTTAAA ATTGATGTGA AATACATTCA ACCGGGTATA
4701  GCAAGCGTAG ATGAAGTAAT TGAAGCGAAA CGCATCCTTG AGAAGGTAAA
4751  AGATTTATCT GATGAAGAAA GAGAAGCGTT AGCTAAACTT GGAGTAAGTG
4801  CTGTACGTTT TATTGAGCCA AATAATACAA TTACAGTCGA TACACAAAAT
```

FIG. 1G.

```
4851  GAATTTGCAA CCAGACCATT AAGTCGAATA GTGATTTCTG AAGGCAGGGC
4901  GTGTTTCTCA AACAGTGATG GCGCGACGGT GTGCGTTAAT ATCGCTGATA
4951  ACGGGCGGTA GCGGTCAGTA ATTGACAAGG TAGATTTCAT CCTGCAATGA
5001  AGTCATTTTA TTTTCGTATT ATTTACTGTG TGGGTTAAAG TTCAGTACGG
5051  GCTTTACCCA TCTTGTAAAA AATTACGGAG AATACAATAA AGTATTTTTA
5101  ACAGGTTATT ATTATG
```

FIG. 2A. AMINO ACID SEQUENCE OF HIGH MOLECULAR WEIGHT PROTEIN I

```
  1 MNKIYRLKFS KRLNALVAVS ELARGCDHST EKGSEKPARM KVRHLALKPL
 51 SAMLLSLGVT SIPQSVLASG LQGMDVVHGT ATMQVDGNKT IIRNSVDAII
101 NWKQFNIDQN EMVQFLQENN NSAVFNRVTS NQISQLKGIL DSNGQVFLIN
151 PNGITIGKDA IINTNGFTAS TLDISNENIK ARNFTFEQTK DKALAEIVNH
201 GLITVGKDGS VNLIGGKVKN EGVISVNGGS ISLLAGQKIT ISDIINPTIT
251 YSIAAPENEA VNLGDIFAKG GNINVRAATI RNQGKLSADS VSKDKSGNIV
301 LSAKEGEAEI GGVISAQNQQ AKGGKLMITG DKVTLKTGAV IDLSGKEGGE
351 TYLGGDERGE GKNGIQLAKK TSLEKGSTIN VSGKEKGGRA IVWGDIALID
401 GNINAQGSGD IAKTGGFVET SGHDLFIKDN AIVDAKEWLL DFDNVSINAE
451 TAGRSNTSED DEYTGSGNSA STPKRNKEKT TLTNTTLESI LKKGTFVNIT
501 ANQRIYVNSS INLSNGSLTL WSEGRSGGGV EINNDITTGD DTRGANLTIY
551 SGGWVDVHKN ISLGAQGNIN ITAKQDIAFE KGSNQVITGQ GTITSGNQKG
601 FRFNNVSLNG TGSGLQFTTK RTNKYAITNK FEGTLNISGK VNISMVLPKN
651 ESGYDKFKGR TYWNLTSLNV SESGEFNLTI DSRGSDSAGT LTQPYNLNGI
701 SFNKDTTFNV ERNARVNFDI KAPIGINKYS SLNYASFNGN ISVSGGGSVD
```

FIG.2B.

```
751   FTLLASSSNV QTPGVVINSK YFNVSTGSSL RFKTSGSTKT GFSIEKDLTL
801   NATGGNITLL QVEGTDGMIG KGIVAKKNIT FEGGNITFGS RKAVTEIEGN
851   VTINNNANVT LIGSDFDNHQ KPLTIKKDVI INSGNLTAGG NIVNIAGNLT
901   VESNANFKAI TNFTFNVGGL FDNKGNSNIS IAKGGARFKD IDNSKNLSIT
951   TNSSSTYRTI ISGNITNKNG DLNITNEGSD TEMQIGGDVS QKEGNLTISS
1001  DKINITKQIT IKAGVDGENS DSDATNNANL TIKTKELKLT QDLNISGFNK
1051  AEITAKDGSD LTIGNTNSAD GTNAKKVTFN QVKDSKISAD GHKVTLHSKV
1101  ETSGSNNNTE DSSDNNAGLT IDAKNVTVNN NITSHKAVSI SATSGEITTK
1151  TGTTINATTG NVEITAQTGS ILGGIESSSG SVTLTATEGA LAVSNISGNT
1201  VTVTANSGAL TTLAGSTIKG TESVTTSSQS GDIGGTISGG TVEVKATESL
1251  TTQSNSKIKA TTGEANVTSA TGTIGGTISG NTVNVTANAG DLTVGNGAEI
1301  NATEGAATLT TSSGKLTTEA SSHITSAKGQ VNLSAQDGSV AGSINAANVT
1351  LNTTGTLTTV KGSNINATSG TLVINAKDAE LNGAALGNHT VVNATNANGS
1401  GSVIATTSSR VNITGDLITI NGLNIISKNG INTVLLKGVK IDVKYIQPGI
1451  ASVDEVIEAK RILEKVKDLS DEEREALAKL GVSAVRFIEP NNTITVDTQN
1501  EFATRPLSRI VISEGRACFS NSDGATVCVN IADNGR
```

FIG. 3A. AMINO ACID SEQUENCE OF HIGH MOLECULAR WEIGHT PROTEIN II (HMW2)

| | | | | | |
|---|---|---|---|---|---|
| 1 | TAAATATACA | AGATAATAAA | AATAAATCAA | GATTTTTGTG | ATGACAAACA |
| 51 | ACAATTACAA | CACCTTTTTT | GCAGTCTATA | TGCAAATATT | TTAAAAAAAT |
| 101 | AGTATAAATC | CGCCATATAA | AATGGTATAA | TCTTTCATCT | TTCATCTTTA |
| 151 | ATCTTTCATC | TTTCATCTTT | CATCTTTCAT | CTTTCATCTT | TCATCTTTCA |
| 201 | TCTTTCATCT | TTCATCTTTC | ATCTTTCATC | TTTCATCTTT | CACATGAAAT |
| 251 | GATGAACCGA | GGGAAGGGAG | GGAGGGGCAA | GAATGAAGAG | GGAGCTGAAC |
| 301 | GAACGCAAAT | GATAAAGTAA | TTTAATTGTT | CAACTAACCT | TAGGAGAAAA |
| 351 | TATGAACAAG | ATATATCGTC | TCAAATTCAG | CAAACGCCTG | AATGCTTTGG |
| 401 | TTGCTGTGTC | TGAATTGGCA | CGGGGTTGTG | ACCATTCCAC | AGAAAAAGGC |
| 451 | TTCCGCTATG | TTACTATCTT | TAGGTGTAAC | CACTTAGCGT | TAAAGCCACT |
| 501 | TTCCGCTATG | TTACTATCTT | TAGGTGTAAC | ATCTATTCCA | CAATCTGTTT |
| 551 | TAGCAAGCGG | CTTACAAGGA | ATGGATGTAG | TACACGGCAC | AGCCACTATG |
| 601 | CAAGTAGATG | GTAATAAAAC | CATTATCCGC | AACAGTGTTG | ACGCTATCAT |
| 651 | TAATTGGAAA | CAATTTAACA | TCGACCAAAA | TGAAATGGTG | CAGTTTTTAC |
| 701 | AAGAAAACAA | CAACTCCGCC | GTATTCAACC | GTGTTACATC | TAACCAAATC |

FIG. 3B.

| | | | | | |
|---|---|---|---|---|---|
| 751 | TCCCAATTAA | AAGGGATTTT | AGATTCTAAC | GGACAAGTCT | TTTTAATCAA |
| 801 | CCCAAATGGT | ATCACAATAG | GTAAAGACGC | AATTATTAAC | ACTAATGGCT |
| 851 | TTACGGCTTC | TACGCTAGAC | ATTTCTAACG | AAAACATCAA | GGCGCGTAAT |
| 901 | TTCACCTTCG | AGCAAACCAA | AGATAAAGCG | CTCGCTGAAA | TTGTGAATCA |
| 951 | CGGTTTAATT | ACTGTCGGTA | AAGACGGCAG | TGTAAATCTT | ATTGGTGGCA |
| 1001 | AAGTGAAAAA | CGAGGGTGTG | ATTAGCGTAA | ATGGTGGCAG | CATTTCTTTA |
| 1051 | CTCGCAGGGC | AAAAAATCAC | CATCAGCGAT | ATAATAAACC | CAACCATTAC |
| 1101 | TTACAGCATT | GCCGCGCCTG | AAAATGAAGC | GGTCAATCTG | GGCGATATTT |
| 1151 | TTGCCAAAGG | CGGTAACATT | AATGTCCGTG | CTGCCACTAT | TCGAAACCAA |
| 1201 | GGTAAACTTT | CTGCTGATTC | TGTAAGCAAA | GATAAAAGCG | GCAATATTGT |
| 1251 | TCTTTCCGCC | AAAGAGGGTG | AAGCGGAAAT | TGGCGGTGTA | ATTTCCGCTC |
| 1301 | AAAATCAGCA | AGCTAAAGGC | GGCAAGCTGA | TGATTACAGG | CGATAAAGTC |
| 1351 | ACATTAAAAA | CAGGTGCAGT | TATCGACCTT | TCAGGTAAAG | AAGGGGGAGA |
| 1401 | AACTTACCTT | GGCGGTGACG | AGCGCGGCGA | AGGTAAAAAC | GGCATTCAAT |
| 1451 | TAGCAAAGAA | AACCTCTTTA | GAAAAAGGCT | CAACCATCAA | TGTATCAGGC |
| 1501 | AAAGAAAAAG | GCGGACGCGC | TATTGTGTGG | GGCGATATTG | CGTTAATTGA |

FIG. 3C.

```
1551  CGGCAATATT AACGCTCAAG GTAGTGGTGA TATCGCTAAA ACCGGTGGTT
1601  TTGTGGAGAC ATCGGGGCAT TATTTATCCA TTGACAGCAA TGCAATTGTT
1651  AAAACAAAAG AGTGGTTGCT AGACCCTGAT GATGTAACAA TTGAAGCCGA
1701  AGACCCCCTT CGCAATAATA CCGGTATAAA TGATGAATTC CCAACAGGCA
1751  CCGGTGAAGC AAGCGACCCT AAAAAAAATA GCGAACTCAA AACAACGCTA
1801  ACCAATACAA CTATTTCAAATTATCTGAAA AACGCCTGGA CAATGAATAT
1851  AACGGCATCA AGAAAACTTA CCGTTAATAG CTCAATCAAC ATCGGAAGCA
1901  ACTCCCACTT AATTCTCCAT AGTAAAGGTC AGCGTGGCGG AGGCGTTCAG
1951  ATTGATGGAG ATATTACTTC TAAAGGCGGA AATTTAACCA TTTATTCTGG
2001  CGGATGGGTT GATGTTCATA AAAATATTAC GCTTGATCAG GGTTTTTTAA
2051  ATATTACCGC CGCTTCCGTA GCTTTTGAAG GTGGAAATAA CAAAGCACGC
2101  GACGCGGCAA ATGCTAAAAT TGTCGCCCAG GGCACTGTAA CCATTACAGG
2151  AGAGGGAAAA GATTTCAGGG CTAACAACGT ATCTTTAAAC GGAACGGGTA
2201  AAGGTCTGAA TATCATTTCA TCAGTGAATA ATTTAACCCA CAATCTTAGT
2251  GGCACAATTA ACATATCTGG GAATATAACA ATTAACCAAA CTACGAGAAA
2301  GAACACCTCG TATTGGCAAA CCAGCCATGA TTCGCACTGG AACGTCAGTG
2351  CTCTTAATCT AGAGACAGGC GCAAATTTTA CCTTTATTAA ATACATTTCA
```

FIG. 3D.

| | | | | | |
|---|---|---|---|---|---|
| 2401 | AGCAATAGCA | AAGGCTTAAC | AACACAGTAT | AGAAGCTCTG | CAGGGGTGAA |
| 2451 | TTTTAACGGC | GTAAATGGCA | ACATGTCATT | CAATCTCAAA | GAAGGAGCGA |
| 2501 | AAGTTAATTT | CAAATTAAAA | CCAAACGAGA | ACATGAACAC | AAGCAAACCT |
| 2551 | TTACCAATTC | GGTTTTTAGC | CAATATCACA | GCCACTGGTG | GGGGCTCTGT |
| 2601 | TTTTTTTGAT | ATATATGCCA | ACCATTCTGG | CAGAGGGGCT | GAGTTAAAAA |
| 2651 | TGAGTGAAAT | TAATATCTCT | AACGGCGCTA | ATTTTACCTT | AAATTCCCAT |
| 2701 | GTTCGCGGCG | ATGACGCTTT | TAAAATCAAC | AAAGACTTAA | CCATAAATGC |
| 2751 | AACCAATTCA | AATTTCAGCC | TCAGACAGAC | GAAAGATGAT | TTTTATGACG |
| 2801 | GGTACGCACG | CAATGCCATC | AATTCAACCT | ACAACATATC | CATTCTGGGC |
| 2851 | GGTAATGTCA | CCCTTGGTGG | ACAAAACTCA | AGCAGCAGCA | TTACGGGGAA |
| 2901 | TATTACTATC | GAGAAAGCAG | CAAATGTTAC | GCTAGAAGCC | AATAACGCCC |
| 2951 | CTAATCAGCA | AAACATAAGG | GATAGAGTTA | TAAAACTTGG | CAGCTTGCTC |
| 3001 | GTTAATGGGA | GTTTAAGTTT | AACTGGCGAA | AATGCAGATA | TTAAAGGCAA |
| 3051 | TCTCACTATT | TCAGAAAGCG | CCACTTTTAA | AGGAAAGACT | AGAGATACCC |
| 3101 | TAAATATCAC | CGGCAATTTT | ACCAATAATG | GCACTGCCGA | AATTAATATA |
| 3151 | ACACAAGGAG | TGGTAAAACT | TGGCAATGTT | ACCAATGATG | GTGATTTAAA |

FIG. 3E.

| | | | | | |
|---|---|---|---|---|---|
| 3201 | CATTACCACT | CACGCTAAAC | GCAACCAAAG | AAGCATCATC | GGCGGAGATA |
| 3251 | TAATCAACAA | AAAAGGAAGC | TTAAATATTA | CAGACAGTAA | TAATGATGCT |
| 3301 | GAAATCCAAA | TTGGCGGCAA | TATCTCGCAA | AAAGAAGGCA | ACCTCACGAT |
| 3351 | TTCTTCCGAT | AAAATTAATA | TCACCAAACA | GATAACAATC | AAAAAGGGTA |
| 3401 | TTGATGGAGA | GGACTCTAGT | TCAGATGCGA | CAAGTAATGC | CAACCTAACT |
| 3451 | ATTAAAACCA | AAGAATTGAA | ATTGACAGAA | GACCTAAGTA | TTTCAGGTTT |
| 3501 | CAATAAAGCA | GAGATTACAG | CCAAAGATGG | TAGAGATTTA | ACTATTGGCA |
| 3551 | ACAGTAATGA | CGGTAACAGC | GGTGCCGAAG | CCAAAACAGT | AACTTTTAAC |
| 3601 | AATGTTAAAG | ATTCAAAAAT | CTCTGCTGAC | GGTCACAATG | TGACACTAAA |
| 3651 | TAGCAAAGTG | AAAACATCTA | GCAGCAATGG | CGGACGTGAA | AGCAATAGCG |
| 3701 | ACAACGATAC | CGGCTTAACT | ATTACTGCAA | AAAATGTAGA | AGTAAACAAA |
| 3751 | GATATTACTT | CTCTCAAAAC | AGTAAATATC | ACCGCGTCGG | AAAAGGTTAC |
| 3801 | CACCACAGCA | GGCTCGACCA | TTAACGCAAC | AAATGGCAAA | GCAAGTATTA |
| 3851 | CAACCAAAAC | AGGTGATATC | AGCGGTACGA | TTTCCGGTAA | CACGGTAAGT |
| 3901 | GTTAGCGCGA | CTGGTGATTT | AACCACTAAA | TCCGGCTCAA | AAATTGAAGC |
| 3951 | GAAATCGGGT | GAGGCTAATG | TAACAAGTGC | AACAGGTACA | ATTGGCGGTA |

FIG. 3F.

```
4001  CAATTTCCGG TAATACGGTA AATGTTACGG CAAACGCTGG CGATTTAACA
4051  GTTGGGAATG GCGCAGAAAT TAATGCGACA GAAGGAGCTG CAACCTTAAC
4101  CGCAACAGGG AATACCTTGA CTACTGAAGC CGGTTCTAGC ATCACTTCAA
4151  CTAAGGGTCA GGTAGACCTC TTGGCTCAGA ATGGTAGCAT CGCAGGAAGC
4201  ATTAATGCTG CTAATGTGAC ATTAAATACT ACAGGCACCT TAACCACCGT
4251  GGCAGGCTCG GATATTAAAG CAACCAGCGG CACCTTGGTT ATTAACGCAA
4301  AAGATGCTAA GCTAAATGGT GATGCATCAG GTGATAGTAC AGAAGTGAAT
4351  GCAGTCAACG CAAGCGGCTC TGGTAGTGTG ACTGCGGCAA CCTCAAGCAG
4401  TGTGAATATC ACTGGGGATT TAAACACAGT AAATGGGTTA AATATCATTT
4451  CGAAAGATGG TAGAAACACT GTGCGCTTAA GAGGCAAGGA AATTGAGGTG
4501  AAATATATCC AGCCAGGTGT AGCAAGTGTA GAAGAAGTAA TTGAAGCGAA
4551  ACGCGTCCTT GAAAAAGTAA AAGATTTATC TGATGAAGAA AGAGAAACAT
4601  TAGCTAAACT TGGTGTAAGT GCTGTACGTT TTGTTGAGCC AAATAATACA
4651  ATTACAGTCA ATACACAAAA TGAATTTACA ACCAGACCGT CAAGTCAAGT
4701  GATAATTTCT GAAGGTAAGG CGTGTTTCTC AAGTGGTAAT GGCGCACGAG
4751  TATGTACCAA TGTTGCTGAC GATGGACAGC CGTAGTCAGT AATTGACAAG
4801  GTAGATTTCA TCCTGCAATG AAGTCATTTT ATTTTCGTAT TATTTACTGT
```

FIG. 3G.

4851 GTGGGTTAAA GTTCAGTACG GGCTTTACCC ATCTTGTAAA AAATTACGGA
4901 GAATACAATA AAGTATTTTT AACAGGTTAT TATTATG

FIG. 4A. AMINO ACID SEQUENCE OF HIGH MOLECULAR WEIGHT PROTEIN 2

```
  1 MNKIYRLKFS KRLNALVAVS ELARGCDHST EKGSEKPARM KVRHLALKPL
 51 SAMLLSLGVT SIPQSVLASG LQGMDVVHGT ATMQVDGNKT IIRNSVDAII
101 NWKQFNIDQN EMVQFLQENN NSAVFNRVTS NQISQLKGIL DSNGQVFLIN
151 PNGITIGKDA IINTNGFTAS TLDISNENIK ARNFTFEQTK DKALAEIVNH
201 GLITVGKDGS VNLIGGKVKN EGVISVNGGS ISLLAGQKIT ISDIINPTIT
251 YSIAAPENEA VNLGDIFAKG GNINVRAATI RNQGKLSADS VSKDKSGNIV
301 LSAKEGEAEI GGVISAQNQQ AKGGKLMITG DKVTLKTGAV IDLSGKEGGE
351 TYLGGDERGE GKNGIQLAKK TSLEKGSTIN VSGKEKGGRA IVWGDIALID
401 GNINAQGSGD IAKTGGFVET SGHDLFIKDN AIVDAKEWLL DFDNVSINAE
451 DPLRNNTGIN DEFPTGTGEA SDPKKNSELK TTLTNTTISN YLKNAWTMNI
501 TASRKLTVNS SINIGSNSHL ILHSKGQRGG GVQIDGDITS KGGNLTIYSG
551 GWVDVHKNIT LDQGFLNITA ASVAFEGGNN KARDAANAKI VAQGTVTITG
601 EGKDFRANNV SLNGTGKGLN IISSVNNLTH NLSGTINISG NITINQTTRK
651 NTSYWQTSHD SHWNVSALNL ETGANFTFIK YISSNSKGLT TQYRSSAGVN
701 FNGVNGNMSF NLKEGAKVNF KLKPNENMNT SKPLPIRFLA NITATGGGSV
```

FIG. 4B.

```
751   FFDIYANHSG RGAELKMSEI NISNGANFTL NSHVRGDDAF KINKDLTINA
801   TNSNFSLRQT KDDFYDGYAR NAINSTYNIS ILGGNVTLGG QNSSSSITGN
851   ITIEKAANVT LEANNAPNQQ NIRDRVIKLG SLLVNGSLSL TGENADIKGN
901   LTISESATFK GKTRDTLNIT GNFTNNGTAE INITQGVVKL GNVTNDGDLN
951   ITTHAKRNQR SIIGGDIINK KGSLNITDSN NDAEIQIGGN ISQKEGNLTI
1001  SSDKINITKQ ITIKKGIDGE DSSSDATSNA NLTIKTKELK LTEDLSISGF
1051  NKAEITAKDG RDLTIGNSND GNSGAEAKTV TFNNVKDSKI SADGHNVTLN
1101  SKVKTSSSNG GRESNSDNDT GLTITAKNVE VNKDITSLKT VNITASEKVT
1151  TTAGSTINAT NGKASITTKT GDISGTISGN TVSVSATVDL TTKSGSKIEA
1201  KSGEANVTSA TGTIGGTISG NTVNVTANAG DLTVGNGAEI NATEGAATLT
1251  ATGNTLTTEA GSSITSTKGQ VDLLAQNGSI AGSINAANVT LNTTGTLTTV
1301  AGSDIKATSG TLVINAKDAK LNGDASGDST EVNAVNASGS GSVTAATSSS
1351  VNITGDLNTV NGLNIISKDG RNTVRLRGKE IEVKYIQPGV ASVEEVIEAK
1401  RVLEKVKDLS DEERETLAKL GVSAVRFVEP NNTITVNTQN EFTTRPSSQV
1451  IISEGKACFS SGNGARVCTN VADDGQP
```

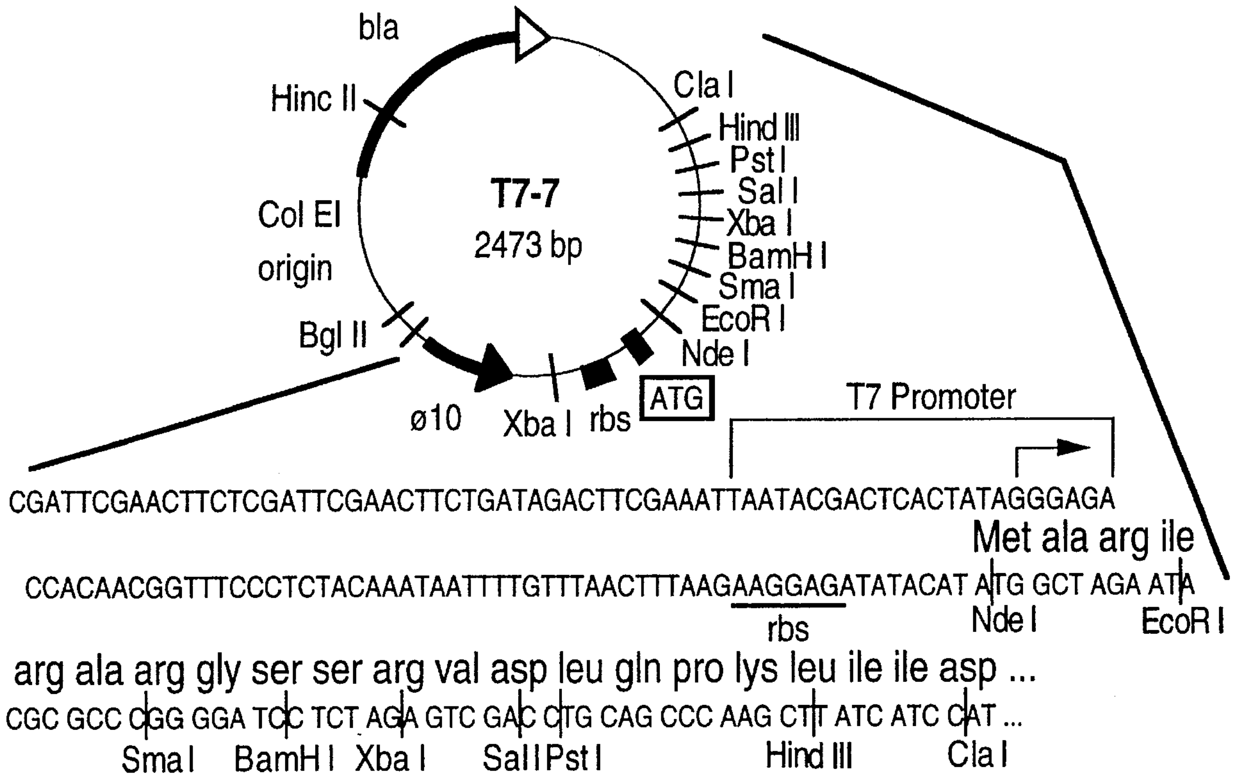

FIG. 5B.

(A) Partial restriction maps of representative HMW1 and HMW2 recombinant phage and of HMW1 plasmid subclones. The shaded boxes indicate the locations of the structural genes. In the recombinant phage, transcription proceeds from left to right for the HMW1 gene and from right to left for the HMW2 gene. The methods used for construction of the plasmids shown are described in the text. (B) Restriction map of the T7 expression vector pT7-7. This vector contains the T7 RNA polymerase promoter ϕ10, a ribosome - binding site (rbs), and the translational start site for the T7 gene 10 protein upstream from a multiple cloning site (37).

FIG. 6A.

| | | | | | |
|---|---|---|---|---|---|
| 1 | ACAGCGTTCT | CTTAATACTA | GTACAAACCC | ACAATAAAAT | ATGACAAACA |
| 51 | ACAATTACAA | CACCTTTTTT | GCAGTCTATA | TGCAAATATT | TTAAAAAATA |
| 101 | GTATAAATCC | GCCATATAAA | ATGGTATAAT | CTTTCATCTT | TCATCTTTCA |
| 151 | TCTTTCATCT | TTCATCTTTC | ATCTTTCATC | TTTCATCTTT | CATCTTTCAT |
| 201 | CTTTCATCTT | TCATCTTTCA | TCTTTCATCT | TTCATCTTTC | ACATGAAATG |
| 251 | ATGAACCGAG | GGAAGGGAGG | GAGGGGCAAG | AATGAAGAGG | GAGCTGAACG |
| 301 | AACGCAAATG | ATAAAGTAAT | TTAATTGTTC | AACTAACCTT | AGGAGAAAAT |
| 351 | ATGAACAAGA | TATATCGTCT | CAAATTCAGC | AAACGCCTGA | ATGCTTTGGT |
| 401 | TGCTGTGTCT | GAATTGGCAC | GGGGTTGTGA | CCATTCCACA | GAAAAAGGCA |
| 451 | GCGAAAAACC | TGCTCGCATG | AAAGTGCGTC | ACTTAGCGTT | AAAGCCACTT |
| 501 | TCCGCTATGT | TACTATCTTT | AGGTGTAACA | TCTATTCCAC | AATCTGTTTT |
| 551 | AGCAAGCGGC | TTACAAGGAA | TGGATGTAGT | ACACGGCACA | GCCACTATGC |
| 601 | AAGTAGATGG | TAATAAAACC | ATTATCCGCA | ACAGTGTTGA | CGCTATCATT |
| 651 | AATTGGAAAC | AATTTAACAT | CGACCAAAAT | GAAATGGTGC | AGTTTTTACA |
| 701 | AGAAAACAAC | AACTCCGCCG | TATTCAACCG | TGTTACATCT | AACCAAATCT |
| 751 | CCCAATTAAA | AGGGATTTTA | GATTCTAACG | GACAAGTCTT | TTTAATCAAC |

FIG. 6B.

| | | | | | |
|---|---|---|---|---|---|
| 801 | CCAAATGGTA | TCACAATAGG | TAAAGACGCA | ATTATTAACA | CTAATGGCTT |
| 851 | TACGGCTTCT | ACGCTAGACA | TTTCTAACGA | AAACATCAAG | GCGCGTAATT |
| 901 | TCACCTTCGA | GCAAACCAAA | GATAAAGCGC | TCGCTGAAAT | TGTGAATCAC |
| 951 | GGTTTAATTA | CTGTCGGTAA | AGACGGCAGT | GTAAATCTTA | TTGGTGGCAA |
| 1001 | AGTGAAAAAC | GAGGGTGTGA | TTAGCGTAAA | TGGTGGCAGC | ATTTCTTTAC |
| 1051 | TCGCAGGGCA | AAAAATCACC | ATCAGCGATA | TAATAAACCC | AACCATTACT |
| 1101 | TACAGCATTG | CCGCGCCTGA | AAATGAAGCG | GTCAATCTGG | GCGATATTTT |
| 1151 | TGCCAAAGGC | GGTAACATTA | ATGTCCGTGC | TGCCACTATT | CGAAACCAAG |
| 1251 | CTTTCCGCCA | AAGAGGGTGA | AGCGGAAATT | GGCGGTGTAA | TTTCCGCTCA |
| 1301 | AAATCAGCAA | GCTAAAGGCG | GCAAGCTGAT | GATTACAGGC | GATAAAGTCA |
| 1351 | CATTAAAAAC | AGGTGCAGTT | ATCGACCTTT | CAGGTAAAGA | AGGGGGAGAA |
| 1401 | ACTTACCTTG | GCGGTGACGA | GCGCGGCGAA | GGTAAAAACG | GCATTCAATT |
| 1451 | AGCAAAGAAA | ACCTCTTTAG | AAAAAGGCTC | AACCATCAAT | GTATCAGGCA |
| 1501 | AAGAAAAAGG | CGGACGCGCT | ATTGTGTGGG | GCGATATTGC | GTTAATTGAC |
| 1551 | GGCAATATTA | ACGCTCAAGG | TAGTGGTGAT | ATCGCTAAAA | CCGGTGGTTT |
| 1601 | TGTGGAGACG | TCGGGGCATG | ATTTATTCAT | CAAAGACAAT | GCAATTGTTG |

FIG.6C.

| | | | | | |
|---|---|---|---|---|---|
| 1651 | ACGCCAAAGA | GTGGTTGTTA | GACCCGGATA | ATGTATCTAT | TAATGCAGAA |
| 1701 | ACAGCAGGAC | GCAGCAATAC | TTCAGAAGAC | GATGAATACA | CGGGATCCGG |
| 1751 | GAATAGTGCC | AGCACCCCAA | AACGAAACAA | AGAAAAGACA | ACATTAACAA |
| 1801 | ACACAACTCT | TGAGAGTATA | CTAAAAAAAG | GTACCTTTGT | TAACATCACT |
| 1851 | GCTAATCAAC | GCATCTATGT | CAATAGCTCC | ATTAATTTAT | CCAATGGCAG |
| 1901 | CTTAACTCTT | TGGAGTGAGG | GTCGGAGCGG | TGGCGGCGTT | GAGATTAACA |
| 1951 | ACGATATTAC | CACCGGTGAT | GATACCAGAG | GTGCAAACTT | AACAATTTAC |
| 2001 | TCAGGCGGCT | GGGTTGATGT | TCATAAAAAT | ATCTCACTCG | GGGCGCAAGG |
| 2051 | TAACATAAAC | ATTACAGCTA | AACAAGATAT | CGCCTTTGAG | AAAGGAAGCA |
| 2101 | ACCAAGTCAT | TACAGGTCAA | GGGACTATTA | CCTCAGGCAA | TCAAAAAGGT |
| 2151 | TTTAGATTTA | ATAATGTCTC | TCTAAACGGC | ACTGGCAGCG | GACTGCAATT |
| 2201 | CACCACTAAA | AGAACCAATA | AATACGCTAT | CACAAATAAA | TTTGAAGGGA |
| 2251 | CTTTAAATAT | TTCAGGGAAA | GTGAACATCT | CAATGGTTTT | ACCTAAAAAT |
| 2301 | GAAAGTGGAT | ATGATAAATT | CAAAGGACGC | ACTTACTGGA | ATTTAACCTC |
| 2351 | GAAAGTGGAT | ATGATAAATT | CAAAGGACGC | CCTCACTATT | GACTCCAGAG |
| 2401 | GAAGCGATAG | TGCAGGCACA | CTTACCCAGC | CTTATAATTT | AAACGGTATA |
| 2451 | TCATTCAACA | AAGACACTAC | CTTTAATGTT | GAACGAAATG | CAAGAGTCAA |

FIG. 6D.

```
2501  CTTTGACATC  AAGGCACCAA  TAGGGATAAA  TAAGTATTCT  AGTTTGAATT
2551  ACGCATCATT  TAATGGAAAC  ATTTCAGTTT  CGGGAGGGGG  GAGTGTTGAT
2601  TTCACACTTC  TCGCCTCATC  CTCTAACGTC  CAAACCCCCG  GTGTAGTTAT
2651  AAATTCTAAA  TACTTTAATG  TTTCAACAGG  GTCAAGTTTA  AGATTTAAAA
2701  CTTCAGGCTC  AACAAAAACT  GGCTTCTCAA  TAGAGAAAGA  TTTAACTTTA
2751  AATGCCACCG  GAGGCAACAT  AACACTTTTG  CAAGTTGAAG  GCACCGATGG
2801  AATGATTGGT  AAAGGCATTG  TAGCCAAAAA  AAACATAACC  TTTGAAGGAG
2851  GTAAGATGAG  GTTTGGCTCC  AGGAAAGCCG  TAACAGAAAT  CGAAGGCAAT
2901  GTTACTATCA  ATAACAACGC  TAACGTCACT  CTTATCGGTT  CGGATTTTGA
2951  CAACCATCAA  AAACCTTTAA  CTATTAAAAA  AGATGTCATC  ATTAATAGCG
3001  GCAACCTTAC  CGCTGGAGGC  AATATTGTCA  ATATAGCCGG  AAATCTTACC
3051  GTTGAAAGTA  ACGCTAATTT  CAAAGCTATC  ACAAATTTCA  CTTTTAATGT
3101  AGGCGGCTTG  TTTGACAACA  AAGGCAATTC  AAATATTTCC  ATTGCCAAAG
3151  GAGGGGCTCG  CTTTAAAGAC  ATTGATAATT  CCAAGAATTT  AAGCATCACC
3201  ACCAACTCCA  GCTCCACTTA  CCGCACTATT  ATAAGCGGCA  ATATAACCAA
3251  TAAAAACGGT  GATTTAAATA  TTACGAACGA  AGGTAGTGAT  ACTGAAATGC
```

FIG. 6E.

| | | | | | |
|---|---|---|---|---|---|
| 3301 | AAATTGGCGG | CGATGTCTCG | CAAAAAGAAG | GTAATCTCAC | GATTTCTTCT |
| 3351 | GACAAAATCA | ATATTACCAA | ACAGATAACA | ATCAAGGCAG | GTGTTGATGG |
| 3401 | GGAGAATTCC | GATTCAGACG | CGACAAACAA | TGCCAATCTA | ACCATTAAAA |
| 3451 | CCAAAGAATT | GAAATTAACG | CAAGACCTAA | ATATTTCAGG | TTTCAATAAA |
| 3501 | GCAGAGATTA | CAGCTAAAGA | TGGTAGTGAT | TTAACTATTG | GTAACACCAA |
| 3551 | TAGTGCTGAT | GGTACTAATG | CCAAAAAAGT | AACCTTTAAC | CAGGTTAAAG |
| 3601 | ATTCAAAAAT | CTCTGCTGAC | GGTCACAAGG | TGACACTACA | CAGCAAAGTG |
| 3651 | GAAACATCCG | GTAGTAATAA | CAACACTGAA | GATAGCAGTG | ACAATAATGC |
| 3701 | CGGCTTAACT | ATCGATGCAA | AAAATGTAAC | AGTAAACAAC | AATATTACTT |
| 3751 | CTCACAAAGC | AGTGAGCATC | TCTGCGACAA | GTGGAGAAAT | TACCACTAAA |
| 3801 | ACAGGTACAA | CCATTAACGC | AACCACTGGT | AACGTGGAGA | TAACCGCTCA |
| 3851 | AACAGGTAGT | ATCCTAGGTG | GAATTGAGTC | CAGCTCTGGC | TCTGTAACAC |
| 3901 | TTACTGCAAC | CGAGGGCGCT | CTTGCTGTAA | GCAATATTTC | GGGCAACACC |
| 3951 | GTTACTGTTA | CTGCAAATAG | CGGTGCATTA | ACCACTTTGG | CAGGCTCTAC |
| 4001 | AATTAAAGGA | ACCGAGAGTG | TAACCACTTC | AAGTCAATCA | GGCGATATCG |
| 4051 | GCGGTACGAT | TTCTGGTGGC | ACAGTAGAGG | TTAAAGCAAC | CGAAAGTTTA |

FIG. 6F.

```
4101  ACCACTCAAT CCAATTCAAA AATTAAAGCA ACAACAGGCG AGGCTAACGT
4151  AACAAGTGCA ACAGGTACAA TTGGTGGTAC GATTTCCGGT AATACGGTAA
4201  ATGTTACGGC AAACGCTGGC GATTTAACAG TTGGGAATGG CGCAGAAATT
4251  AATGCGACAG AAGGAGCTGC AACCTTAACT ACATCATCGG GCAAATTAAC
4301  TACCGAAGCT AGTTCACACA TTACTTCAGC CAAGGGTCAG GTAAATCTTT
4351  CAGCTCAGGA TGGTAGCGTT GCAGGAAGTA TTAATGCCGC CAATGTGACA
4401  CTAAATACTA CAGGCACTTT AACTACCGTG AAGGGTTCAA ACATTAATGC
4451  AACCAGCGGT ACCTTGGTTA TTAACGCAAA AGACGCTGAG CTAAATGGCG
4501  CAGCATTGGG TAACCACACA GTGGTAAATG CAACCAACGC AAATGGCTCC
4551  GGCAGCGTAA TCGCGACAAC CTCAAGCAGA GTGAACATCA CTGGGGATTT
4601  AATCACAATA AATGGATTAA ATATCATTTC AAAAAACGGT ATAAACACCG
4651  TACTGTTAAA AGGCGTTAAA ATTGATGTGA AATACATTCA ACCGGGTATA
4701  GCAAGCGTAG ATGAAGTAAT TGAAGCGAAA CGCATCCTTG AGAAGGTAAA
4751  AGATTTATCT GATGAAGAAA GAGAAGCGTT AGCTAAACTT GGCGTAAGTG
4801  CTGTACGTTT TATTGAGCCA AATAATACAA TTACAGTCGA TACACAAAAT
4851  GAATTTGCAA CCAGACCATT AAGTCGAATA GTGATTTCTG AAGGCAGGGC
4901  GTGTTTCTCA AACAGTGATG GCGCGACGGT GTGCGTTAAT ATCGCTGATA
```

FIG. 6G.

```
4951  ACGGGCGGTA GCGGTCAGTA ATTGACAAGG TAGATTTCAT CCTGCAATGA
5001  AGTCATTTTA TTTTCGTATT ATTTACTGTG TGGGTTAAAG TTCAGTACGG
5051  GCTTTACCCA TCTTGTAAAA AATTACGGAG AATACAATAA AGTATTTTTA
5101  ACAGGTTATT ATTATGAAAA ATATAAAAAG CAGATTAAAA CTCAGTGCAA
5151  TATCAGTATT GCTTGGCCTG GCTTCTTCAT CATTGTATGC AGAAGAAGCG
5201  TTTTTAGTAA AAGGCTTTCA GTTATCTGGT GCACTTGAAA CTTTAAGTGA
5251  AGACGCCCAA CTGTCTGTAG CAAAATCTTT ATCTAAATAC CAAGGCTCGC
5301  AAACTTTAAC AAACCTAAAA ACAGCACAGC TTGAATTACA GGCTGTGCTA
5351  GATAAGATTG AGCCAAATAA GTTTGATGTG ATATTGCCAC AACAAACCAT
5401  TACGGATGGC AATATTATGT TTGAGCTAGT CTCGAAATCA GCCGCAGAAA
5451  GCCAAGTTTT TTATAAGGCG AGCCAGGGTT ATAGTGAAGA AAATATCGCT
5501  CGTAGCCTGC CATCTTTGAA ACAAGGAAAA GTGTATGAAG ATGGTCGTCA
5551  GTGGTTCGAT TTGCGTGAAT TCAATATGGC AAAAGAAAAT CCACTTAAAG
5601  TCACTCGCGT GCATTACGAG TTAAACCCTA AAAACAAAAC CTCTGATTTG
5651  GTAGTTGCAG GTTTTTCGCC TTTTGGCAAA ACGCGTAGCT TTGTTTCCTA
5701  TGATAATTTC GGCGCAAGGG AGTTTAACTA TCAACGTGTA AGTCTAGGTT
```

FIG.6H.

```
5751  TTGTAAATGC CAATTTGACC GGACATGATG ATGTATTAAA TCTAAACGCA
5801  TTGACCAATG TAAAAGCACC ATCAAAATCT TATGCGGTAG GCATAGGATA
5851  TACTTATCCG TTTTATGATA AACACCAATC CTTAAGTCTT TATACCAGCA
5901  TGAGTTATGC TGATTCTAAT GATATCGACG GCTTACCAAG TGCGATTAAT
5951  CGTAAATTAT CAAAAGGTCA ATCTATCTCT GCGAATCTGA AATGGAGTTA
6001  TTATCTCCCG ACATTTAACC TTGGAATGGA AGACCAGTTT AAAATTAATT
6051  TAGGCTACAA CTACCGCCAT ATTAATCAAA CATCCGAGTT AAACACCCTG
6101  GGTGCAACGA AGAAAAAATT TGCAGTATCA GGCGTAAGTG CAGGCATTGA
6151  TGGACATATC CAATTTACCC CTAAAACAAT CTTTAATATT GATTTAACTC
6201  ATCATTATTA CGCGAGTAAA TTACCAGGCT CTTTTGGAAT GGAGCGCATT
6251  GGCGAAACAT TTAATCGCAG CTATCACATT AGCACAGCCA GTTTAGGGTT
6301  GAGTCAAGAG TTTGCTCAAG GTTGGCATTT TAGCAGTCAA TTATCGGGTC
6351  AGTTTACTCT ACAAGATATA AGTAGCATAG ATTTATTCTC TGTAACAGGT
6401  ACTTATGGCG TCAGAGGCTT TAAATACGGC GGTGCAAGTG GTGAGCGCGG
6451  TCTTGTATGG CGTAATGAAT TAAGTATGCC AAAATACACC CGCTTTCAAA
6501  TCAGCCCTTA TGCGTTTTAT GATGCAGGTC AGTTCCGTTA TAATAGCGAA
6551  AATGCTAAAA CTTACGGCGA AGATATGCAC ACGGTATCCT CTGCGGGTTT
```

FIG.6I.

```
6601  AGGCATTAAA ACCTCTCCTA CACAAAACTT AAGCTTAGAT GCTTTTGTTG
6651  CTCGTCGCTT TGCAAATGCC AATAGTGACA ATTTGAATGG CAACAAAAAA
6701  CGCACAAGCT CACCTACAAC CTTCTGGGGT AGATTAACAT TCAGTTTCTA
6751  ACCCTGAAAT TTAATCAACT GGTAAGCGTT CCGCCTACCA GTTTATAACT
6801  ATATGCTTTA CCCGCCAATT TACAGTCTAT ACGCAACCCT GTTTTCATCC
6851  TTATATATCA AACAAACTAA GCAAACCAAG CAAACCAAGC AAACCAAGCA
6901  AACCAAGCAA ACCAAGCAAA CCAAGCAAAC CAAGCAAACC AAGCAAACCA
6951  AGCAAACCAA GCAAACCAAG CAAACCAAGC AAACCAAGCA ATGCTAAAAA
7001  ACAATTTATA TGATAAACTA AAACATACTC CATACCATGG CAATACAAGG
7051  GATTTAATAA TATGACAAAA GAAAATTTAC AAAGTGTTCC ACAAAATACG
7101  ACCGCTTCAC TTGTAGAATC AAACAACGAC CAAACTTCCC TGCAAATACT
7151  TAAACAACCA CCCAAACCCA ACCTATTACG CCTGGAACAA CATGTCGCCA
7201  AAAAAGATTA TGAGCTTGCT TGCCGCGAAT TAATGGCGAT TTTGGAAAAA
7251  ATGGACGCTA ATTTTGGAGG CGTTCACGAT ATTGAATTTG ACGCACCTGC
7301  TCAGCTGGCA TATCTACCCG AAAAACTACT AATTCATTTT GCCACTCGTC
7351  TCGCTAATGC AATTACAACA CTCTTTTCCG ACCCCGAATT GGCAATTTCC
```

FIG. 6J.

```
7401  GAAGAAGGGG CATTAAAGAT GATTAGCCTG CAACGCTGGT TGACGCTGAT
7451  TTTTGCCTCT TCCCCCTACG TTAACGCAGA CCATATTCTC AATAAATATA
7501  ATATCAACCC AGATTCCGAA GGTGGCTTTC ATTTAGCAAC AGACAACTCT
7551  TCTATTGCTA AATTCTGTAT TTTTTACTTA CCCGAATCCA ATGTCAATAT
7601  GAGTTTAGAT GCGTTATGGG CAGGGAATCA ACAACTTTGT GCTTCATTGT
7651  GTTTTGCGTT GCAGTCTTCA CGTTTTATTG GTACTGCATC TGCGTTTCAT
7701  AAAAGAGCGG TGGTTTTACA GTGGTTTCCT AAAAAACTCG CCGAAATTGC
7751  TAATTTAGAT GAATTGCCTG CAAATATCCT TCATGATGTA TATATGCACT
7801  GCAGTTATGA TTTAGCAAAA AACAAGCACG ATGTTAAGCG TCCATTAAAC
7851  GAACTTGTCC GCAAGCATAT CCTCACGCAA GGATGGCAAG ACCGCTACCT
7901  TTACACCTTA GGTAAAAAGG ACGGCAAACC TGTGATGATG GTACTGCTTG
7951  AACATTTTAA TTCGGGACAT TCGATTTATC GCACGCATTC AACTTCAATG
8001  ATTGCTGCTC GAGAAAAATT CTATTTAGTC GGCTTAGGCC ATGAGGGCGT
8051  TGATAACATA GGTCGAGAAG TGTTTGACGA GTTCTTTGAA ATCAGTAGCA
8101  ATAATATAAT GGAGAGACTG TTTTTTATCC GTAAACAGTG CGAAACTTTC
8151  CAACCCGCAG TGTTCTATAT GCCAAGCATT GGCATGGATA TTACCACGAT
```

FIG. 6K.

```
8201  TTTTGTGAGC AACACTCGGC TTGCCCCTAT TCAAGCTGTA GCCTTGGGTC
8251  ATCCTGCCAC TACGCATTCT GAATTTATTG ATTATGTCAT CGTAGAAGAT
8301  GATTATGTGG GCAGTGAAGA TTGTTTAGC  GAAACCCTTT TACGCTTACC
8351  CAAAGATGCC CTACCTTATG TACCATCTGC ACTCGCCCCA CAAAAAGTGG
8401  ATTATGTACT CAGGGAAAAC CCTGAAGTAG TCAATATCGG TATTGCCGCT
8451  ACCACAATGA AATTAAACCC TGAATTTTTG CTAACATTGC AAGAAATCAG
8501  AGATAAAGCT AAAGTCAAAA TACATTTTCA TTTCGCACTT GGACAATCAA
8551  CAGGCTTGAC ACACCCTTAT GTCAAATGGT TTATCGAAAG CTATTTAGGT
8601  GACGATGCCA CTGCACATCC CCACGCACCT TATCACGATT ATCTGGCAAT
8651  ATTGCGTGAT TGCGATATGC TACTAAATCC GTTTCCTTTC GGTAATACTA
8701  ACGGCATAAT TGATATGGTT ACATTAGGTT TAGTTGGTGT ATGCAAAACG
8751  GGGGATGAAG TACATGAACA TATTGATGAA GGTCTGTTTA AACGCTTAGG
8801  ACTACCAGAA TGGCTGATAG CCGACACACG AGAAACATAT ATTGAATGTG
8851  CTTTGCGTCT AGCAGAAAAC CATCAAGAAC GCCTTGAACT CCGTCGTTAC
8901  ATCATAGAAA ACAACGGCTT ACAAAAGCTT TTTACAGGCG ACCCTCGTCC
8951  ATTGGGCAAA ATACTGCTTA AGAAAACAAA TGAATGGAAG CGGAAGCACT
9001  TGAGTAAAAA ATAACGGTTT TTTAAAGTAA AAGTGCGGTT AATTTTCAAA
```

FIG. 6L.

```
9051   GCGTTTTAAA AACCTCTCAA AAATCAACCG CACTTTTATC TTTATAACGC
9101   TCCCGCGCGC TGACAGTTTA TCTCTTTCTT AAAATACCCA TAAAATTGTG
9151   GCAATAGTTG GGTAATCAAA TTCAATTGTT GATACGGCAA ACTAAAGACG
9201   GCGCGTTCTT CGGCAGTCAT C
```

FIG. 7A.

| | | | | | |
|---|---|---|---|---|---|
| 1 | CGCCACTTCA | ATTTTGGATT | GTTGAAATTC | AACTAACCAA | AAAGTGCGGT |
| 51 | TAAAATCTGT | GGAGAAAATA | GGTTGTAGTG | AAGAACGAGG | TAATTGTTCA |
| 101 | AAAGGATAAA | GCTCTCTTAA | TTGGGCATTG | GTTGGCGTTT | CTTTTTCGGT |
| 151 | TAATAGTAAA | TTATATTCTG | GACGACTATG | CAATCCACCA | ACAACTTTAC |
| 201 | CGTTGGTTTT | AAGCGTTAAT | GTAAGTTCTT | GCTCTTCTTG | GCGAATACGT |
| 251 | AATCCCATTT | TTTGTTTAGC | AAGAAAATGA | TCGGGATAAT | CATAATAGGT |
| 301 | GTTGCCCAAA | AATAAATTTT | GATGTTCTAA | AATCATAAAT | TTTGCAAGAT |
| 351 | ATTGTGGCAA | TTCAATACCT | ATTTGTGGCG | AAATCGCCAA | TTTTAATTCA |
| 401 | ATTTCTTGTA | GCATAATATT | TCCCACTCAA | ATCAACTGGT | TAAATATACA |
| 451 | AGATAATAAA | AATAAATCAA | GATTTTTGTG | ATGACAAACA | ACAATTACAA |
| 501 | CACCTTTTTT | GCAGTCTATA | TGCAAATATT | TTAAAAAAAT | AGTATAAATC |
| 551 | CGCCATATAA | AATGGTATAA | TCTTTCATCT | TTCATCTTTC | ATCTTTCATC |
| 601 | TTTCATCTTT | CATCTTTCAT | CTTTCATCTT | TCATCTTTCA | TCTTTCATCT |
| 651 | TTCATCTTTC | ATCTTTCATC | TTTCATCTTT | CACATGAAAT | GATGAACCGA |
| 701 | GGGAAGGGAG | GGAGGGGCAA | GAATGAAGAG | GGAGCTGAAC | GAACGCAAAT |
| 751 | GATAAAGTAA | TTTAATTGTT | CAACTAACCT | TAGGAGAAAA | TATGAACAAG |

FIG.7B.

```
801  ATATATCGTC TCAAATTCAG CAAACGCCTG AATGCTTTGG TTGCTGTGTC
851  TGAATTGGCA CGGGGTTGTG ACCATTCCAC AGAAAAAGGC AGCGAAAAAC
901  CTGCTCGCAT GAAAGTGCGT CACTTAGCGT TAAAGCCACT TTCCGCTATG
951  TTACTATCTT TAGGTGTAAC ATCTATTCCA CAATCTGTTT TAGCAAGCGG
1001 CAATTTAACA TCGACCAAAA TGAAATGGTG CAGTTTTTAC AAGAAAACAA
1051 GTAATAAAAC CATTATCCGC AACAGTGTTG ACGCTATCAT TAATTGGAAA
1101 CAATTTAACA TCGACCAAAA TGAAATGGTG CAGTTTTTAC AAGAAAACAA
1151 CAACTCCGCC GTATTCAACC GTGTTACATC TAACCAAATC TCCCAATTAA
1201 AAGGGATTTT AGATTCTAAC GGACAAGTCT TTTTAATCAA CCCAAATGGT
1251 ATCACAATAG GTAAAGACGC AATTATTAAC ACTAATGGCT TTACGGCTTC
1301 TACGCTAGAC ATTTCTAACG AAAACATCAA GGCGCGTAAT TTCACCTTCG
1351 AGCAAACCAA AGATAAAGCG CTCGCTGAAA TTGTGAATCA CGGTTTAATT
1401 ACTGTCGGTA AAGACGGCAG TGTAAATCTT ATTGGTGGCA AAGTGAAAAA
1451 CGAGGGTGTG ATTAGCGTAA ATGGTGGCAG CATTTCTTTA CTCGCAGGGC
1501 AAAAAATCAC CATCAGCGAT ATAATAAACC CAACCATTAC TTACAGCATT
1551 GCCGCGCCTG AAAATGAAGC GGTCAATCTG GGCGATATTT TTGCCAAAGG
```

FIG. 7C.

1601 CGGTAACATT AATGTCCGTG CTGCCACTAT TCGAAACCAA GGTAAACTTT
1651 CTGCTGATTC TGTAAGCAAA GATAAAAGCG GCAATATTGT TCTTTCCGCC
1701 AAAGAGGGTG AAGCGGAAAT TGGCGGTGTA ATTTCCGCTC AAAATCAGCA
1751 AGCTAAAGGC GGCAAGCTGA TGATTACAGG CGATAAAGTC ACATTAAAAA
1801 CAGGTGCAGT TATCGACCTT TCAGGTAAAG AAGGGGGAGA AACTTACCTT
1851 GGCGGTGACG AGCGCGGCGA AGGTAAAAAC GGCATTCAAT TAGCAAAGAA
1901 AACCTCTTTA GAAAAAGGCT CAACCATCAA TGTATCAGGC AAAGAAAAAG
1951 GCGGACGCGC TATTGTGTGG GGCGATATTG CGTTAATTGA CGGCAATATT
2001 AACGCTCAAG GTAGTGGTGA TATCGCTAAA ACCGGTGGTT TTGTGGAGAC
2051 ATCGGGGCAT TATTTATCCA TTGACAGCAA TGCAATTGTT AAAACAAAAG
2101 AGTGGTTGCT AGACCCTGAT GATGTAACAA TTGAAGCCGA AGACCCCCTT
2151 CGCAATAATA CCGGTATAAA TGATGAATTC CCAACAGGCA CCGGTGAAGC
2201 AAGCGACCCT AAAAAAAATA GCGAACTCAA AACAACGCTA ACCAATACAA
2251 CTATTTCAAA TTATCTGAAA AACGCCTGGA CAATGAATAT AACGGCATCA
2301 AGAAAACTTA CCGTTAATAG CTCAATCAAC ATCGGAAGCA ACTCCCACTT
2351 AATTCTCCAT AGTAAAGGTC AGCGTGGCGG AGGCGTTCAG ATTGATGGAG
2401 ATATTACTTC TAAAGGCGGA AATTTAACCA TTTATTCTGG CGGATGGGTT

FIG. 7D.

```
2451  GATGTTCATA AAAATATTAC GCTTGATCAG GGTTTTTTAA ATATTACCGC
2501  CGCTTCCGTA GCTTTTGAAG GTGGAAATAA CAAAGCACGC GACGCGGCAA
2551  ATGCTAAAAT TGTCGCCCAG GGCACTGTAA CCATTACAGG AGAGGGAAAA
2601  GATTTCAGGG CTAACAACGT ATCTTTAAAC GGAACGGGTA AAGGTCTGAA
2651  TATCATTTCA TCAGTGAATA ATTTAACCCA CAATCTTAGT GGCACAATTA
2701  ACATATCTGG GAATATAACA ATTAACCAAA CTACGAGAAA GAACACCTCG
2751  TATTGGCAAA CCAGCCATGA TTCGCACTGG AACGTCAGTG CTCTTAATCT
2801  AGAGACAGGC GCAAATTTTA CCTTTATTAA ATACATTTCA AGCAATAGCA
2851  AAGGCTTAAC AACACAGTAT AGAAGCTCTG CAGGGGTGAA TTTTAACGGC
2901  GTAAATGGCA ACATGTCATT CAATCTCAAA GAAGGAGCGA AAGTTAATTT
2951  CAAATTAAAA CCAAACGAGA ACATGAACAC AAGCAAACCT TTACCAATTC
3001  GGTTTTTAGC CAATATCACA GCCACTGGTG GGGGCTCTGT TTTTTTTGAT
3051  ATATATGCCA ACCATTCTGG CAGAGGGGCT GAGTTAAAAA TGAGTGAAAT
3101  TAATATCTCT AACGGCGCTA ATTTTACCTT AAATTCCCAT GTTCGCGGCG
3151  ATGACGCTTT TAAAATCAAC AAAGACTTAA CCATAAATGC AACCAATTCA
3201  AATTTCAGCC TCAGACAGAC GAAAGATGAT TTTTATGACG GGTACGCACG
```

FIG. 7E.

| | | | | | |
|---|---|---|---|---|---|
| 3251 | CAATGCCATC | AATTCAACCT | ACAACATATC | CATTCTGGGC | GGTAATGTCA |
| 3301 | CCCTTGGTGG | ACAAAACTCA | AGCAGCAGCA | TTACGGGGAA | TATTACTATC |
| 3351 | GAGAAAGCAG | CAAATGTTAC | GCTAGAAGCC | AATAACGCCC | CTAATCAGCA |
| 3401 | AAACATAAGG | GATAGAGTTA | TAAAACTTGG | CAGCTTGCTC | GTTAATGGGA |
| 3451 | GTTTAAGTTT | AACTGGCGAA | AATGCAGATA | TTAAAGGCAA | TCTCACTATT |
| 3501 | TCAGAAAGCG | CCACTTTTAA | AGGAAAGACT | AGAGATACCC | TAAATATCAC |
| 3551 | CGGCAATTTT | ACCAATAATG | GCACTGCCGA | AATTAATATA | ACACAAGGAG |
| 3601 | TGGTAAAACT | TGGCAATGTT | ACCAATGATG | GTGATTTAAA | CATTACCACT |
| 3651 | CACGCTAAAC | GCAACCAAAG | AAGCATCATC | GGCGGAGATA | TAATCAACAA |
| 3701 | AAAAGGAAGC | TTAAATATTA | CAGACAGTAA | TAATGATGCT | GAAATCCAAA |
| 3751 | TTGGCGGCAA | TATCTCGCAA | AAAGAAGGCA | ACCTCACGAT | TTCTTCCGAT |
| 3801 | AAAATTAATA | TCACCAAACA | GATAACAATC | AAAAAGGGTA | TTGATGGAGA |
| 3851 | GGACTCTAGT | TCAGATGCGA | CAAGTAATGC | CAACCTAACT | ATTAAAACCA |
| 3901 | AAGAATTGAA | ATTGACAGAA | GACCTAAGTA | TTTCAGGTTT | CAATAAAGCA |
| 3951 | GAGATTACAG | CCAAAGATGG | TAGAGATTTA | ACTATTGGCA | ACAGTAATGA |
| 4001 | CGGTAACAGC | GGTGCCGAAG | CCAAAACAGT | AACTTTTAAC | AATGTTAAAG |

FIG. 7F.

```
4051   ATTCAAAAT   CTCTGCTGAC  GGTCACAATG  TGACACTAAA  TAGCAAAGTG
4101   AAAACATCTA  GCAGCAATGG  CGGACGTGAA  AGCAATAGCG  ACAACGATAC
4151   CGGCTTAACT  ATTACTGCAA  AAAATGTAGA  AGTAAACAAA  GATATTACTT
4201   CTCTCAAAAC  AGTAAATATC  ACCGCGTCGG  AAAAGGTTAC  CACCACAGCA
4251   GGCTCGACCA  TTAACGCAAC  AAATGGCAAA  GCAAGTATTA  CAACCAAAAC
4301   AGGTGATATC  AGCGGTACGA  TTTCCGGTAA  CACGGTAAGT  GTTAGCGCGA
4351   CTGGTGATTT  AACCACTAAA  TCCGGCTCAA  AAATTGAAGC  GAAATCGGGT
4401   GAGGCTAATG  TAACAAGTGC  AACAGGTACA  ATTGGCGGTA  CAATTTCCGG
4451   TAATACGGTA  AATGTTACGG  CAAACGCTGG  CGATTTAACA  GTTGGGAATG
4501   GCGCAGAAAT  TAATGCGACA  GAAGGAGCTG  CAACCTTAAC  CGCAACAGGG
4551   AATACCTTGA  CTACTGAAGC  CGGTTCTAGC  ATCACTTCAA  CTAAGGGTCA
4601   GGTAGACCTC  TTGGCTCAGA  ATGGTAGCAT  CGCAGGAAGC  ATTAATGCTG
4651   CTAATGTGAC  ATTAAATACT  ACAGGCACCT  TAACCACCGT  GGCAGGCTCG
4701   GATATTAAAG  CAACCAGCGG  CACCTTGGTT  ATTAACGCAA  AAGATGCTAA
4751   GCTAAATGGT  GATGCATCAG  GTGATAGTAC  AGAAGTGAAT  GCAGTCAACG
4801   ACTGGGGATT  TGGTAGTGTG  ACTGCGGCAA  CCTCAAGCAG  TGTGAATATC
4851   ACTGGGGATT  TAAACACAGT  AAATGGGTTA  AATATCATTT  CGAAAGATGG
```

FIG. 7G.

```
4901  TAGAAACACT GTGCGCTTAA GAGGCAAGGA AATTGAGGTG AAATATATCC
4951  AGCCAGGTGT AGCAAGTGTA GAAGAAGTAA TTGAAGCGAA ACGCGTCCTT
5001  GAAAAAGTAA AAGATTTATC TGATGAAGAA AGAGAAACAT TAGCTAAACT
5051  TGGTGTAAGT GCTGTACGTT TTGTTGAGCC AAATAATACA ATTACAGTCA
5101  ATACACAAAA TGAATTTACA ACCAGACCGT CAAGTCAAGT GATAATTTCT
5151  GAAGGTAAGG CGTGTTTCTC AAGTGGTAAT GGCGCACGAG TATGTACCAA
5201  TGTTGCTGAC GATGGACAGC CGTAGTCAGT AATTGACAAG GTAGATTTCA
5251  TCCTGCAATG AAGTCATTTT ATTTTCGTAT TATTTACTGT GTGGGTTAAA
5301  GTTCAGTACG GGCTTTACCC ATCTTGTAAA AAATTACGGA GAATACAATA
5351  AAGTATTTTT AACAGGTTAT TATTATGAAA AATATAAAAA GCAGATTAAA
5401  ACTCAGTGCA ATATCAGTAT TGCTTGGCCT GGCTTCTTCA TCATTGTATG
5451  CAGAAGAAGC GTTTTTAGTA AAAGGCTTTC AGTTATCTGG TGCACTTGAA
5501  ACTTTAAGTG AAGACGCCCA ACTGTCTGTA GCAAAATCTT TATCTAAATA
5551  CCAAGGCTCG CAAACTTTAA CAAACCTAAA AACAGCACAG CTTGAATTAC
5601  AGGCTGTGCT AGATAAGATT GAGCCAAATA AATTTGATGT GATATTGCCG
5651  CAACAAACCA TTACGGATGG CAATATCATG TTTGAGCTAG TCTCGAAATC
```

FIG. 7H.

```
5701  AGCCGCAGAA AGCCAAGTTT TTTATAAGGC GAGCCAGGGT TATAGTGAAG
5751  AAAATATCGC TCGTAGCCTG CCATCTTTGA AACAAGGAAA AGTGTATGAA
5801  GATGGTCGTC AGTGGTTCGA TTTGCGTGAA TTTAATATGG CAAAAGAAAA
5851  CCCGCTTAAG GTTACCCGTG TACATTACGA ACTAAACCCT AAAAACAAAA
5901  CCTCTAATTT GATAATTGCG GGCTTCTCGC CTTTTGGTAA AACGCGTAGC
5951  TTTATTTCTT ATGATAATTT CGGCGCGAGA GAGTTTAACT ACCAACGTGT
6001  AAGCTTGGGT TTTGTTAATG CCAATTTAAC TGGTCATGAT GATGTGTTAA
6151  TTATACCAGT ATGAGTTATG CTGATTCTAA TGATATCGAC GGCTTACCAA
6201  GTGCGATTAA TCGTAAATTA TCAAAAGGTC AATCTATCTC TGCGAATCTG
6251  AAATGGAGTT ATTATCTCCC AACATTTAAC CTTGGCATGG AAGACCAATT
6301  TAAAATTAAT TTAGGCTACA ACTACCGCCA TATTAATCAA ACCTCCGCGT
6351  TAAATCGCTT GGGTGAAACG AAGAAAAAAT TTGCAGTATC AGGCGTAAGT
6401  GCAGGCATTG ATGGACATAT CCAATTTACC CCTAAAACAA TCTTTAATAT
6451  TGATTTAACT CATCATTATT ACGCGAGTAA ATTACCAGGC TCTTTTGGAA
6501  TGGAGCGCAT TGGCGAAACA TTTAATCGCA GCTATCACAT TAGCACAGCC
6551  AGTTTAGGGT TGAGTCAAGA GTTTGCTCAA GGTTGGCATT TTAGCAGTCA
6601  ATTATCAGGT CAATTTACTC TACAAGATAT TAGCAGTATA GATTTATTCT
```

FIG. 7I.

| | | | | | |
|---|---|---|---|---|---|
| 6651 | CTGTAACAGG | TACTTATGGC | GTCAGAGGCT | TTAAATACGG | CGGTGCAAGT |
| 6701 | GGTGAGCGCG | GTCTTGTATG | GCGTAATGAA | TTAAGTATGC | CAAAATACAC |
| 6751 | CCGCTTCCAA | ATCAGCCCTT | ATGCGTTTTA | TGATGCAGGT | CAGTTCCGTT |
| 6801 | ATAATAGCGA | AAATGCTAAA | ACTTACGGCG | AAGATATGCA | CACGGTATCC |
| 6851 | TCTGCGGGTT | TAGGCATTAA | AACCTCTCCT | ACACAAAACT | TAAGCCTAGA |
| 6901 | TGCTTTTGTT | GCTCGTCGCT | TTGCAAATGC | CAATAGTGAC | AATTTGAATG |
| 6951 | GCAACAAAAA | ACGCACAAGC | TCACCTACAA | CCTTCTGGGG | GAGATTAACA |
| 7001 | TTCAGTTTCT | AACCCTGAAA | TTTAATCAAC | TGGTAAGCGT | TCCGCCTACC |
| 7051 | AGTTTATAAC | TATATGCTTT | ACCCGCCAAT | TTACAGTCTA | TAGGCAACCC |
| 7101 | TGTTTTTACC | CTTATATATC | AAATAAACAA | GCTAAGCTGA | GCTAAGCAAA |
| 7151 | CCAAGCAAAC | TCAAGCAAGC | CAAGTAATAC | TAAAAAAACA | ATTTATATGA |
| 7201 | TAAACTAAAG | TATACTCCAT | GCCATGGCGA | TACAAGGGAT | TTAATAATAT |
| 7251 | GACAAAAGAA | AATTTGCAAA | ACGCTCCTCA | AGATGCGACC | GCTTTACTTG |
| 7301 | CGGAATTAAG | CAACAATCAA | ACTCCCCTGC | GAATATTTAA | ACAACCACGC |
| 7351 | AAGCCCAGCC | TATTACGCTT | GGAACAACAT | ATCGCAAAAA | AAGATTATGA |
| 7401 | GTTTGCTTGT | CGTGAATTAA | TGGTGATTCT | GGAAAAAATG | GACGCTAATT |

FIG.7J.

```
7451  TTGGAGGCGT TCACGATATT GAATTTGACG CACCCGCTCA GCTGGCATAT
7501  CTACCCGAAA AATTACTAAT TTATTTTGCC ACTCGTCTCG CTAATGCAAT
7551  TACAACACTC TTTTCCGACC CCGAATTGGC AATTTCTGAA GAAGGGGCGT
7601  TAAAGATGAT TAGCCTGCAA CGCTGGTTGA CGCTGATTTT TGCCTCTTCC
7651  CCCTACGTTA ACGCAGACCA TATTCTCAAT AAATATAATA TCAACCCAGA
7701  TTCCGAAGGT GGCTTTCATT TAGCAACAGA CAACTCTTCT ATTGCTAAAT
7751  TCTGTATTTT TTACTTACCC GAATCCAATG TCAATATGAG TTTAGATGCG
7801  TTATGGGCAG GGAATCAACA ACTTTGTGCT TCATTGTGTT TTGCGTTGCA
7851  GTCTTCACGT TTTATTGGTA CCGCATCTGC GTTTCATAAA AGAGCGGTGG
7901  TTTTACAGTG GTTTCCTAAA AAACTCGCCG AAATTGCTAA TTTAGATGAA
7951  TTGCCTGCAA ATATCCTTCA TGATGTATAT ATGCACTGCA GTTATGATTT
8001  AGCAAAAAAC AAGCACGATG TTAAGCGTCC ATTAAACGAA CTTGTCCGCA
8051  AGCATATCCT CACGCAAGGA TGGCAAGACC GCTACCTTTA CACCTTAGGT
8101  AAAAAGGACG GCAAACCTGT GATGATGGTA CTGCTTGAAC ATTTTAATTC
8151  GGGACATTCG ATTTATCGTA CACATTCAAC TTCAATGATT GCTGCTCGAG
8201  AAAAATTCTA TTTAGTCGGC TTAGGCCATG AGGGCGTTGA TAAAATAGGT
```

FIG. 7K.

```
8251  CGAGAAGTGT TTGACGAGTT CTTTGAAATC AGTAGCAATA ATATAATGGA
8301  GAGACTGTTT TTTATCCGTA AACAGTGCGA AACTTTCCAA CCCGCAGTGT
8351  TCTATATGCC AAGCATTGGC ATGGATATTA CCACGATTTT TGTGAGCAAC
8401  ACTCGGCTTG CCCCTATTCA AGCTGTAGCC CTGGGTCATC CTGCCACTAC
8451  GCATTCTGAA TTTATTGATT ATGTCATCGT AGAAGATGAT TATGTGGGCA
8501  GTGAAGATTG TTTCAGCGAA ACCCTTTTAC GCTTACCCAA AGATGCCCTA
8551  CCTTATGTAC CTTCTGCACT CGCCCCACAA AAAGTGGATT ATGTACTCAG
8601  GGAAAACCCT GAAGTAGTCA ATATCGGTAT TGCCGCTACC ACAATGAAAT
8651  TAAACCCTGA ATTTTTGCTA ACATTGCAAG AAATCAGAGA TAAAGCTAAA
8701  GTCAAAATAC ATTTTCATTT CGCACTTGGA CAATCAACAG GCTTGACACA
8751  CCCTTATGTC AAATGGTTTA TCGAAAGCTA TTTAGGTGAC GATGCCACTG
8801  CACATCCCCA CGCACCTTAT CACGATTATC TGGCAATATT GCGTGATTGC
8851  GATATGCTAC TAAATCCGTT TCCTTTCGGT AATACTAACG GCATAATTGA
8901  TATGGTTACA TTAGGTTTAG TTGGTGTATG CAAAACGGGG GATGAAGTAC
8951  ATGAACATAT TGATGAAGGT CTGTTTAAAC GCTTAGGACT ACCAGAATGG
9001  CTGATAGCCG ACACACGAGA AACATATATT GAATGTGCTT TGCGTCTAGC
9051  AGAAAACCAT CAAGAACGCC TTGAACTCCG TCGTTACATC ATAGAAAACA
```

FIG. 7L.

```
9101   ACGGCTTACA  AAAGCTTTTT  ACAGGCGACC  CTCGTCCATT  GGGCAAAATA
9151   CTGCTTAAGA  AAACAAATGA  ATGGAAGCGG  AAGCACTTGA  GTAAAAAATA
9201   ACGGTTTTTT  AAAGTAAAAG  TGCGGTTAAT  TTTCAAAGCG  TTTTAAAAAC
9251   CTCTCAAAAA  TCAACCGCAC  TTTTATCTTT  ATAACGATCC  CGCACGCTGA
9301   CAGTTTATCA  GCCTCCCGCC  ATAAAACTCC  GCCTTTCATG  GCGGAGATTT
9351   TAGCCAAAAC  TGGCAGAAAT  TAAAGGCTAA  AATCACCAAA  TTGCACCACA
9401   AAATCACCAA  TACCCACAAA  AAA
```

FIG. 8A.

```
  1 GATCAATCTG GGCGATATTT TTGCCAAAGG TGGTAACATT AATGTCCGCG
 51 CTGCCACTAT TCGCAATAAA GGTAAACTTT CTGCCGACTC TGTAAGCAAA
101 GATAAAAGTG GTAACATTGT TCTCTCTGCC AAAGAAGGTG AAGCGGAAAT
151 TGGCGGTGTA ATTTCCGCTC AAAATCAGCA AGCCAAAGGT GGTAAGTTGA
201 TGATTACAGG CGATAAAGTT ACATTGAAAA CGGGTGCAGT TATCGACCTT
251 TCGGGTAAAG AAGGGGGAGA AACTTATCTT GGCGGTGACG AGCGTGGCGA
301 AGGTAAAAAC GGCATTCAAT TAGCAAAGAA AACCACTTTA GAAAAAGGCT
351 CAACAATTAA TGTGTCAGGT AAAGAAAAAG GTGGGCGCGC TATTGTATGG
401 GGCGATATTG CGTTAATTGA CGGCAATATT AATGCCCAAG GTAAAGATAT
451 CGCTAAAACT GGTGGTTTTG TGGAGACGTC GGGGCATTAC TTATCCATTG
501 ATGATAACGC AATTGTTAAA ACAAAAGAAT GGCTACTAGA CCCAGAGAAT
551 GTGACTATTG AAGCTCCTTC CGCTTCTCGC GTCGAGCTGG GTGCCGATAG
601 GAATTCCCAC TCGGCAGAGG TGATAAAAGT GACCCTAAAA AAAAATAACA
651 CCTCCTTGAC AACACTAACC AATACAACCA TTTCAAATCT TCTGAAAAGT
701 GCCCACGTGG TGAACATAAC GGCAAGGAGA AAACTTACCG TTAATAGCTC
751 TATCAGTATA GAAAGAGGCT CCCACTTAAT TCTCCACAGT GAAGGTCAGG
```

FIG. 8B.

| | | | | | |
|---|---|---|---|---|---|
| 801 | GCGGTCAAGG | TGTTCAGATT | GATAAAGATA | TTACTTCTGA | AGGCGGAAAT |
| 851 | TTAACCATTT | ATTCTGGCGG | ATGGGTTGAT | GTTCATAAAA | ATATTACGCT |
| 901 | TGGTAGCGGC | TTTTTAAACA | TCACAACTAA | AGAAGGAGAT | ATCGCCTTCG |
| 951 | AAGACAAGTC | TGGACGGAAC | AACCTAACCA | TTACAGCCCA | AGGGACCATC |
| 1001 | ACCTCAGGTA | ATAGTAACGG | CTTTAGATTT | AACAACGTCT | CTCTAAACAG |
| 1051 | CCTTGGCGGA | AAGCTGAGCT | TTACTGACAG | CAGAGAGGAC | AGAGGTAGAA |
| 1101 | GAACTAAGGG | TAATATCTCA | AACAAATTTG | ACGGAACGTT | AAACATTTCC |
| 1151 | GGAACTGTAG | ATATCTCAAT | GAAAGCACCC | AAAGTCAGCT | GGTTTTACAG |
| 1201 | AGACAAAGGA | CGCACCTACT | GGAACGTAAC | CACTTTAAAT | GTTACCTCGG |
| 1251 | GTAGTAAATT | TAACCTCTCC | ATTGACAGCA | CAGGAAGTGG | CTCAACAGGT |
| 1301 | CCAAGCATAC | GCAATGCAGA | ATTAAATGGC | ATAACATTTA | ATAAAGCCAC |
| 1351 | TTTTAATATC | GCACAAGGCT | CAACAGCTAA | CTTTAGCATC | AAGGCATCAA |
| 1401 | TAATGCCCTT | TAAGAGTAAC | GCTAACTACG | CATTATTTAA | TGAAGATATT |
| 1451 | TCAGTCTCAG | GGGGGGGTAG | CGTTAATTTC | AAACTTAACG | CCTCATCTAG |
| 1501 | CAACATACAA | ACCCCTGGCG | TAATTATAAA | ATCTCAAAAC | TTTAATGTCT |
| 1551 | CAGGAGGGTC | AACTTTAAAT | CTCAAGGCTG | AAGGTTCAAC | AGAAACCGCT |
| 1601 | TTTTCAATAG | AAAATGATTT | AAACTTAAAC | GCCACCGGTG | GCAATATAAC |

FIG. 8C.

```
1651  AATCAGACAA GTCGAGGGTA CCGATTCACG CGTCAACAAA GGTGTCGCAG
1701  CCAAAAAAAA CATAACTTTT AAAGGGGGTA ATATCACCTT CGGCTCTCAA
1751  AAAGCCACAA CAGAAATCAA AGGCAATGTT ACCATCAATA AAAACACTAA
1801  CGCTACTCTT CGTGGTGCGA ATTTTGCCGA AAACAAATCG CCTTTAAATA
1851  TAGCAGGAAA TGTTATTAAT AATGGCAACC TTACCACTGC CGGCTCCATT
1901  ATCAATATAG CCGGAAATCT TACTGTTTCA AAAGGCGCTA ACCTTCAAGC
1951  TATAACAAAT TACACTTTTA ATGTAGCCGG CTCATTTGAC AACAATGGCG
2001  CTTCAAACAT TTCCATTGCC AGAGGAGGGG CTAAATTTAA AGATATCAAT
2051  AACACCAGTA GCTTAAATAT TACCACCAAC TCTGATACCA CTTACCGCAC
2101  CATTATAAAA GGCAATATAT CCAACAAATC AGGTGATTTG AATATTATTG
2151  ATAAAAAAAG CGACGCTGAA ATCCAAATTG GCGGCAATAT CTCACAAAAA
2201  GAAGGCAATC TCACAATTTC TTCTGATAAA GTAAATATTA CCAATCAGAT
2251  AACAATCAAA GCAGGCGTTG AAGGGGGGCG TTCTGATTCA AGTGAGGCAG
2301  AAAATGCTAA CCTAACTATT CAAACCAAAG AGTTAAAATT GGCAGGAGAC
2351  CTAAATATTT CAGGCTTTAA TAAAGCAGAA ATTACAGCTA AAATGGCAG
2401  TGATTTAACT ATTGGCAATG CTAGCGGTGG TAATGCTGAT GCTAAAAAAG
```

FIG. 8D.

```
2451 TGACTTTTGA CAAGGTTAAA GATTCAAAAA TCTCGACTGA CGGTCACAAT
2501 GTAACACTAA ATAGCGAAGT GAAAACGTCT AATGGTAGTA GCAATGCTGG
2551 TAATGATAAC AGCACCGGTT TAACCATTTC CGCAAAAGAT GTAACGGTAA
2601 ACAATAACGT TACCTCCCAC AAGACAATAA ATATCTCTGC CGCAGCAGGA
2651 AATGTAACAA CCAAAGAAGG CACAACTATC AATGCAACCA CAGGCAGCGT
2701 GGAAGTAACT GCTCAAAATG GTACAATTAA AGGCAACATT ACCTCGCAAA
2751 ATGTAACAGT GACAGCAACA GAAAATCTTG TTACCACAGA GAATGCTGTC
2801 ATTAATGCAA CCAGCGGCAC AGTAAACATT AGTACAAAAA CAGGGGATAT
2851 TAAAGGTGGA ATTGAATCAA CTTCCGGTAA TGTAAATATT ACAGCGAGCG
2901 GCAATACACT TAAGGTAAGT AATATCACTG GTCAAGATGT AACAGTAACA
2951 GCGGATGCAG GAGCCTTGAC AACTACAGCA GGCTCAACCA TTAGTGCGAC
3001 AACAGGCAAT GCAAATATTA CAACCAAAAC AGGTGATATC AACGGTAAAG
3051 TTGAATCCAG CTCCGGCTCT GTAACACTTG TTGCAACTGG AGCAACTCTT
3101 GCTGTAGGTA ATATTTCAGG TAACACTGTT ACTATTACTG CGGATAGCGG
3151 TAAATTAACC TCCACAGTAG GTTCTACAAT TAATGGGACT AATAGTGTAA
3201 CCACCTCAAG CCAATCAGGC GATATTGAAG GTACAATTTC TGGTAATACA
3251 GTAAATGTTA CAGCAAGCAC TGGTGATTTA ACTATTGGAA ATAGTGCAAA
```

FIG. 8E.

| | | | | | |
|---|---|---|---|---|---|
| 3301 | AGTTGAAGCG | AAAAATGGAG | CTGCAACCTT | AACTGCTGAA | TCAGGCAAAT |
| 3351 | TAACCACCCA | AACAGGCTCT | AGCATTACCT | CAAGCAATGG | TCAGACAACT |
| 3401 | CTTACAGCCA | AGGATAGCAG | TATCGCAGGA | AACATTAATG | CTGCTAATGT |
| 3451 | GACGTTAAAT | ACCACAGGCA | CTTTAACTAC | TACAGGGGAT | TCAAAGATTA |
| 3501 | ACGCAACCAG | TGGTACCTTA | ACAATCAATG | CAAAAGATGC | CAAATTAGAT |
| 3551 | GGTGCTGCAT | CAGGTGACCG | CACAGTAGTA | AATGCAACTA | ACGCAAGTGG |
| 3601 | CTCTGGTAAC | GTGACTGCGA | AAACCTCAAG | CAGCGTGAAT | ATCACCGGGG |
| 3651 | ATTTAAACAC | AATAAATGGG | TTAAATATCA | TTTCGGAAAA | TGGTAGAAAC |
| 3701 | ACTGTGCGCT | TAAGAGGCAA | GGAAATTGAT | GTGAAATATA | TCCAACCAGG |
| 3751 | TGTAGCAAGC | GTAGAAGAGG | TAATTGAAGC | GAAACGCGTC | CTTGAGAAGG |
| 3801 | TAAAAGATTT | ATCTGATGAA | GAAAGAGAAA | CACTAGCCAA | ACTTGGTGTA |
| 3851 | AGTGCTGTAC | GTTTCGTTGA | GCCAAATAAT | GCCATTACGG | TTAATACACA |
| 3901 | AAACGAGTTT | ACAACCAAAC | CATCAAGTCA | AGTGACAATT | TCTGAAGGTA |
| 3951 | AGGCGTGTTT | CTCAAGTGGT | AATGGCGCAC | GAGTATGTAC | CAATGTTGCT |
| 4001 | GACGATGGAC | AGCAGTAGTC | AGTAATTGAC | AAGGTAGATT | TCATCCTGCA |
| 4051 | ATGAAGTCAT | TTTATTTTCG | TATTATTTAC | TGTGTGGGTT | AAAGTTCAGT |

FIG. 8F.

4101 ACGGGCTTTA CCCACCTTGT AAAAAATTAC GAAAAATACA ATAAAGTATT
4151 TTTAACAGGT TATTATTATG AAAAACATAA AAAGCAGATT AAAACTCAGT
4201 GCAATATCAA TATTGCTTGG CTTGGCTTCT TCATCGACGT ATGCAGAAGA
4251 AGCGTTTTTA GTAAAAGGCT TTCAGTTATC TGGCGCG

FIG. 9A.

```
  1 GGGAATGAGC GTCGTACACG GTACAGCAAC CATGCAAGTA GACGGCAATA
 51 AAACCACTAT CCGTAATAGC GTCAATGCTA TCATCAATTG GAAACAATTT
101 AACATTGACC AAAATGAAAT GGAGCAGTTT TTACAAGAAA GCAGCAACTC
151 TGCCGTTTTC AACCGTGTTA CATCTGACCA AATCTCCCAA TTAAAAGGGA
201 TTTTAGATTC TAACGGACAA GTCTTTTTAA TCAACCCAAA TGGTATCACA
251 ATAGGTAAAG ACGCAATTAT TAACACTAAT GGCTTTACTG CTTCTACGCT
301 AGACATTTCT AACGAAAACA TCAAGGCGCG TAATTTCACC CTTGAGCAAA
351 CCAAGGATAA AGCACTCGCT GAAATCGTGA ATCACGGTTT AATTACCGTT
401 GGTAAAGACG GTAGCGTAAA CCTTATTGGT GGCAAAGTGA AAAACGAGGG
451 CGTGATTAGC GTAAATGGCG GTAGTATTTC TTTACTTGCA GGGCAAAAAA
501 TCACCATCAG CGATATAATA AATCCAACCA TCACTTACAG CATTGCTGCA
551 CCTGAAAACG AAGCGATCAA TCTGGGCGAT ATTTTTGCCA AAGGTGGTAA
601 CATTAATGTC CGCGCTGCCA CTATTCGCAA TAAAGGTAAA CTTTCTGCCG
651 ACTCTGTAAG CAAAGATAAA AGTGGTAACA TTGTTCTCTC TGCCAAAGAA
701 GGTGAAGCGG AAATTGGCGG TGTAATTTCC GCTCAAAATC AGCAAGCCAA
751 AGGTGGTAAG TTGATGATTA CAGGTGATAA AGTCACATTA AAAACAGGTG
```

FIG. 9B.

```
 801  CAGTTATCGA CCTTTCAGGT AAAGAAGGGG GAGAGACTTA TCTTGGCGGT
 851  GATGAGCGTG GCGAAGGTAA AAATGGTATT CAATTAGCGA AGAAAACCTC
 901  TTTAGAAAAA GGCTCGACAA TTAATGTATC AGGCAAAGAA AAAGGCGGGC
 951  GCGCTATTGT ATGGGGCGAT ATTGCATTAA TTAATGGTAA CATTAATGCT
1001  CAAGGTAGCG ATATTGCTAA AACTGGCGGC TTTGTGGAAA CATCAGGACA
1051  TGACTTATCC ATTGGTGATG ATGTGATTGT TGACGCTAAA GAGTGGTTAT
1101  TAGACCCAGA TGATGTGTCC ATTGAAACTC TTACATCTGG ACGCAATAAT
1151  ACCGGCGAAA ACCAAGGATA TACAACAGGA GATGGGACTA AAGAGTCACC
1201  TAAAGGTAAT AGTATTTCTA AACCTACATT AACAAACTCA ACTCTTGAGC
1251  AAATCCTAAG AAGAGGTTCT TATGTTAATA TCACTGCTAA TAATAGAATT
1301  TATGTTAATA GCTCCATCAA CTTATCTAAT GGCAGTTTAA CACTTCACAC
1351  TAAACGAGAT GGAGTTAAAA TTAACGGTGA TATTACCTCA AACGAAAATG
1401  GTAATTTAAC CATTAAAGCA GGCTCTTGGG TTGATGTTCA TAAAAACATC
1451  ACGCTTGGTA CGGGTTTTTT GAATATTGTC GCTGGGGATT CTGTAGCTTT
1501  TGAGAGAGAG GGCGATAAAG CACGTAACGC AACAGATGCT CAAATTACCG
1551  CACAAGGGAC GATAACCGTC AATAAAGATG ATAAACAATT TAGATTCAAT
1601  AATGTATCTA TTAACGGGAC GGGCAAGGGT TTAAAGTTTA TTGCAAATCA
```

FIG. 9C.

| | | | | | |
|---|---|---|---|---|---|
| 1651 | AAATAATTTC | ACTCATAAAT | TTGATGGCGA | AATTAACATA | TCTGGAATAG |
| 1701 | TAACAATTAA | CCAAACCACG | AAAAAAGATG | TTAAATACTG | GAATGCATCA |
| 1751 | AAAGACTCTT | ACTGGAATGT | TTCTTCTCTT | ACTTTGAATA | CGGTGCAAAA |
| 1801 | ATTTACCTTT | ATAAAATTCG | TTGATAGCGG | CTCAAATTCC | CAAGATTTGA |
| 1851 | GGTCATCACG | TAGAAGTTTT | GCAGGCGTAC | ATTTTAACGG | CATCGGAGGC |
| 1901 | AAAACAAACT | TCAACATCGG | AGCTAACGCA | AAAGCCTTAT | TTAAATTAAA |
| 1951 | ACCAAACGCC | GCTACAGACC | CAAAAAAAGA | ATTACCTATT | ACTTTTAACG |
| 2001 | CCAACATTAC | AGCTACCGGT | AACAGTGATA | GCTCTGTGAT | GTTTGACATA |
| 2051 | CACGCCAATC | TTACCTCTAG | AGCTGCCGGC | ATAAACATGG | ATTCAATTAA |
| 2101 | CATTACCGGC | GGGCTTGACT | TTTCCATAAC | ATCCCATAAT | CGCAATAGTA |
| 2151 | ATGCTTTTGA | AATCAAAAAA | GACTTAACTA | TAAATGCAAC | TGGCTCGAAT |
| 2201 | TTTAGTCTTA | AGCAAACGAA | AGATTCTTTT | TATAATGAAT | ACAGCAAACA |
| 2251 | CGCCATTAAC | TCAAGTCATA | ATCTAACCAT | TCTTGGCGGC | AATGTCACTC |
| 2301 | TAGGTGGGGA | AAATTCAAGC | AGTAGCATTA | CGGGCAATAT | CAATATCACC |
| 2351 | AATAAAGCAA | ATGTTACATT | ACAAGCTGAC | ACCAGCAACA | GCAACACAGG |
| 2401 | CTTGAAGAAA | AGAACTCTAA | CTCTTGGCAA | TATATCTGTT | GAGGGGAATT |

FIG. 9D.

| | | | | | |
|---|---|---|---|---|---|
| 2451 | TAAGCCTAAC | TGGTGCAAAT | GCAAACATTG | TCGGCAATCT | TTCTATTGCA |
| 2501 | GAAGATTCCA | CATTTAAAGG | AGAAGCCAGT | GACAACCTAA | ACATCACCGG |
| 2551 | CACCTTTACC | AACAACGGTA | CCGCCAACAT | TAATATAAAA | CAAGGAGTGG |
| 2601 | TAAAACTCCA | AGGCGATATT | ATCAATAAAG | GTGGTTTAAA | TATCACTACT |
| 2651 | AACGCCTCAG | GCACTCAAAA | AACCATTATT | AACGGAAATA | TAACTAACGA |
| 2701 | AAAAGGCGAC | TTAAACATCA | AGAATATTAA | AGCCGACGCC | GAAATCCAAA |
| 2751 | TTGGCGGCAA | TATCTCACAA | AAAGAAGGCA | ATCTCACAAT | TTCTTCTGAT |
| 2801 | AAAGTAAATA | TTACCAATCA | GATAACAATC | AAAGCAGGCG | TTGAAGGGGG |
| 2851 | GCGTTCTGAT | TCAAGTGAGG | CAGAAAATGC | TAACCTAACT | ATTCAAACCA |
| 2901 | AAGAGTTAAA | ATTGGCAGGA | GACCTAAATA | TTTCAGGCTT | TAATAAAGCA |
| 2951 | GAAATTACAG | CTAAAAATGG | CAGTGATTTA | ACTATTGGCA | ATGCTAGCGG |
| 3001 | TGGTAATGCT | GATGCTAAAA | AAGTGACTTT | TGACAAGGTT | AAAGATTCAA |
| 3051 | AAATCTCGAC | TGACGGTCAC | AATGTAACAC | TAAATAGCGA | AGTGAAAACG |
| 3101 | TCTAATGGTA | GTAGCAATGC | TGGTAATGAT | AACAGCACCG | GTTTAACCAT |
| 3151 | TTCCGCAAAA | GATGTAACGG | TAAACAATAA | CGTTACCTCC | CACAAGACAA |
| 3201 | TAAATATCTC | TGCCGCAGCA | GGAAATGTAA | CAACCAAAGA | AGGCACAACT |
| 3251 | ATCAATGCAA | CCACAGGCAG | CGTGGAAGTA | ACTGCTCAAA | ATGGTACAAT |

FIG. 9E.

3301 TAAAGGCAAC ATTACCTCGC AAAATGTAAC AGTGACAGCA ACAGAAAATC
3351 TTGTTACCAC AGAGAATGCT GTCATTAATG CAACCAGCGG CACAGTAAAC
3401 ATTAGTACAA AAACAGGGGA TATTAAAGGT GGAATTGAAT CAACTTCCGG
3451 TAATGTAAAT ATTACAGCGA GCGGCAATAC ACTTAAGGTA AGTAATATCA
3501 CTGGTCAAGA TGTAACAGTA ACAGCGGATG CAGGAGCCTT GACAACTACA
3551 GCAGGCTCAA CCATTAGTGC GACAACAGGC AATGCAAATA TTACAACCAA
3601 AACAGGTGAT ATCAACGGTA AAGTTGAATC CAGCTCCGGC TCTGTAACAC
3651 TTGTTGCAAC TGGAGCAACT CTTGCTGTAG GTAATATTTC AGGTAACACT
3701 GTTACTATTA CTGCGGATAG CGGTAAATTA ACCTCCACAG TAGGTTCTAC
3751 AATTAATGGG ACTAATAGTG TAACCACCTC AAGCCAATCA GGCGATATTG
3801 AAGGTACAAT TTCTGGTAAT ACAGTAAATG TTACAGCAAG CACTGGTGAT
3851 TTAACTATTG GAAATAGTGC AAAAGTTGAA GCGAAAAATG GAGCTGCAAC
3901 CTTAACTGCT GAATCAGGCA AATTAACCAC CCAAACAGGC TCTAGCATTA
3951 CCTCAAGCAA TGGTCAGACA ACTCTTACAG CCAAGGATAG CAGTATCGCA
4001 GGAAACATTA ATGCTGCTAA TGTGACGTTA AATACCACAG GCACTTTAAC
4051 TACTACAGGG GATTCAAAGA TTAACGCAAC CAGTGGTACC TTAACAATCA

FIG. 9F.

```
4101  ATGCAAAAGA TGCCAAATTA GATGGTGCTG CATCAGGTGA CCGCACAGTA
4151  GTAAATGCAA CTAACGCAAG TGGCTCTGGT AACGTGACTG CGAAAACCTC
4201  AAGCAGCGTG AATATCACCG GGGATTTAAA CACAATAAAT GGGTTAAATA
4251  TCATTTCGGA AAATGGTAGA AACACTGTGC GCTTAAGAGG CAAGGAAATT
4301  GATGTGAAAT ATATCCAACC AGGTGTAGCA AGCGTAGAAG AGGTAATTGA
4351  AGCGAAACGC GTCCTTGAGA AGGTAAAAGA TTTATCTGAT GAAGAAAGAG
4401  AAACACTAGC CAAACTTGGT GTAAGTGCTG TACGTTTCGT TGAGCCAAAT
4451  AATGCCATTA CGGTTAATAC ACAAAACGAG TTTACAACCA AACCATCAAG
4501  TCAAGTGACA ATTTCTGAAG GTAAGGCGTG TTTCTCAAGT GGTAATGGCG
4551  CACGAGTATG TACCAATGTT GCTGACGATG GACAGCAGTA GTCAGTAATT
4601  GACAAGGTAG ATTTCATCCT GCAATGAAGT CATTTTATTT TCGTATTATT
4651  TACTGTGTGG GTTAAAGTTC AGTACGGGCT TTACCCACCT TGTAAAAAAT
4701  TA
```

FIG. 10A. COMPARISON OF DERIVED AMINO ACID SEQUENCE

| | 1 | | | | 50 |
|---|---|---|---|---|---|
| Hmw3com | .......... | .......... | .......... | .......... | .......... |
| Hmw4com | .......... | .......... | .......... | .......... | .......... |
| Hmw1com | MNKIYRLKFS | KRLNALVAVS | ELARGCDHST | EKGSEKPARM | KVRHLALKPL |
| Hmw2com | MNKIYRLKFS | KRLNALVAVS | ELARGCDHST | EKGSEKPARM | KVRHLALKPL |

| | 51 | | | | 100 |
|---|---|---|---|---|---|
| Hmw3com | .......... | .......... | .......... | .......... | .......... |
| Hmw4com | .......... | .......... | ..GMSVVHGT | ATMQVDGNKT | TIRNSVNAII |
| Hmw1com | SAMLLSLGVT | SIPQSVLASG | LQGMSVVHGT | ATMQVDGNKT | TIRNSVNAII |
| Hmw2com | SAMLLSLGVT | SIPQSVLASG | LQGMSVVHGT | ATMQVDGNKT | TIRNSVNAII |

| | 101 | | | | 150 |
|---|---|---|---|---|---|
| Hmw3com | .......... | .......... | .......... | .......... | .......... |
| Hmw4com | NWKQFNIDQN | EMEQFLQESS | NSAVFNRVTS | DQISQLKGIL | DSNGQVFLIN |

FIG. 10B.

```
Hmw1com   NWKQFNIDQN EMVQFLQENN NSAVFNRVTS NQISQLKGIL DSNGQVFLIN
Hmw2com   NWKQFNIDQN EMVQFLQENN NSAVFNRVTS NQISQLKGIL DSNGQVFLIN

           151                                              200
Hmw3com   .......... .......... .......... .......... ..........
Hmw4com   PNGITIGKDA IINTNGFTAS TLDISNENIK ARNFTLEQTK DKALAEIVNH
Hmw1com   PNGITIGKDA IINTNGFTAS TLDISNENIK ARNFTLEQTK DKALAEIVNH
Hmw2com   PNGITIGKDA IINTNGFTAS TLDISNENIK ARNFTLEQTK DKALAEIVNH

           201                                              250
Hmw3com   .......... .......... .......... .......... ..........
Hmw4com   GLITVGKDGS VNLIGGKVKN EGVISVNGGS ISLLAGQKIT ISDIINPTIT
Hmw1com   GLITVGKDGS VNLIGGKVKN EGVISVNGGS ISLLAGQKIT ISDIINPTIT
Hmw2com   GLITVGKDGS VNLIGGKVKN EGVISVNGGS ISLLAGQKIT ISDIINPTIT

           251                                              300
Hmw3com   .......... INLGDIFAKG GNINVRAATI RNKGKLSADS VSKDKSGNIV
```

FIG. 10C.

```
Hmw4com   YSIAAPENEA INLGDIFAKG GNINVRAATI RNKGKLSADS VSKDKSGNIV
Hmw1com   YSIAAPENEA VNLGDIFAKG GNINVRAATI RNKGKLSADS VSKDKSGNIV
Hmw2com   YSIAAPENEA VNLGDIFAKG GNINVRAATI RNKGKLSADS VSKDKSGNIV

          301                                                350
Hmw3com   LSAKEGEAEI GGVISAQNQQ AKGGKLMITG DKVTLKTGAV IDLSGKEGGE
Hmw4com   LSAKEGEAEI GGVISAQNQQ AKGGKLMITG DKVTLKTGAV IDLSGKEGGE
Hmw1com   LSAKEGEAEI GGVISAQNQQ AKGGKLMITG DKVTLKTGAV IDLSGKEGGE
Hmw2com   LSAKEGEAEI GGVISAQNQQ AKGGKLMITG DKVTLKTGAV IDLSGKEGGE

          351                                                400
Hmw3com   TYLGGDERGE GKNGIQLAKK TTLEKGSTIN VSGKEKGGRA IVWGDIALID
Hmw4com   TYLGGDERGE GKNGIQLAKK TTLEKGSTIN VSGKEKGGRA IVWGDIALID
Hmw1com   TYLGGDERGE GKNGIQLAKK TTLEKGSTIN VSGKEKGGRA IVWGDIALID
Hmw2com   TYLGGDERGE GKNGIQLAKK TTLEKGSTIN VSGKEKGGRA IVWGDIALID
```

FIG. 10D.

```
           401                                                    450
Hmw3com    GNINAQGK.D IAKTGGFVET SGHYLSIDDN AIVKTKEWLL DPENVTIEAP
Hmw4com    GNINAQGS.D IAKTGGFVET SGHDLSIGDD VIVDAKEWLL DPDDVSIETL
Hmw1com    GNINAQGSGD IAKTGGFVET SGHDLFIKDN AIVDAKEWLL DPDNVTINAE
Hmw2com    GNINAQGSGD IAKTGGFVET SGHYLSIESN AIVKTKEWLL DPDDVTIEAE

           451                                                    500
Hmw3com    SASRVELGAD RNSHSAEVIK VTLKKNNTSL TTLTNTTISN LLKSAHVVNI
Hmw4com    TSGRNNTGEN QGYTTGDGTK ESPKGNSISK PTLTNSTLEQ ILRRGSYVNI
Hmw1com    TAGRSNTSED DEYTGSGNSA STPKRNKE.K TTLTNTTLES ILKKGTFVNI
Hmw2com    DPLRNNTGIN DEFPTGTGEA SDPKKNSELK TTLTNTTISN YLKNAWTMNI

           501                                                    550
Hmw3com    TARRKLTVNS SISIERGSHL ILHSEGQGGQ GVQIDKDITS .E...GGNLT
Hmw4com    TANNRIYVNS SINLSNGS.L TLHTK...RD GVKINGDITS NE...NGNLT
Hmw1com    TANQRIYVNS SINL.SNGSL TLWSEGRSGG GVEINNDITT GDDTRGANLT
Hmw2com    TASRKLTVNS SINGSNGSHL ILHSKGQRGG GVQIDGDIT. ...SKGGNLT
```

FIG.10E.

```
           551                                                600
Hmw3com    IYSGGWVDVH KNITLGS.GF LNITTKEGDI AFEDKSGR.. ..NNLTITAQ
Hmw4com    IKAGSWVDVH KNITLGT.GF LNIVAGDS.V AFEREGDKAR NATDAQITAQ
Hmw1com    IYSGGWVDVH KNISLGAQGN INITAKQD.I AFEKGSNQV. ......ITGQ
Hmw2com    IYSGGWVDVH KNITLD.QGF LNITA.AS.V AFEGGNNKAR DANNLTITAQ

           601                                                650
Hmw3com    GTITSG.NSN GFRFNNVSLN SLGGKLSFTD SREDRGRRTK GNISNKFDGT
Hmw4com    GTITVNKDDK QFRFNNVSIN GTGKGLKFIA NQN....... .NFTHKFDGE
Hmw1com    GTIT.SGNQK GFRFNNVSLN GTGSGLQFTT KRTN.....K YAITNKFEGT
Hmw2com    GTVTITGEGK DFRANNVSLN GTGKGLNIIS SVNN...... ..LTHNLSGT

           651                                                700
Hmw3com    LNISGTVDIS MKAPKVSWFY RD.KGRTYWN VTTLNVTSGS KFNLSIDSTG
Hmw4com    INISGIVTIN QTTKKDVKYW NA.SKDSYWN VSSLTLNTVQ KFTF.IKFVD
Hmw1com    LNISGKVNIS MVLPKNESGY DKFKGRTYWN LTSLNVSESG EFNLTIDSRG
```

FIG. 10F.

```
Hmw2com   INISGNITIN QTTRKNTSYW QTSHD.SHWN VSALNLETGA NFTF.IKYIS

          701                                              750
Hmw3com   SGSTG...PS IRNA..ELNG ITFN....KA TFNIAQGSTA NFSIKASIMP
Hmw4com   SGSNS...QD LRSSRRSFAG VHFNGIGGKT NFNIGANAKA LFKLKPNAAT
Hmw1com   SDSAGTLTQ. ....PYNLNG ISFN...KDT TFNVERNARV NFDIKAPIGI
Hmw2com   SNSKGLTTQY RSSAGVNFNG V..N...GNM SFNLKEGAKV NFKLKPNENM

          751                                              800
Hmw3com   FKSNANYAL. FNEDISVSG. .GGSVNFKLN ASSSNIQTPG VIIKSQNFNV
Hmw4com   DPKKELPIT. FNANITATGN SDSSVMFDIH A...NLTSRA AGINMDSINI
Hmw1com   NKYSSLNYAS FNGNISVSG. .GGSVDFTLL ASSSNVQTPG VVINSKYFNV
Hmw2com   NTSKPLPI.R FLANITATG. .GGSVFFDIY ANHS...GRG AELKMSEINI

          801                                              850
Hmw3com   SGGSTLNLKA EGSTETAFSI ENDLNLNATG GNITIRQVEG T..DSRVNKG
Hmw4com   TGGLDFSITS HNRNSNAFEI KKDLTINATG SNFSLKQTKD SFYNEYSKHA
```

FIG. 10G.

```
Hmw1com  STGSSLRFKT SGSTKTGFSI EKDLTLNATG GNITLLQVEG T..DGMIGKG
Hmw2com  SNGANFTLNS HVRGDDAFKI NKDLTINATN SNFSLRQTKD DFYDGYARNA

         851                                               900
Hmw3com  VAAKKNITFK GGNITFGSQK ATTEIKGNVT INKNTNATLR GANFAEN...
Hmw4com  INSSHNLTIL GGNVTLGGEN SSSSITGNIN ITNKANVTLQ ADTSNSNTGL
Hmw1com  IVAKKNITFE GGNITFGSRK AVTEIEGNVT INNNANVTLI GSDFDNHQ..
Hmw2com  INSTYNISIL GGNVTLGGQN SSSSITGNIT IEKAANVTLE ANNAPNQQNI

         901                                               950
Hmw3com  KSPLNIAGNV INNGNLTTAG SIINIAGNLT VSKGANLQAI TNYTFNVAGS
Hmw4com  KKRTLTLGNI SVEGNLSLTG ANANIVGNLS IAEDSTFKGE ASDNLNITGT
Hmw1com  KPLTIKKDVI INSGNLTAGG NIVNIAGNLT VESNANFKAI TNFTFNVGGL
Hmw2com  RDRVIKLGSL LVNGSLSLTG ENADIKGNLT ISESATFKGK TRDTLNITGN

         951                                              1000
```

FIG. 10H.

```
Hmw3com   FDNNGASNIS IARGGAKFK. DINNTSSLNI TTNSDTTYRT IIKGNISNKS
Hmw4com   FTNNGTANIN IKQGVVKLQG DINNKGGLNI TTNASGTQKT IINGNITNEK
Hmw1com   FDNKGNSNIS IAKGGARFK. DIDNSKNLSI TTNSSSTYRT IISGNITNKN
Hmw2com   FTNNGTAEIN ITQGVVKLG. NVTNDGDLNI TTHAKRNQRS IIGGDIINNK

          1001                                              1050
Hmw3com   GDLNIIDKKS DAEIQIGGNI SQKEGNLTIS SDKVNITNQI TIKAGVEGGR
Hmw4com   GDLNIKNIKA DAEIQIGGNI SQKEGNLTIS SDKVNITNQI TIKAGVEGGR
Hmw1com   GDLNITNEGS DTEMQIGGDI SQKEGNLTIS SDKINITKQI TIKAGVDGEN
Hmw2com   GSLNITDSNN DAEIQIGGNI SQKEGNLTIS SDKINITKQI TIKKGIDGED

          1051                                              1100
Hmw3com   SDSSEAENAN LTIQTKELKL AGDLNISGFN KAEITAKNGS DLTIGNASGG
Hmw4com   SDSSEAENAN LTIQTKELKL AGDLNISGFN KAEITAKNGS DLTIGNASGG
Hmw1com   SDSDATNNAN LTIKTKELKL TQDLNISGFN KAEITAKDGS DLTIGNTNSA
Hmw2com   SSSDATSNAN LTIKTKELKL TEDLSISGFN KAEITAKDGR DLTIGNSNDG
```

FIG. 10I.

```
                1101                                                  1150
Hmw3com   N..ADAKKVT FDKVKDSKIS TDGHNVTLNS EVKT..SNGS SNAGNDNSTG
Hmw4com   N..ADAKKVT FDKVKDSKIS TDGHNVTLNS EVKT..SNGS SNAGNDNSTG
Hmw1com   D.GTNAKKVT FNQVKDSKIS ADGHKVTLHS KVETSGSNNN TEDSSDNNAG
Hmw2com   NSGAEAKKVT FNNVKDSKIS ADGHNVTLNS KVKTSSSNGG RESNSDNDTG

                1151                                                  1200
Hmw3com   LTISAKDVTV NNNVTSHKTI NISAAAGNVT TKEGTTINAT TGSVEVTAQN
Hmw4com   LTISAKDVTV NNNVTSHKTI NISAAAGNVT TKEGTTINAT TGSVEVTAQN
Hmw1com   LTIDAKNVTV NNNITSHKAV SISATSGEIT TKTGTTINAT TGNVEIT...
Hmw2com   LTITAKNVEV NKDVTSLKTV NITA.SEKVT TTAGSTINAT NGKASIT...

                1201                                                  1250
Hmw3com   GTIKGNITSQ NVTVTATENL VTTENAVINA TSGTVNISTK TGDIKGGIES
Hmw4com   GTIKGNITSQ NVTVTATENL VTTENAVINA TSGTVNISTK TGDIKGGIES
Hmw1com   .......... .......... .......... ........AQ TGDIKGGIES
```

FIG. 10J.

```
Hmw2com   .......... .......... .......... ........TK T.........

          1251                                             1300
Hmw3com   TSGNVNITAS GNTLKVSNIT GQDVTVTADA GALTTTAGST ISATTGNANI
Hmw4com   TSGNVNITAS GNTLKVSNIT GQDVTVTADA GALTTTAGST ISATTGNANI
Hmw1com   SSGSVTLTAT EGALAVSNIS GNTVTVTANS GALTTLAGST IKG.TESVTT
Hmw2com   .......... .......... .......... .......... ..........

          1301                                             1350
Hmw3com   TTKTGDINGK VESSSGSVTL VATGATLAVG NISGNTVTIT ADSGKLTSTV
Hmw4com   TTKTGDINGK VESSSGSVTL VATGATLAVG NISGNTVTIT ADSGKLTSTV
Hmw1com   SSQSGDIG.. .......... .........G TISGGTVEVK ATESLTTQSN
Hmw2com   ....GDIS.. .......... .........G TISGNTVSVS ATVDLTTKSG

          1351                                             1400
Hmw3com   GSTINGTNSV TTSSQSGDIE GTISGNTVNV TASTGDLTIG NSAKVEAKNG
Hmw4com   GSTINGTNSV TTSSQSGDIE GTISGNTVNV TASTGDLTIG NSAKVEAKNG
```

FIG. 10K.

```
Hmw1com   SKIKATTGEA NVTSATGTIG GTISGNTVNV TANAGDLTVG NGAEINATEG
Hmw2com   SKIEAKSGEA NVTSATGTIG GTISGNTVNV TANAGDLTVG NGAEINATEG

          1401                                             1450
Hmw3com   AATLTAESGK LTTQTGSSIT SSNGQTTLTA KDSSIAGNIN AANVTLNTTG
Hmw4com   AATLTAESGK LTTQTGSSIT SSNGQTTLTA KDSSIAGNIN AANVTLNTTG
Hmw1com   AATLTTSSGK LTTEASSHIT SAKGQVNLSA QDSSVAGSIN AANVTLNTTG
Hmw2com   AATLTATGNT LTTEAGSSIT STKGQVDLLA QNSSIAGNIN AANVTLNTTG

          1451                                             1500
Hmw3com   TLTTTGDSKI NATSGTLTIN AKDAKLDGAA SGDRTVVNAT NASGSGNVTA
Hmw4com   TLTTTGDSKI NATSGTLTIN AKDAKLDGAA SGDRTVVNAT NASGSGNVTA
Hmw1com   TLTTVKGSNI NATSGTLTIN AKDAELNGAA LGNHTVVNAT NANGSGSVIA
Hmw2com   TLTTVAGSDI KATSGTLTIN AKDAKLNGDA SGDSTEVNAV NASGSGSVTA

          1501                                             1550
```

FIG. 10L.

```
Hmw3com   KTSSSVNITG DLNTINGLNI ISENGRNTVR LRGKEIDVKY IQPGVASVEE
Hmw4com   KTSSSVNITG DLNTINGLNI ISENGRNTVR LRGKEIDVKY IQPGVASVEE
Hmw1com   TTSSRVNITG DLITINGLNI ISKNGINTVL LKGVKIDVKY IQPGIASVDE
Hmw2com   ATSSSVNITG DLNTVNGLNI ISKDGRNTVR LRGKEIEVKY IQPGVASVEE

           1551                                         1600
Hmw3com   VIEAKRVLEK VKDLSDEERE TLAKLGVSAV RFVEPNNAIT VNTQNEFTTK
Hmw4com   VIEAKRVLEK VKDLSDEERE TLAKLGVSAV RFVEPNNAIT VNTQNEFTTK
Hmw1com   VIEAKRILEK VKDLSDEERE ALAKLGVSAV RFIEPNNTIT VDTQNEFATR
Hmw2com   VIEAKRVLEK VKDLSDEERE TLAKLGVSAV RFVEPNNTIT VNTQNEFTTR

           1601                          1632
Hmw3com   PSSQVTISEG KACFSSGNGA RVCTNVADDG QQ
Hmw4com   PSSQVTISEG KACFSSGNGA RVCTNVADDG QQ
Hmw1com   PLSRIVISEG RACFSNSDGA TVCVNIADNG R.
Hmw2com   PSSQVIISEG KACFSSGNGA RVCTNVADDG QP
```

HIGH MOLECULAR WEIGHT SURFACE PROTEINS OF NON-TYPEABLE HAEMOPHILUS

FIELD OF INVENTION

This invention relates to high molecular weight proteins of non-typeable haemophilus.

BACKGROUND TO THE INVENTION

Non-typeable *Haemophilus influenzae* are non-encapsulated organisms that are defined by their lack of reactivity with antisera against known *H. influenzae* capsular antigens.

These organisms commonly inhabit the upper respiratory tract of humans and are frequently responsible for infections, such as otitis media, sinusitis, conjunctivitis, bronchitis and pneumonia. Since these organisms do not have a polysaccharide capsule, they are not controlled by the present *Haemophilus influenzae* type b (Hib) vaccines, which are directed towards Hib bacterial capsular polysaccharides. The non-typeable strains, however, do produce surface antigens that can elicit bactericidal antibodies. Two of the major outer membrane proteins, P2 and P6, have been identified as targets of human serum bactericidal activity. However, it has been shown that the P2 protein sequence is variable, in particular in the non-typeable Haemophilus strains. Thus, a P2-based vaccine would not protect against all strains of the organism.

There have previously been identified by Barenkamp et al (*Pediatr. Infect. Dis. J.*, 9:333–339, 1990) a group of high-molecular-weight (HMW) proteins that appeared to be major targets of antibodies present in human convalescent sera. Examination of a series of middle ear isolates revealed the presence of one or two such proteins in most strains. However, prior to the present invention, the structures of these proteins were unknown as were pure isolates of such proteins.

SUMMARY OF INVENTION

The inventors, in an effort to further characterize the high molecular weight (HMW) Haemophilus proteins, have cloned, expressed and sequenced the genes coding for two immunodominant HMW proteins (designated HMW1 and HMW2) from a prototype non-typeable Haemophilus strain and have cloned, expressed and almost completely sequenced the genes coding for two additional immunodominant HMW proteins (designated HMW3 and HMW4) from another non-typeable Haemophilus strain.

In accordance with one aspect of the present invention, therefore, there is provided an isolated and purified gene coding for a high molecular weight protein of a non-typeable Haemophilus strain, particularly a gene coding for protein HMW1, HMW2, HMW3 or HMW4, as well as any variant or fragment of such protein which retains the immunological ability to protect against disease caused by a non-typeable *Haemophilus* strain. In another aspect, the invention provides a high molecular weight protein of non-typeable *Haemophilus influenzae* which is encoded by these genes.

BRIEF DESCRIPTION OF DRAWINGS

FIG. 1 is a DNA sequence of a gene coding for protein HMW1 (SEQ ID NO: 1);

FIG. 2 is a derived amino acid sequence of protein HMW1 (SEQ ID NO: 2);

FIG. 3 is a DNA sequence of a gene coding for protein HMW2 (SEQ ID NO: 3);

FIG. 4 is a derived amino acid sequence of HMW2 (SEQ ID NO: 4);

FIG. 5B shows the restriction map of the T7 expression vector pT7-7;

FIG. 6 contains the DNA sequence of a gene cluster for the hmw1 gene (SEQ ID NO: 5), comprising nucleotides 351 to 4958 (ORF a) (as in FIG. 1), as well as two additional downstream genes in the 3' flanking region, comprising ORFs b, nucleotides 5114–6748, and c nucleotides 7062–9011;

FIG. 7 contains the DNA sequence of a gene cluster for the hmw2 gene (SEQ ID NO: 6), comprising nucleotides 792 to 5222 (ORF a) (as in FIG. 3), as well as two additional downstream genes in the 3' flanking region, comprising ORFs b, nucleotides 5375–7009, and c, nucleotides 7249–9198;

FIG. 8 is a partial DNA sequence of a gene coding for protein HMW3 (SEQ ID NO: 7);

FIG. 9 is a partial DNA sequence of a gene coding for protein HMW4 (SEQ ID NO: 8); and FIG. 10 is a comparison table for the derived amino acid sequence for proteins HMW1, HMW2, HMW3 and HMW4.

GENERAL DESCRIPTION OF INVENTION

Figure 5A:
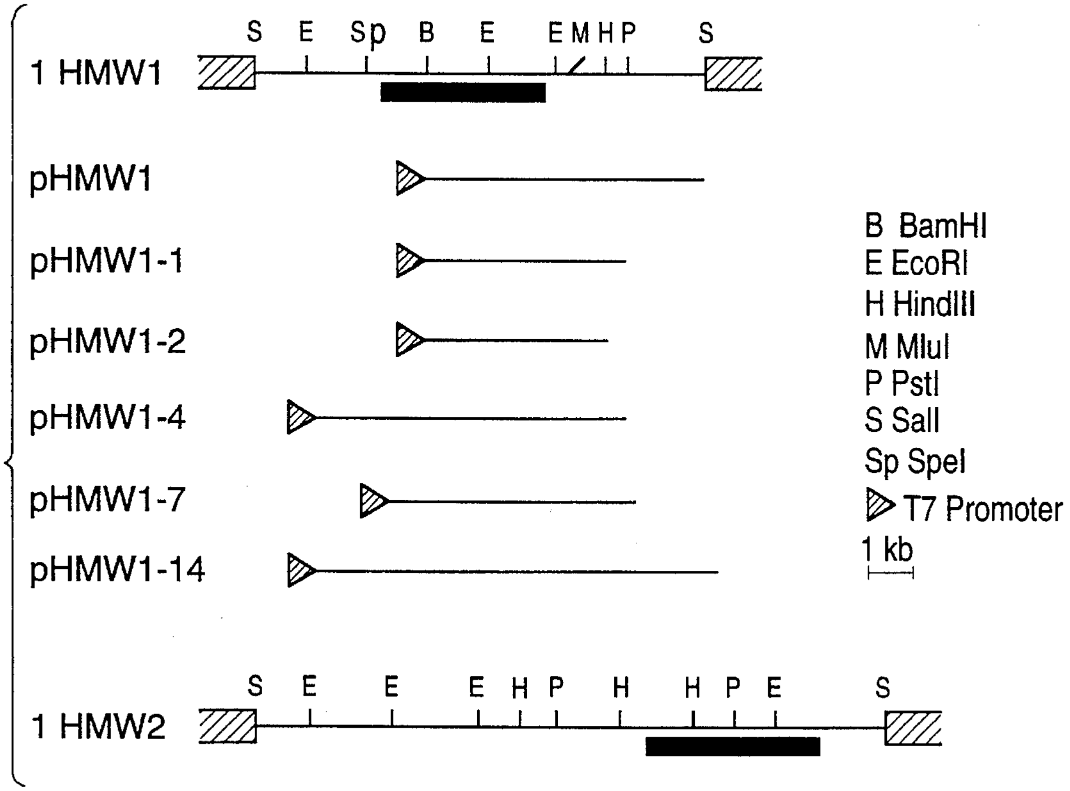
FIG. 5A shows restriction maps of representative recombinant phages which contained the HMW1 or HMW2 structural genes, the locations of the structural genes being indicated by the shaded bars.

The DNA sequences of the genes coding for HMW1 and HMW2, shown in FIGS. 1 and 3 respectively, were shown to be about 80% identical, with the first 1259 base pairs of the genes being identical. The derived amino acid sequences of the two HMW proteins, shown in FIGS. 2 and 4 respectively, are about 70% identical. Furthermore, the encoded proteins are antigenically related to the filamentous hemagglutinin surface protein of *Bordetella pertussis*. A monoclonal antibody prepared against filamentous hemagglutinin (FHA) of *Bordetella pertussis* was found to recognize both of the high molecular weight proteins. This data suggests that the HMW and FHA proteins may serve similar biological functions. The derived amino acid sequences of the HMW1 and HMW2 proteins show sequence similarity to that for the FHA protein. It has further been shown that these antigenically-related proteins are produced by the majority of the non-typeable strains of Haemophilus. Antisera raised against the protein expressed by the HMW1 gene recognizes both the HMW2 protein and the *B. pertussis* FHA. The present invention includes an isolated and purified high molecular weight protein of non-typeable haemophilus which is antigenically related to the *B. pertussis* FHA, which may be obtained from natural sources or produced recombinantly.

A phage genomic library of a known strain of non-typeable Haemophilus was prepared by standard methods and the library was screened for clones expressing high molecular weight proteins, using a high titre antiserum against HMW's. A number of strongly reactive DNA clones were plaque-purified and sub-cloned into a T7 expression plasmid. It was found that they all expressed either one or the other of the two high-molecular-weight proteins designated HMW1 and HMW2, with apparent molecular weights of 125 and 120 kDa, respectively, encoded by open reading frames of 4.6 kb and 4.4 kb, respectively.

Representative clones expressing either HMW1 and HMW2 were further characterized and the genes isolated, purified and sequenced. The DNA sequence of HMW1 is shown in FIG. 1 and the corresponding derived amino acid sequence in FIG. 2. Similarly, the DNA sequence of HMW2 is shown in FIG. 3 and the corresponding derived amino acid sequence in FIG. 4. Partial purification of the isolated proteins and N-terminal sequence analysis indicated that the expressed proteins are truncated since their sequence starts at residue number 442 of both full length HMW1 and HMW2 gene products.

Subcloning studies with respect to the hmw1 and hmw2 genes indicated that correct processing of the HMW proteins required the products of additional downstream genes. It has been found that both the hmw1 and hmw2 genes are flanked by two additional downstream open reading frames (ORFs), designated b and c, respectively, (see FIGS. 6 and 7).

The b ORFs are 1635 bp in length, extending from nucleotides 5114 to 6748 in the case of hmw1 and nucleotides 5375 to 7009 in the case of hmw2, with their derived amino acid sequences 99% identical. The derived amino acid sequences demonstrate similarity with the derived amino acid sequences of two genes which encode proteins required for secretion and activation of hemolysins of *P. mirabilis* and *S. marcescens.*

The c ORFs are 1950 bp in length, extending from nucleotides 7062 to 9011 in the case of hmw1 and nucleotides 7249 to 9198 in the case of hmw2, with their derived amino acid sequences 96% identical. The hmw1 c ORF is preceded by a series of 9 bp direct tandem repeats. In plasmid subclones, interruption of the hmw1 b or c ORF results in defective processing and secretion of the hmw1 structural gene product.

The two high molecular weight proteins have been isolated and purified and shown to be partially protective against otitis media in chinchillas and to function as adhesins. These results indicate the potential for use of such high molecular proteins and structurally-related proteins of other non-typeable strains of *Haemophilus influenzae* as components in non-typeable *Haemophilus influenzae* vaccines.

Since the proteins provided herein are good cross-reactive antigens and are present in the majority of non-typeable Haemophilus strains, it is evident that these HMW proteins may become integral constituents of a universal Haemophilus vaccine. Indeed, these proteins may be used not only as protective antigens against otitis, sinusitis and bronchitis caused by the non-typeable Haemophilus strains, but also may be used as carriers for the protective Hib polysaccharides in a conjugate vaccine against meningitis. The proteins also may be used as carriers for other antigens, haptens and polysaccharides from other organisms, so as to induce immunity to such antigens, haptens and polysaccharides.

The nucleotide sequences encoding two high molecular weight proteins of a different non-typeable Haemophilus strain (designated HMW3 and HMW4) have been largely elucidated, and are presented in FIGS. 8 and 9. HMW3 has an apparent molecular weight of 125 kDa while HMW4 has an apparent molecular weight of 123 kDa. These high molecular weight proteins are antigenically related to the HMW1 and HMW2 proteins and to FHA. Sequence analysis of HMW3 is approximately 85% complete and of HMW4 95% complete, with short stretches at the 5'-ends of each gene remaining to be sequenced.

FIG. 10 contains a multiple sequence comparison of the derived amino acid sequences for the four high molecular weight proteins identified herein. As may be seen from this comparison, stretches of identical peptide sequence may be found throughout the length of the comparison, with HMW3 more closely resembling HMW1 and HMW4 more closely resembling HMW2. This information is highly suggestive of a considerable sequence homology between high molecular weight proteins from various non-typeable Haemophilus strains.

In addition, mutants of non-typeable *H. influenzae* strains that are deficient in expression of HMW1 or HMW2 or both have been constructed and examined for their capacity to adhere to cultured human epithelial cells. The hmw1 and hmw2 gene clusters have been expressed in *E. coli* and have been examined for in vitro adherence. The results of such experimentation demonstrate that both HMW1 and HMW2 mediate attachment and hence are adhesins and that this function is present even in the absence of other *H. influenzae* surface structures.

With the isolation and purification of the high molecular weight proteins, the inventors are able to determine the major protective epitopes by conventional epitope mapping and synthesize peptides corresponding to these determinants to be incorporated in fully synthetic or recombinant vaccines. Accordingly, the invention also comprises a synthetic peptide having an amino acid sequence corresponding to at least one protective epitope of a high molecular weight protein of a non-typeable *Haemophilus influenzae*. Such peptides are of varying length that constitute portions of the high-molecular-weight proteins, that can be used to induce immunity, either directly or as part of a conjugate, against the relative organisms and thus constitute vaccines for protection against the corresponding diseases.

The present invention also provides any variant or fragment of the proteins that retains the potential immunological ability to protect against disease caused by non-typeable Haemophilus strains. The variants may be constructed by partial deletions or mutations of the genes and expression of the resulting modified genes to give the protein variations.

EXAMPLES

Example 1

Non-typeable *H.influenzae* strains 5 and 12 were isolated in pure culture from the middle ear fluid of children with acute otitis media. Chromosomal DNA from strain 12, providing genes encoding proteins HMW1 and HMW2, was prepared by preparing Sau3A partial restriction digests of chromosomal DNA and fractionating on sucrose gradients. Fractions containing DNA fragments in the 9 to 20 kbp range were pooled and a library was prepared by ligation into λEMBL3 arms. Ligation mixtures were packaged in vitro and plate-amplified in a P2 lysogen of *E. coli* LE392.

For plasmid subcloning studies, DNA from a representative recombinant phage was subcloned into the T7 expression plasmid pT7-7, containing the T7 RNA polymerase promoter Φ10, a ribosome-binding site and the translational start site for the T7 gene 10 protein upstream from a multiple cloning site (see FIG. 5B).

DNA sequence analysis was performed by the dideoxy method and both strands of the HMW1 gene and a single strand of the HMW2 gene were sequenced.

Western immunoblot analysis was performed to identify the recombinant proteins being produced by reactive phage clones. Phage lysates grown in LE392 cells or plaques picked directly from a lawn of LE392 cells on YT plates were solubilized in gel electrophoresis sample buffer prior to electrophoresis. Sodium dodecyl sulfate (SDS)-polyacrylamide gel electrophoresis was performed on 7.5% or 11% polyacrylamide modified Laemmli gels. After transfer of the proteins to nitrocellulose sheets, the sheets were probed sequentially with an *E. coli*-absorbed human serum sample containing high-titer antibody to the high-molecular-weight proteins and then with alkaline phosphatase-conjugated goat anti-human immunoglobulin G (IgG) second antibody. Sera from healthy adults contains high-titer antibody directed against surface-exposed high-molecular-weight proteins of non-typeable *H. influenzae*. One such serum sample was used as the screening antiserum after having been extensively absorbed with LE392 cells.

To identify recombinant proteins being produced by *E. coli* transformed with recombinant plasmids, the plasmids of interest were used to transform *E. coli* BL21 (DE3)/pLysS. The transformed strains were grown to an $A_{600}$ of 0.5 in L broth containing 50 μg of ampicillin per ml. IPTG was then added to 1 mM. One hour later, cells were harvested, and a sonicate of the cells was prepared. The protein concentrations of the samples were determined by the bicinchoninic acid method. Cell sonicates containing 100 μg of total protein were solubilized in electrophoresis sample buffer, subjected to SDS-polyacrylamide gel electrophoresis, and transferred to nitrocellulose. The nitrocellulose was then probed sequentially with the *E. coli*-absorbed adult serum sample and then with alkaline phosphatase-conjugated goat anti-human IgG second antibody.

Western immunoblot analysis also was performed to determine whether homologous and heterologous non-typeable *H. influenzae* strains expressed high-molecular-weight proteins antigenically related to the protein encoded by the cloned HMW1 gene (rHMW1). Cell sonicates of bacterial cells were solubilized in electrophoresis sample buffer, subjected to SDS-polyacrylamide gel electrophoresis, and transferred to nitrocellulose. Nitrocellulose was probed sequentially with polyclonal rabbit rHMW1 antiserum and then with alkaline phosphatase-conjugated goat anti-rabbit IgG second antibody.

Finally, Western immunoblot analysis was performed to determine whether non-typeable Haemophilus strains expressed proteins antigenically related to the filamentous hemagglutinin protein of *Bordetella pertussis*. Monoclonal antibody X3C, a murine immunoglobulin G (IgG) antibody which recognizes filamentous hemagglutinin, was used to probe cell sonicates by Western blot. An alkaline phosphatase-conjugated goat anti-mouse IgG second antibody was used for detection.

To generate recombinant protein antiserum, *E. coli* BL21(DE3)/pLysS was transformed with pHMW1–4, and expression of recombinant protein was induced with IPTG, as described above. A cell sonicate of the bacterial cells was prepared and separated into a supernatant and pellet fraction by centrifugation at 10,000×g for 30 min. The recombinant protein fractionated with the pellet fraction. A rabbit was subcutaneously immunized on biweekly schedule with 1 mg of protein from the pellet fraction, the first dose given with Freund's complete adjuvant and subsequent doses with Freund's incomplete adjuvant. Following the fourth injection, the rabbit was bled. Prior to use in the Western blot assay, the antiserum was absorbed extensively with sonicates of the host *E. coli* strain transformed with cloning vector alone.

To assess the sharing of antigenic determinants between HMW1 and filamentous hemagglutinin, enzyme-linked immunosorbent assay (ELISA) plates (Costar, Cambridge, Mass.) were coated with 60 μl of a 4-ug/ml solution of filamentous hemagglutinin in Dulbecco's phosphate-buffered saline per well for 2 h at room temperature. Wells were blocked for 1 h with 1% bovine serum albumin in Dulbecco's phosphate-buffered saline prior to addition of serum dilutions. rHMW1 antiserum was serially diluted in 0.1% Brij (Sigma, St. Louis, Mo.) in Dulbecco's phosphate-buffered saline and incubated for 3 h at room temperature. After being washed, the plates were incubated with peroxidase-conjugated goat anti-rabbit lgG antibody (Bio-Rad) for 2 h at room temperature and subsequently developed with 2,2'-azino-bis(3-ethylbenzthiazoline-6-sulfonic acid) (Sigma) at a concentration of 0.54 in mg/ml in 0.1M sodium citrate buffer, pH 4.2, containing 0.03% $H_2O_2$. Absorbances were read on an automated ELISA reader.

Recombinant phage expressing HMW1 or HMW2 were recovered as follows. The non-typeable *H. influenzae* strain 12 genomic library was screened for clones expressing high-molecular-weight proteins with an *E. coli*-absorbed human serum sample containing a high titer of antibodies directed against the high-molecular-weight proteins.

Numerous strongly reactive clones were identified along with more weakly reactive ones. Twenty strongly reactive clones were plaque-purified and examined by Western blot for expression of recombinant proteins. Each of the strongly reactive clones expressed one of two types of high-molecular-weight proteins, designated HMW1 and HMW2. The major immunoreactive protein bands in the HMW1 and HMW2 lysates migrated with apparent molecular masses of 125 and 120 kDa, respectively. In addition to the major bands, each lysate contained minor protein bands of higher apparent molecular weight. Protein bands seen in the HMW2 lysates at molecular masses of less than 120 kDa were not regularly observed and presumably represent proteolytic degradation products. Lysates of LE392 infected with the λEMBL3 cloning vector alone were non-reactive when immunologically screened with the same serum sample. Thus, the observed activity was not due to cross-reactive *E. coli* proteins or λEMBL3-encoded proteins. Furthermore, the recombinant proteins were not simply binding immunoglobulin nonspecifically, since the proteins were not reactive with the goat anti-human IgG conjugate alone, with normal rabbit sera, or with serum from a number of healthy young infants.

Representative clones expressing either the HMW1 or HMW2 recombinant proteins were characterized further. The restriction maps of the two phage types were different from each other, including the regions encoding the HMW1 and HMW2 structural genes. FIG. 5A shows restriction maps of representative recombinant phage which contained the HMW1 or HMW2 structural genes. The locations of the structural genes are indicated by the shaded bars.

HMW1 plasmid subclones were constructed by using the T7 expression plasmid T7-7 (FIG. 5A and B). HMW2 plasmid subclones also were constructed, and the results with these latter subclones were similar to those observed with the HMW1 constructs.

The approximate location and direction of transcription of the HMW1 structure gene were initially determined by using plasmid pHMW1 (FIG. 5A). This plasmid was constructed by inserting the 8.5-kb BamHI-SalI fragment from λHMW1 into BamHI- and SalI-cut pT7-7. *E. Coli* transformed with pHMW1 expressed an immunoreactive recombinant protein with an apparent molecular mass of 115 kDa, which was strongly inducible with IPTG. This protein was significantly smaller than the 125-kDa major protein expressed by the parent phage, indicating that it either was being expressed as a fusion protein or was truncated at the carboxy terminus.

To more precisely localize the 3' end of the structural gene, additional plasmids were constructed with progressive deletions from the 3' end of the pHMW1 construct. Plasmid pHMW1-1 was constructed by digestion of pHMW1 with PstI, isolation of the resulting 8.8-kb fragment, and religation. Plasmid pHMW1-2 was constructed by digestion of pHMW1 with HindIII, isolation of the resulting 7.5-kb fragment, and religation. *E. coli* transformed with either plasmid pHMW1-1 or pHMW1-2 also expressed an immunoreactive recombinant protein with an apparent molecular mass of 115 kDa. These results indicated that the 3' end of the structural gene was 5' of the HindIII site.

To more precisely localize the 5' end of the gene, plasmids pHMW1-4 and pHMW1-7 were constructed. Plasmid pHMW1-4 was constructed by cloning the 5.1-kb BamHI-HindIII fragment from λHMW1 into a pT7-7-derived plasmid containing the upstream 3.8-kb EcoRI-BamHi fragment. *E. coli* transformed with pHMW1-4 expressed an immunoreactive protein with an apparent molecular mass of approximately 160 kDa. Although protein production was inducible with IPTG, the levels of protein production in these transformants were substantially lower than those with the pHMW1-2 transformants described above. Plasmid pHMW1-7 was constructed by digesting pHMW1-4 with NdeI and SpeI. The 9.0-kbp fragment generated by this double digestion was isolated, blunt ended, and religated. *E. coli* transformed with pHMW1-7 also expressed an immunoreactive protein with an apparent molecular mass of 160 kDa, a protein identical in size to that expressed by the pHMW1-4 transformants. The result indicated that the initiation codon for the HMW1 structural gene was 3' of the SpeI site. DNA sequence analysis confirmed this conclusion.

As noted above, the λHMW1 phage clones expressed a major immunoreactive band of 125 kDa, whereas the HMW1 plasmid clones pHMW1-4 and pHMW1-7, which contained what was believed to be the full-length gene, expressed an immunoreactive protein of approximately 160 kDa. This size discrepancy was disconcerting. One possible explanation was that an additional gene or genes necessary for correct processing of the HMW1 gene product were deleted in the process of subcloning. To address this possibility, plasmid pHMW1-14 was constructed. This construct was generated by digesting pHMW1 with NdeI and MluI and inserting the 7.6-kbp NdeI-MluI fragment isolated from pHMW1-4. Such a construct would contain the full-length HMW1 gene as well as the DNA 3' of the HMW1 gene which was present in the original HMW1 phage. *E. coli* transformed with this plasmid expressed major immunoreactive proteins with apparent molecular masses of 125 and 160 kDa as well as additional degradation products. The 125- and 160-kDa bands were identical to the major and minor immunoreactive bands detected in the HMW1 phage lysates. Interestingly, the pHMW1-14 construct also expressed significant amounts of protein in the uninduced condition, a situation not observed with the earlier constructs.

The relationship between the 125- and 160-kDa proteins remains somewhat unclear. Sequence analysis, described below, reveals that the HMW1 gene would be predicted to encode a protein of 159 kDa. It is believed that the 160-kDa protein is a precursor form of the mature 125-kDa protein, with the conversion from one protein to the other being dependent on the products of the two downstream genes.

Sequence analysis of the HMW1 gene (FIG. 1) revealed a 4,608-bp open reading frame (ORF), beginning with an ATG codon at nucleotide 351 and ending with a TAG stop codon at nucleotide 4959. A putative ribosome-binding site with the sequence AGGAG begins 10 bp up-stream of the putative initiation codon. Five other in-frame ATG codons are located within 250 bp of the beginning of the ORF, but none of these is preceded by a typical ribosome-binding site. The 5'-flanking region of the ORF contains a series of direct tandem repeats, with the 7-bp sequence ATCTTTC repeated 16 times. These tandem repeats stop 100 bp 5' of the putative initiation codon. An 8-bp inverted repeat characteristic of a rho-independent transcriptional terminator is present, beginning at nucleotide 4983, 25 bp 3' of the presumed translational stop. Multiple termination codons are present in all three reading frames both upstream and downstream of the ORF. The derived amino acid sequence of the protein encoded by the HMW1 gene (FIG. 2) has a molecular weight of 159,000, in good agreement with the apparent molecular weights of the proteins expressed by the HMW1-4 and HMW1-7 transformants. The derived amino acid sequence of the amino terminus does not demonstrate the characteristics of a typical signal sequence. The BamHI site used in generation of pHMW1 comprises bp 1743 through 1748 of the nucleotide sequence. The ORF downstream of the BamHI site would be predicted to encode a protein of 111 kDa, in good agreement with the 115 kDa estimated for the apparent molecular mass of the pHMW1-encoded fusion protein.

The sequence of the HMW2 gene (FIG. 3) consists of a 4,431-bp ORF, beginning with an ATG codon at nucleotide 352 and ending with a TAG stop codon at nucleotide 4783. The first 1,259 bp of the ORF of the HMW2 gene are identical to those of the HMW1 gene. Thereafter, the sequences begin to diverge but are 80% identical overall. With the exception of a single base addition at nucleotide 93 of the HMW2 sequence, the 5'-flanking regions of the HMW1 and HMW2 genes are identical for 310 bp upstream from the respective initiation codons. Thus, the HMW2 gene is preceded by the same set of tandem repeats and the same putative ribosome-binding site which lies 5' of the HMW1 gene. A putative transcriptional terminator identical to that identified 3' of the HMW1 ORF is noted, beginning at nucleotide 4804. The discrepancy in the lengths of the two genes is principally accounted for by a 186-bp gap in the HMW2 sequence, beginning at nucleotide position 3839. The derived amino acid sequence of the protein encoded by the HMW2 gene (FIG. 4) has a molecular weight of 155,000 and is 71% identical with the derived amino acid sequence of the HMW1 gene.

The derived amino acid sequences of both the HMW1 and HMW2 genes (FIGS. 2 and 4) demonstrated sequence similarity with the derived amino acid sequence of filamentous hemagglutinin of *Bordetella pertussis*, a surface-associated protein of this organism. The initial and optimized TFASTA scores for the HMW1-filamentous hemagglutinin sequence comparison were 87 and 186, respectively, with a word size of 2. The z score for the comparison was 45.8. The initial and optimized TFASTA scores for the HMW2-filamentous hemagglutinin sequence comparison were 68 and 196, respectively. The z score for the latter comparison was 48.7. The magnitudes of the initial and optimized TFASTA scores and the z scores suggested that a biologically significant relationship existed between the HMW1 and HMW2 gene products and filamentous hemagglutinin. When the derived amino acid sequences of HMW1, HMW2, and filamentous hemagglutinin genes were aligned and compared, the similarities were most notable at the amino-terminal ends of the three sequences. Twelve of the first 22 amino acids in the predicted peptide sequences were identical. In additional, the sequences demonstrated a common five-amino-acid stretch, Asn-Pro-Asn-Gly-Ile, and several shorter stretches of sequence identity within the first 200 amino acids.

Example 2

To further explore the HMW1-filamentous hemagglutinin relationship, the ability of antiserum prepared against the HMW1-4 recombinant protein (rHMW1) to recognize purified filamentous hemagglutinin was assessed. The rHMW1 antiserum demonstrated ELISA reactivity with filamentous hemagglutinin in a dose-dependent manner. Preimmune rabbit serum had minimal reactivity in this assay. The rHMW1 antiserum also was examined in a Western blot assay and demonstrated weak but positive reactivity with purified filamentous hemagglutinin in this system also.

To identify the native Haemophilus protein corresponding to the HMW1 gene product and to determine the extent to which proteins antigenically related to the HMW1 cloned gene product were common among other non-typeable *H. influenzae* strains, a panel of Haemophilus strains was screened by Western blot with the rHMW1 antiserum. The antiserum recognized both a 125- and a 120-kDa protein band in the homologous strain 12, the putative mature protein products of the HMW1 and HMW2 genes, respectively.

When used to screen heterologous non-typeable *H. influenzae* strains, rHMW1 antiserum recognized high-molecular-weight proteins in 75% of 125 epidemiologically unrelated strains. In general, the antiserum reacted with one or two protein bands in the 100- to 150-kDa range in each of the heterologous strains in a pattern similar but not identical to that seen in the homologous strain.

Monoclonal antibody X3C is a murine IgG antibody directed against the filamentous hemagglutinin protein of *B. pertussis*. This antibody can inhibit the binding of *B. pertussis* cells to Chinese hamster ovary cells and HeLa cells in culture and will inhibit hemagglutination of erythrocytes by purified filamentous hemagglutinin. A Western blot assay was performed in which this monoclonal antibody was screened against the same panel of non-typeable *H. influenzae* strains discussed above. Monoclonal antibody X3C recognized both the high-molecular-weight proteins in non-typeable *H. influenzae* strain 12 which were recognized by the recombinant-protein antiserum. In addition, the monoclonal antibody recognized protein bands in a subset of heterologous non-typeable *H. influenzae* strains which were identical to those recognized by the recombinant-protein antiserum. On occasion, the filamentous hemagglutinin monoclonal antibody appeared to recognize only one of the two bands which had been recognized by the recombinant-protein antiserum. Overall, monoclonal antibody X3C recognized high-molecular-weight protein bands identical to those recognized by the rHMW1 antiserum in approximately 35% of our collection of non-typeable *H. influenzae* strains.

Example 3

Mutants deficient in expression of HMW1, MW2 or both proteins were constructed to examine the role of these proteins in bacterial adherence. The following strategy was employed. pHMW1-14 (see Example 1, FIG. 5A) was digested with BamHI and then ligated to a kanamycin cassette isolated on a 1.3-kb BamHI fragment from pUC4K. The resultant plasmid (pHMW1-17) was linearized by digestion with XbaI and transformed into non-typeable H. influenzae strain 12, followed by selection for kanamycin resistant colonies. Southern analysis of a series of these colonies demonstrated two populations of transformants, one with an insertion in the HMW1 structural gene and the other with an insertion in the HMW2 structural gene. One mutant from each of these classes was selected for further studies.

Mutants deficient in expression of both proteins were recovered using the following protocol. After deletion of the 2.1-kb fragment of DNA between two EcoRI sites spanning the 3'-portion of the HMW1 structural gene in pHMW-15, the kanamycin cassette from pUC4K was inserted as a 1.3-kb EcoRI fragment. The resulting plasmid (pHMW1-16) was linearized by digestion with XbaI and transformed into strain 12, followed again by selection for kanamycin resistant colonies. Southern analysis of a representative sampling of these colonies demonstrated that in seven of eight cases, insertion into both the HMW1 and HMW2 loci had occurred. One such mutant was selected for further studies.

To confirm the intended phenotypes, the mutant strains were examined by Western blot analysis with a polyclonal antiserum against recombinant HMW1 protein. The parental strain expressed both the 125-kD HMW1 and the 120-kD HMW2 protein. In contrast, the HMW2 mutant failed to express the 120-kD protein, and the HMW1 mutant failed to express the 125-kD protein. The double mutant lacked expression of either protein. On the basis of whole cell lysates, outer membrane profiles, and colony morphology, the wild type strain and the mutants were otherwise identical with one another. Transmission electron microscopy demonstrated that none of the four strains expressed pili.

The capacity of wild type strain 12 to adhere to Chang epithelial cells was examined. In such assays, bacteria were inoculated into broth and allowed to grow to a density of ~$2\times10^9$ cfu/ml. Approximately $2\times10^7$ cfu were inoculated onto epithelial cell monolayers, and plates were gently centrifuged at 165×g for 5 minutes to facilitate contact between bacteria and the epithelial surface. After incubation for 30 minutes at 37° C. in 5% $CO_2$, monolayers were rinsed 5 times with PBS to remove nonadherent organisms and were treated with trypsin-EDTA (0.05% trypsin, 0.5% EDTA) in PBS to release them from the plastic support. Well contents were agitated, and dilutions were plated on solid medium to yield the number of adherent bacteria per monolayer. Percent adherence was calculated by dividing the number of adherent cfu per monolayer by the number of inoculated cfu.

As depicted in Table 1 below (the Tables appear at the end of the descriptive text), this strain adhered quite efficiently, with nearly 90% of the inoculum binding to the monolayer. Adherence by the mutant expressing HMW1 but not HMW2 ($HMW2^-$) was also quite efficient and comparable to that by the wild type strain. In contrast, attachment by the strain expressing HMW2 but deficient in expression of HMW1 ($HMW1^-$) was decreased about 15-fold relative to the wild type. Adherence by the double mutant ($HMW1^-/HMW2^-$) was decreased even further, approximately 50-fold compared with the wild type and approximately 3-fold compared with the HMW1 mutant. Considered together, these results suggest that both the HMW1 protein and the, HMW2 protein influence attachment to Chang epithelial cells. Interestingly, optimal adherence to this cell line appears to require HMW1 but not HMW2.

Example 4

Using the plasmids pHMW1-16 and pHMW1-17 (see Example 3) and following a scheme similar to that employed with strain 12 as described in Example 3, three non-typeable Haemophilus strain 5 mutants were isolated, including one with the kanamycin gene inserted into the hmw1-like (designated hmw3) locus, a second with an insertion in the hmw2-like (designated hmw4) locus, and a third with insertions in both loci. As predicted, Western immunoblot analysis demonstrated that the mutant with insertion of the kanamycin cassette into the hmw1-like locus had lost expression of the HMW3 125-kD protein, while the mutant with insertion into the hmw2-like locus failed to express the HMW4 123-kD protein. The mutant with a double insertion was unable to express either of the high molecular weight proteins.

As shown in Table 1 below, wild type strain 5 demonstrated high level adherence, with almost 80% of the inoculum adhering per monolayer. Adherence by the mutant deficient in expression of the HMW2-like protein was also quite high. In contrast, adherence by the mutant unable to express the, HMW1-like protein was reduced about 5-fold relative to the wild type, and attachment by the double mutant was diminished even further (approximately 25-fold). Examination of Giemsa-stained samples confirmed these observations (not shown). Thus, the results with strain 5 corroborate the findings with strain 12 and the HMW1 and HMW2 proteins.

Example 5

To confirm an adherence function for the HMW1 and HMW2 proteins and to examine the effect of HMW1 and HMW2 independently of other *H. influenzae* surface structures, the hmw1 and the hmw2 gene clusters were introduced into *E. coli* DH5α, using plasmids pHMW1-14 and pHMW2-21, respectively. As a control, the cloning vector, pT7-7, was also transformed into *E. coli* DH5α. Western blot analysis demonstrated that *E. coli* DH5α containing the hmw1 genes expressed a 125 kDa protein, while the same strain harboring the hmw2 genes expressed a 120-kDa protein. *E. coli* DH5α containing pT7-7 failed to react with antiserum against recombinant HMW1. Transmission electron microscopy revealed no pili or other surface appendages on any of the *E. coli* strains.

Adherence by the *E. coli* strains was quantitated and compared with adherence by wild type non-typeable *H. influenzae* strain 12. As shown in Table 2 below, adherence by *E. coli* DH5α containing vector alone was less than 1% of that for strain 12. In contrast, *E. coli* DH5α harboring the hmw1 gene cluster demonstrated adherence levels comparable to those for strain 12. Adherence by *E. coli* DH5α containing the hmw2 genes was approximately 6-fold lower than attachment by strain 12 but was increased 20-fold over adherence by *E. coli* DH5α with pT7-7 alone. These results indicate that the HMW1 and HMW2 proteins are capable of independently mediating attachment to Chang conjunctival cells. These results are consistent with the results with the *H. influenzae* mutants reported in Examples 3 and 4, providing further evidence that, with Chang epithelial cells, HMW1 is a more efficient adhesin than is HMW2.

Experiments with *E. coli* HB101 harboring pT7-7, pHMW1-14, or pHMW2-21 confirmed the results obtained with the DH5α derivatives (see Table 2).

Example 6

HMW1 and HMW2 were isolated and purified from non-typeable *H. influenzae* (NTHI) strain 12 in the following manner. Non-typeable Haemophilus bacteria from frozen stock culture were streaked onto a chocolate plate and grown overnight at 37° C. in an incubator with 5% $CO_2$. 50 ml starter culture of brain heart infusion (BHI) broth, supplemented with 10 μg/ml each of hemin and NAD was inoculated with growth on chocolate plate. The starter culture was grown until the optical density (O.D.—600 nm) reached 0.6 to 0.8 and then the bacteria in the starter culture was used to inoculate six 500 ml flasks of supplemented BHI using 8 to 10 ml per flask. The bacteria were grown in 500 ml flasks for an additional 5 to 6 hours at which time the O.D. was 1.5 or greater. Cultures were centrifuged at 10,000 rpm for 10 minutes.

Bacterial pellets were resuspended in a total volume of 250 ml of an extraction solution comprising 0.5M NaCl, 0.01M $Na_2EDTA$, 0.01M Tris 50 μM 1,10-phenanthroline, pH 7.5. The cells were not sonicated or otherwise disrupted. The resuspended cells were allowed to sit on ice at 0° C. for 60 minutes. The resuspended cells were centrifuged at 10,000 rpm for 10 minutes at 4° C. to remove the majority of intact cells and cellular debris. The supernatant was collected and centrifuged at 100,000×g for 60 minutes at 4° C. The supernatant again was collected and dialyzed overnight at 4° C. against 0.01M sodium phosphate, pH 6.0.

The sample was centrifuged at 10,000 rpm for 10 minutes at 4° C. to remove insoluble debris precipitated from solution during dialysis. The supernatant was applied to a 10 ml CM Sepharose column which has been pre-equilibrated with 0.01M sodium phosphate, pH 6. Following application to this column, the column was washed with 0.01M sodium phosphate. Proteins were elevated from the column with a 0–0.5M KCl gradient in 0.01M Na phosphate, pH 6 and fractions were collected for gel examination. Coomassie gels of column fractions were carried out to identify those fractions containing high molecular weight proteins. The fractions containing high molecular weight proteins were pooled and concentrated to a 1 to 3 ml volume in preparation for application of sample to gel filtration column.

A Sepharose CL-4B gel filtration column was equilibrated with phosphate-buffered saline, pH 7.5. The concentrated high molecular weight protein sample was applied to the gel filtration column and column fractions were collected. Coomassie gels were performed on the column fractions to identify those containing high molecular weight proteins. The column fractions containing high molecular weight proteins were pooled.

The proteins were tested to determine whether they would protect against experimental otitis media caused by the homologous strain.

Chinchillas received three monthly subcutaneous injections with 40 μg of an HMW1-HMW2 protein mixture in Freund's adjuvant. One month after the last injection, the animals were challanged by intrabullar inoculation with 300 cfu of NTHI strain 12.

Infection developed in 5 of 5 control animals versus 5 of 10 immunized animals. Among infected animals, geometric mean bacterial counts in middle ear fluid 7 days post-challenge were $7.4\times10^6$ in control animals versus $1.3\times10^5$ in immunized animals.

Serum antibody titres following immunization were comparable in uninfected and infected animals. However, infection in immunized animals was uniformly associated with the appearance of bacteria down-regulated in expression of the HMW proteins, suggesting bacterial selection in response to immunologic pressure.

Although this data shows that protection following immunization was not complete, this data suggests the HMW adhesin proteins are potentially important protective antigens which may comprise one component of a multicomponent NTHI vaccine.

Example 7

A number of synthetic peptides were derived from HMW1. Antisera then was raised to these peptides. The anti-peptide antisera to peptide HMW1-P5 was shown to recognize HMW1. Peptide HMW1-P5 covers amino acids 1453 to 1481 of HMW1, has the sequence VDEVIEAKRILEKVKDLSDEEREALAKLG (SEQ ID NO:9), and represents bases 1498 to 1576 in FIG. 10.

This finding demonstrates that the DNA sequence and the derived protein is being interpreted in the correct reading frame and that peptides derived from the sequence can be produced which will be immunogenic.

SUMMARY OF DISCLOSURE

In summary of this disclosure, the present invention provides high molecular weight proteins of non-typeable Haemophilus, genes coding for the same and vaccines incorporating such proteins. Modifications are possible within the scope of this invention.

TABLE 1

Effect of mutation of high molecular weight proteins on adherence to Chang epithelial cells by nontypable *H. influenzae.*

| Strain | ADHERENCE* % inoculum | ADHERENCE* relative to wild type† |
|---|---|---|
| Strain 12 derivatives | | |
| wild type | 87.7 ± 5.9 | 100.0 ± 6.7 |
| HMW1-mutant | 6.0 ± 0.9 | 6.8 ± 1.0 |
| HMW2-mutant | 89.9 ± 10.8 | 102.5 ± 12.3 |
| HMW1-/HMW2-mutant | 2.0 ± 0.3 | 2.3 ± 0.3 |
| Strain 5 derivatives | | |
| wild type | 78.7 ± 3.2 | 100.0 ± 4.1 |
| HMW1-like mutant | 15.7 ± 2.6 | 19.9 ± 3.3 |
| HMW2-like mutant | 103.7 ± 14.0 | 131.7 ± 17.8 |
| double mutant | 3.5 ± 0.6 | 4.4 ± 0.8 |

*Numbers represent mean (± standard error of the mean) of measurements in triplicate or quadruplicate from representative experiments.
†Adherence values for strain 12 derivatives are relative to strain 12 wild type; values for strain 5 derivatives are relative to strain 5 wild type.

TABLE 2

Adherence by *E. coli* DH5α and HB101 harboring hmw1 or hmw2 gene clusters.

| Strain* | Adherence relative to *H. influenzae* strain 12† |
|---|---|
| DH5α (pT7-7) | 0.7 ± 0.02 |
| DH5α (pHMW1-14) | 114.2 ± 15.9 |
| DH5α (pHMW2-21) | 14.0 ± 3.7 |
| HB101 (pT7-7) | 1.2 ± 0.5 |
| HB101 (pHMW1-14) | 93.6 ± 15.8 |
| HB101 (pHMW2-21) | 3.6 ± 0.9 |

*The plasmid pHMW1-14 contains the hmw1 gene cluster, while pHMW2-21 contains the hmw2 gene cluster; pT7-7 is the cloning vector used in these constructs.
†Numbers represent the mean (± standard error of the mean) of measurements made in triplicate from representative experiments.

What we claim is:

1. A vaccine against disease caused by non-typeable *Haemophilus influenzae*, including otitis media, sinusitis and bronchitis, comprising an effective amount of a high molecular weight protein of non-typeable *Haemophilus influenzae* which is protein HMW1 and/or HMW2 and a physiological carrier therefor.

2. The vaccine of claim 1 wherein said protein is HMW1 encoded by the DNA sequence shown in FIG. 1 (SEQ ID NO:1), having the derived amino acid sequence of FIG. 2 (SEQ ID ID NO:2) and having an apparent molecular weight of 125 kDa.

3. The vaccine of claim 1 wherein said protein is HMW2 encoding by the DNA sequence shown in FIG. 3 SEQ ID NO:3), having the derived amino acid sequence of FIG. 4 SEQ ID NO:4) and having an apparent molecular weight of 120 kDa.

* * * * *

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
( A ) LENGTH: 5116 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:1:

```
ACAGCGTTCT CTTAATACTA GTACAAACCC ACAATAAAAT ATGACAAACA ACAATTACAA    60
CACCTTTTTT GCAGTCTATA TGCAAATATT TTAAAAAATA GTATAAATCC GCCATATAAA   120
ATGGTATAAT CTTTCATCTT TCATCTTTCA TCTTTCATCT TTCATCTTTC ATCTTTCATC   180
TTTCATCTTT CATCTTTCAT CTTTCATCTT TCATCTTTCA TCTTTCATCT TTCATCTTTC   240
ACATGCCCTG ATGAACCGAG GGAAGGGAGG GAGGGGCAAG AATGAAGAGG GAGCTGAACG   300
AACGCAAATG ATAAAGTAAT TTAATTGTTC AACTAACCTT AGGAGAAAAT ATGAACAAGC   360
TATATCGTCT CAAATTCAGC AAACGCCTGA ATGCTTTGGT TGCTGTGTCT GAATTGGCAC   420
```

-continued

```
GGGGTTGTGA CCATTCCACA GAAAAAGGCA GCGAAAAACC TGCTCGCATG AAAGTGCGTC    480
ACTTAGCGTT AAAGCCACTT TCCGCTATGT TACTATCTTT AGGTGTAACA TCTATTCCAC    540
AATCTGTTTT AGCAAGCGGC TTACAAGGAA TGGATGTAGT ACACGGCACA GCCACTATGC    600
AAGTAGATGG TAATAAAACC ATTATCCGCA ACAGTGTTGA CGATATCATT AATTGGAAAC    660
AATTTAACAT CGACCAAAAT GAAATGGTGC AGTTTTTACA AGAAAACAAC AACTCCGCCG    720
TATTCAACCG TGTTACATCT AACCAAATCT CCCAATTAAA AGGGATTTTA GATTCTAACG    780
GACAAGTCTT TTTAATCAAC CCAAATGGTA TCACAATAGG TAAAGACGCA ATTATTAACA    840
CTAATGGCTT TACGGCTTCT ACGCTAGACA TTTCTAACGA AAACATCAAG GCGCGTAATT    900
TCACCTTCGA GCAAACCAAA GATAAAGCGC TCGCTGAAAT TGTGAATCAC GGTTTAATTA    960
CTGTCGGTAA AGACGGCAGT GTAAATCTTA TTGGTGGCAA AGTGAAAAAC GAGGGTGTGA   1020
TTAGCGTAAA TGGTGGCAGC ATTTCTTTAC TCGCAGGGCA AAAAATCACC ATCAGCGATA   1080
TAATAAACCC AACCATTACT TACAGCATTG CCGCGCCTGA AAATGAAGCG GTCAATCTGG   1140
GCGATATTTT TGCCAAAGGC GGTAACATTA ATGTCCGTGC TGCCACTATT CGAAACCAAG   1200
GTAAACTTTC TGCTGATTCT GTAAGCAAAG ATAAAAGCGG CAATATTGTT CTTTCCGCCA   1260
AAGAGGGTGA AGCGGAAATT GGCGGTGTAA TTTCCGCTCA AAATCAGCAA GCTAAAGGCG   1320
GCAAGCTGAT GATTACAGGC GATAAAGTCA CATTAAAAAC AGGTGCAGTT ATCGACCTTT   1380
CAGGTAAAGA AGGGGGAGAA ACTTACCTTG GCGGTGACGA GCGCGGCGAA GGTAAAAAGG   1440
GCATTCAATT AGCAAAGAAA ACCTCTTTAG AAAAAGGCTC AACCATCAAT GTATCAGGCA   1500
AAGAAAAAGG CGGACGCGCT ATTGTGTGGG GCGATATTGC GTTAATTGAC GGCAATATTA   1560
ACGCTCAAGG TAGTGGTGAT ATCGCTAAAA CCGGTGGTTT TGTGGAGACG TCGGGGCATG   1620
ATTTATTCAT CAAAGACAAT GCAATTGTTG ACGCCAAAGA GTGGTTGTTA GACCCGGATA   1680
ATGTATCTAT TAATGCAGAA ACAGCAGGAC GCAGCAATAC TTCAGAAGAC GATGAATACA   1740
CGGGATCCGG GAATAGTGCC AGCACCCCAA AACGAAACAA AGAAAAGACA ACATTAACAA   1800
ACACAACTCT TGAGAGTATA CTAAAAAAAG GTACCTTTGT TAACATCACT GCTAATCAAC   1860
GCATCTATGT CAATAGCTCC ATTAATTTAT CCAATGGCAG CTTAACTCTT TGGAGTGAGG   1920
GTCGGAGCGG TGGCGGCGTT GAGATTAACA ACGATATTAC CACCGGTGAT GATACCAGAG   1980
GTGCAAACTT AACAATTTAC TCAGGCGGCT GGGTTGATGT TCATAAAAAT ATCTCACTCG   2040
GGGCGCAAGG TAACATAAAC ATTACAGCTA AACAAGATAT CGCCTTTGAG AAAGGAAGCA   2100
ACCAAGTCAT TACAGGTCAA GGGACTATTA CCTCAGGCAA TCAAAAAGGT TTTAGATTTA   2160
ATAATGTCTC TCTAAACGGC ACTGGCAGCG GACTGCAATT CACCACTAAA AGAACCAATA   2220
AATACGCTAT CACAAATAAA TTTGAAGGGA CTTTAAATAT TTCAGGGAAA GTGAACATCT   2280
CAATGGTTTT ACCTAAAAAT GAAAGTGGAT ATGATAAATT CAAAGGACGC ACTTACTGGA   2340
ATTTAACCTC CTTAAATGTT TCCGAGAGTG GCGAGTTTAA CCTCACTATT GACTCCAGAG   2400
GAAGCGATAG TGCAGGCACA CTTACCCAGC CTTATAATTT AAACGGTATA TCATTCAACA   2460
AAGACACTAC CTTTAATGTT GAACGAAATG CAAGAGTCAA CTTTGACATC AAGGCACCAA   2520
TAGGGATAAA TAAGTATTCT AGTTTGAATT ACGCATCATT TAATGGAAAC ATTTCAGTTT   2580
CGGGAGGGGG GAGTGTTGAT TTCACACTTC TCGCCTCATC CTCTAACGTC CAAACCCCCG   2640
GTGTAGTTAT AAATTCTAAA TACTTTAATG TTTCAACAGG GTCAAGTTTA AGATTTAAAA   2700
CTTCAGGCTC AACAAAAACT GGCTTCTCAA TAGAGAAAGA TTTAACTTTA AATGCCACCG   2760
GAGGCAACAT AACACTTTTG CAAGTTGAAG GCACCGATGG AATGATTGGT AAAGGCATTG   2820
```

-continued

| | | | | | | |
|---|---|---|---|---|---|---|
| TAGCCAAAAA | AAACATAACC | TTTGAAGGAG | GTAACATCAC | CTTTGGCTCC | AGGAAAGCCG | 2880 |
| TAACAGAAAT | CGAAGGCAAT | GTTACTATCA | ATAACAACGC | TAACGTCACT | CTTATCGGTT | 2940 |
| CGGATTTTGA | CAACCATCAA | AAACCTTTAA | CTATTAAAAA | AGATGTCATC | ATTAATAGCG | 3000 |
| GCAACCTTAC | CGCTGGAGGC | AATATTGTCA | ATATAGCCGG | AAATCTTACC | GTTGAAAGTA | 3060 |
| ACGCTAATTT | CAAAGCTATC | ACAAATTTCA | CTTTTAATGT | AGGCGGCTTG | TTTGACAACA | 3120 |
| AAGGCAATTC | AAATATTTCC | ATTGCCAAAG | GAGGGGCTCG | CTTTAAAGAC | ATTGATAATT | 3180 |
| CCAAGAATTT | AAGCATCACC | ACCAACTCCA | GCTCCACTTA | CCGCACTATT | ATAAGCGGCA | 3240 |
| ATATAACCAA | TAAAAACGGT | GATTTAAATA | TTACGAACGA | AGGTAGTGAT | ACTGAAATGC | 3300 |
| AAATTGGCGG | CGATGTCTCG | CAAAAAGAAG | GTAATCTCAC | GATTTCTTCT | GACAAAATCA | 3360 |
| ATATTACCAA | ACAGATAACA | ATCAAGGCAG | GTGTTGATGG | GGAGAATTCC | GATTCAGACG | 3420 |
| CGACAAACAA | TGCCAATCTA | ACCATTAAAA | CCAAAGAATT | GAAATTAACG | CAAGACCTAA | 3480 |
| ATATTTCAGG | TTTCAATAAA | GCAGAGATTA | CAGCTAAAGA | TGGTAGTGAT | TTAACTATTG | 3540 |
| GTAACACCAA | TAGTGCTGAT | GGTACTAATG | CCAAAAAAGT | AACCTTTAAC | CAGGTTAAAG | 3600 |
| ATTCAAAAAT | CTCTGCTGAC | GGTCACAAGG | TGACACTACA | CAGCAAAGTG | GAAACATCCG | 3660 |
| GTAGTAATAA | CAACACTGAA | GATAGCAGTG | ACAATAATGC | CGGCTTAACT | ATCGATGCAA | 3720 |
| AAAATGTAAC | AGTAAACAAC | AATATTACTT | CTCACAAAGC | AGTGAGCATC | TCTGCGACAA | 3780 |
| GTGGAGAAAT | TACCACTAAA | ACAGGTACAA | CCATTAACGC | AACCACTGGT | AACGTGGAGA | 3840 |
| TAACCGCTCA | AACAGGTAGT | ATCCTAGGTG | GAATTGAGTC | CAGCTCTGGC | TCTGTAACAC | 3900 |
| TTACTGCAAC | CGAGGGCGCT | CTTGCTGTAA | GCAATATTTC | GGGCAACACC | GTTACTGTTA | 3960 |
| CTGCAAATAG | CGGTGCATTA | ACCACTTTGG | CAGGCTCTAC | AATTAAAGGA | ACCGAGAGTG | 4020 |
| TAACCACTTC | AAGTCAATCA | GGCGATATCG | GCGGTACGAT | TTCTGGTGGC | ACAGTAGAGG | 4080 |
| TTAAAGCAAC | CGAAAGTTTA | ACCACTCAAT | CCAATTCAAA | AATTAAAGCA | ACAACAGGCG | 4140 |
| AGGCTAACGT | AACAAGTGCA | ACAGGTACAA | TTGGTGGTAC | GATTTCCGGT | AATACGGTAA | 4200 |
| ATGTTACGGC | AAACGCTGGC | GATTTAACAG | TTGGGAATGG | CGCAGAAATT | AATGCGACAG | 4260 |
| AAGGAGCTGC | AACCTTAACT | ACATCATCGG | GCAAATTAAC | TACCGAAGCT | AGTTCACACA | 4320 |
| TTACTTCAGC | CAAGGGTCAG | GTAAATCTTT | CAGCTCAGGA | TGGTAGCGTT | GCAGGAAGTA | 4380 |
| TTAATGCCGC | CAATGTGACA | CTAAATACTA | CAGGCACTTT | AACTACCGTG | AAGGGTTCAA | 4440 |
| ACATTAATGC | AACCAGCGGT | ACCTTGGTTA | TTAACGCAAA | AGACGCTGAG | CTAAATGGCG | 4500 |
| CAGCATTGGG | TAACCACACA | GTGGTAAATG | CAACCAACGC | AAATGGCTCC | GGCAGCGTAA | 4560 |
| TCGCGACAAC | CTCAAGCAGA | GTGAACATCA | CTGGGGATTT | AATCACAATA | AATGGATTAA | 4620 |
| ATATCATTTC | AAAAAACGGT | ATAAACACCG | TACTGTTAAA | AGGCGTTAAA | ATTGATGTGA | 4680 |
| AATACATTCA | ACCGGGTATA | GCAAGCGTAG | ATGAAGTAAT | TGAAGCGAAA | CGCATCCTTG | 4740 |
| AGAAGGTAAA | AGATTTATCT | GATGAAGAAA | GAGAAGCGTT | AGCTAAACTT | GGAGTAAGTG | 4800 |
| CTGTACGTTT | TATTGAGCCA | AATAATACAA | TTACAGTCGA | TACACAAAAT | GAATTTGCAA | 4860 |
| CCAGACCATT | AAGTCGAATA | GTGATTTCTG | AAGGCAGGGC | GTGTTTCTCA | AACAGTGATG | 4920 |
| GCGCGACGGT | GTGCGTTAAT | ATCGCTGATA | ACGGGCGGTA | GCGGTCAGTA | ATTGACAAGG | 4980 |
| TAGATTTCAT | CCTGCAATGA | AGTCATTTTA | TTTTCGTATT | ATTTACTGTG | TGGGTTAAAG | 5040 |
| TTCAGTACGG | GCTTTACCCA | TCTTGTAAAA | AATTACGGAG | AATACAATAA | AGTATTTTTA | 5100 |
| ACAGGTTATT | ATTATG | | | | | 5116 |

-continued ( 2 ) INFORMATION FOR SEQ ID NO:2:

( i ) SEQUENCE CHARACTERISTICS:
( A ) LENGTH: 1536 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:2:

| | | | | | | | | | | | | | | | |
|---|---|---|---|---|---|---|---|---|---|---|---|---|---|---|---|
| Met | Asn | Lys | Ile | Tyr | Arg | Leu | Lys | Phe | Ser | Lys | Arg | Leu | Asn | Ala | Leu |
| 1 | | | | 5 | | | | | 10 | | | | | 15 | |
| Val | Ala | Val | Ser | Glu | Leu | Ala | Arg | Gly | Cys | Asp | His | Ser | Thr | Glu | Lys |
| | | | 20 | | | | | 25 | | | | | 30 | | |
| Gly | Ser | Glu | Lys | Pro | Ala | Arg | Met | Lys | Val | Arg | His | Leu | Ala | Leu | Lys |
| | | 35 | | | | | 40 | | | | | 45 | | | |
| Pro | Leu | Ser | Ala | Met | Leu | Leu | Ser | Leu | Gly | Val | Thr | Ser | Ile | Pro | Gln |
| | 50 | | | | | 55 | | | | | 60 | | | | |
| Ser | Val | Leu | Ala | Ser | Gly | Leu | Gln | Gly | Met | Asp | Val | Val | His | Gly | Thr |
| 65 | | | | | 70 | | | | | 75 | | | | | 80 |
| Ala | Thr | Met | Gln | Val | Asp | Gly | Asn | Lys | Thr | Ile | Ile | Arg | Asn | Ser | Val |
| | | | | 85 | | | | | 90 | | | | | 95 | |
| Asp | Ala | Ile | Ile | Asn | Trp | Lys | Gln | Phe | Asn | Ile | Asp | Gln | Asn | Glu | Met |
| | | | 100 | | | | | 105 | | | | | 110 | | |
| Val | Gln | Phe | Leu | Gln | Glu | Asn | Asn | Asn | Ser | Ala | Val | Phe | Asn | Arg | Val |
| | | 115 | | | | | 120 | | | | | 125 | | | |
| Thr | Ser | Asn | Gln | Ile | Ser | Gln | Leu | Lys | Gly | Ile | Leu | Asp | Ser | Asn | Gly |
| | 130 | | | | | 135 | | | | | 140 | | | | |
| Gln | Val | Phe | Leu | Ile | Asn | Pro | Asn | Gly | Ile | Thr | Ile | Gly | Lys | Asp | Ala |
| 145 | | | | | 150 | | | | | 155 | | | | | 160 |
| Ile | Ile | Asn | Thr | Asn | Gly | Phe | Thr | Ala | Ser | Thr | Leu | Asp | Ile | Ser | Asn |
| | | | | 165 | | | | | 170 | | | | | 175 | |
| Glu | Asn | Ile | Lys | Ala | Arg | Asn | Phe | Thr | Phe | Glu | Gln | Thr | Lys | Asp | Lys |
| | | | 180 | | | | | 185 | | | | | 190 | | |
| Ala | Leu | Ala | Glu | Ile | Val | Asn | His | Gly | Leu | Ile | Thr | Val | Gly | Lys | Asp |
| | | 195 | | | | | 200 | | | | | 205 | | | |
| Gly | Ser | Val | Asn | Leu | Ile | Gly | Gly | Lys | Val | Lys | Asn | Glu | Gly | Val | Ile |
| | 210 | | | | | 215 | | | | | 220 | | | | |
| Ser | Val | Asn | Gly | Gly | Ser | Ile | Ser | Leu | Leu | Ala | Gly | Gln | Lys | Ile | Thr |
| 225 | | | | | 230 | | | | | 235 | | | | | 240 |
| Ile | Ser | Asp | Ile | Ile | Asn | Pro | Thr | Ile | Thr | Tyr | Ser | Ile | Ala | Ala | Pro |
| | | | | 245 | | | | | 250 | | | | | 255 | |
| Glu | Asn | Glu | Ala | Val | Asn | Leu | Gly | Asp | Ile | Phe | Ala | Lys | Gly | Gly | Asn |
| | | | 260 | | | | | 265 | | | | | 270 | | |
| Ile | Asn | Val | Arg | Ala | Ala | Thr | Ile | Arg | Asn | Gln | Gly | Lys | Leu | Ser | Ala |
| | | 275 | | | | | 280 | | | | | 285 | | | |
| Asp | Ser | Val | Ser | Lys | Asp | Lys | Ser | Gly | Asn | Ile | Val | Leu | Ser | Ala | Lys |
| | 290 | | | | | 295 | | | | | 300 | | | | |
| Glu | Gly | Glu | Ala | Glu | Ile | Gly | Gly | Val | Ile | Ser | Ala | Gln | Asn | Gln | Gln |
| 305 | | | | | 310 | | | | | 315 | | | | | 320 |
| Ala | Lys | Gly | Gly | Lys | Leu | Met | Ile | Thr | Gly | Asp | Lys | Val | Thr | Leu | Lys |
| | | | | 325 | | | | | 330 | | | | | 335 | |
| Thr | Gly | Ala | Val | Ile | Asp | Leu | Ser | Gly | Lys | Glu | Gly | Gly | Glu | Thr | Tyr |
| | | | 340 | | | | | 345 | | | | | 350 | | |
| Leu | Gly | Gly | Asp | Glu | Arg | Gly | Glu | Gly | Lys | Asn | Gly | Ile | Gln | Leu | Ala |
| | | 355 | | | | | 360 | | | | | 365 | | | |

| | | | | | | | | | | | | | | | |
|---|---|---|---|---|---|---|---|---|---|---|---|---|---|---|---|
| Lys | Lys | Thr | Ser | Leu | Glu | Lys | Gly | Ser | Thr | Ile | Asn | Val | Ser | Gly | Lys |
| | 370 | | | | | 375 | | | | | 380 | | | | |
| Glu | Lys | Gly | Gly | Arg | Ala | Ile | Val | Trp | Gly | Asp | Ile | Ala | Leu | Ile | Asp |
| 385 | | | | | 390 | | | | | 395 | | | | | 400 |
| Gly | Asn | Ile | Asn | Ala | Gln | Gly | Ser | Gly | Asp | Ile | Ala | Lys | Thr | Gly | Gly |
| | | | | 405 | | | | | 410 | | | | | 415 | |
| Phe | Val | Glu | Thr | Ser | Gly | His | Asp | Leu | Phe | Ile | Lys | Asp | Asn | Ala | Ile |
| | | | 420 | | | | | 425 | | | | | 430 | | |
| Val | Asp | Ala | Lys | Glu | Trp | Leu | Leu | Asp | Phe | Asp | Asn | Val | Ser | Ile | Asn |
| | | 435 | | | | | 440 | | | | | 445 | | | |
| Ala | Glu | Thr | Ala | Gly | Arg | Ser | Asn | Thr | Ser | Glu | Asp | Asp | Glu | Tyr | Thr |
| | 450 | | | | | 455 | | | | | 460 | | | | |
| Gly | Ser | Gly | Asn | Ser | Ala | Ser | Thr | Pro | Lys | Arg | Asn | Lys | Glu | Lys | Thr |
| 465 | | | | | 470 | | | | | 475 | | | | | 480 |
| Thr | Leu | Thr | Asn | Thr | Thr | Leu | Glu | Ser | Ile | Leu | Lys | Lys | Gly | Thr | Phe |
| | | | | 485 | | | | | 490 | | | | | 495 | |
| Val | Asn | Ile | Thr | Ala | Asn | Gln | Arg | Ile | Tyr | Val | Asn | Ser | Ser | Ile | Asn |
| | | | 500 | | | | | 505 | | | | | 510 | | |
| Leu | Ser | Asn | Gly | Ser | Leu | Thr | Leu | Trp | Ser | Glu | Gly | Arg | Ser | Gly | Gly |
| | | 515 | | | | | 520 | | | | | 525 | | | |
| Gly | Val | Glu | Ile | Asn | Asn | Asp | Ile | Thr | Thr | Gly | Asp | Asp | Thr | Arg | Gly |
| | 530 | | | | | 535 | | | | | 540 | | | | |
| Ala | Asn | Leu | Thr | Ile | Tyr | Ser | Gly | Gly | Trp | Val | Asp | Val | His | Lys | Asn |
| 545 | | | | | 550 | | | | | 555 | | | | | 560 |
| Ile | Ser | Leu | Gly | Ala | Gln | Gly | Asn | Ile | Asn | Ile | Thr | Ala | Lys | Gln | Asp |
| | | | | 565 | | | | | 570 | | | | | 575 | |
| Ile | Ala | Phe | Glu | Lys | Gly | Ser | Asn | Gln | Val | Ile | Thr | Gly | Gln | Gly | Thr |
| | | | 580 | | | | | 585 | | | | | 590 | | |
| Ile | Thr | Ser | Gly | Asn | Gln | Lys | Gly | Phe | Arg | Phe | Asn | Asn | Val | Ser | Leu |
| | | 595 | | | | | 600 | | | | | 605 | | | |
| Asn | Gly | Thr | Gly | Ser | Gly | Leu | Gln | Phe | Thr | Thr | Lys | Arg | Thr | Asn | Lys |
| | 610 | | | | | 615 | | | | | 620 | | | | |
| Tyr | Ala | Ile | Thr | Asn | Lys | Phe | Glu | Gly | Thr | Leu | Asn | Ile | Ser | Gly | Lys |
| 625 | | | | | 630 | | | | | 635 | | | | | 640 |
| Val | Asn | Ile | Ser | Met | Val | Leu | Pro | Lys | Asn | Glu | Ser | Gly | Tyr | Asp | Lys |
| | | | | 645 | | | | | 650 | | | | | 655 | |
| Phe | Lys | Gly | Arg | Thr | Tyr | Trp | Asn | Leu | Thr | Ser | Leu | Asn | Val | Ser | Glu |
| | | | 660 | | | | | 665 | | | | | 670 | | |
| Ser | Gly | Glu | Phe | Asn | Leu | Thr | Ile | Asp | Ser | Arg | Gly | Ser | Asp | Ser | Ala |
| | | 675 | | | | | 680 | | | | | 685 | | | |
| Gly | Thr | Leu | Thr | Gln | Pro | Tyr | Asn | Leu | Asn | Gly | Ile | Ser | Phe | Asn | Lys |
| | 690 | | | | | 695 | | | | | 700 | | | | |
| Asp | Thr | Thr | Phe | Asn | Val | Glu | Arg | Asn | Ala | Arg | Val | Asn | Phe | Asp | Ile |
| 705 | | | | | 710 | | | | | 715 | | | | | 720 |
| Lys | Ala | Pro | Ile | Gly | Ile | Asn | Lys | Tyr | Ser | Ser | Leu | Asn | Tyr | Ala | Ser |
| | | | | 725 | | | | | 730 | | | | | 735 | |
| Phe | Asn | Gly | Asn | Ile | Ser | Val | Ser | Gly | Gly | Gly | Ser | Val | Asp | Phe | Thr |
| | | | 740 | | | | | 745 | | | | | 750 | | |
| Leu | Leu | Ala | Ser | Ser | Ser | Asn | Val | Gln | Thr | Pro | Gly | Val | Val | Ile | Asn |
| | | 755 | | | | | 760 | | | | | 765 | | | |
| Ser | Lys | Tyr | Phe | Asn | Val | Ser | Thr | Gly | Ser | Ser | Leu | Arg | Phe | Lys | Thr |
| | 770 | | | | | 775 | | | | | 780 | | | | |
| Ser | Gly | Ser | Thr | Lys | Thr | Gly | Phe | Ser | Ile | Glu | Lys | Asp | Leu | Thr | Leu |

-continued 785 790 795 800

Asn Ala Thr Gly Gly Asn Ile Thr Leu Leu Gln Val Glu Gly Thr Asp
805 810 815

Gly Met Ile Gly Lys Gly Ile Val Ala Lys Lys Asn Ile Thr Phe Glu
820 825 830

Gly Gly Asn Ile Thr Phe Gly Ser Arg Lys Ala Val Thr Glu Ile Glu
835 840 845

Gly Asn Val Thr Ile Asn Asn Asn Ala Asn Val Thr Leu Ile Gly Ser
850 855 860

Asp Phe Asp Asn His Gln Lys Pro Leu Thr Ile Lys Lys Asp Val Ile
865 870 875 880

Ile Asn Ser Gly Asn Leu Thr Ala Gly Gly Asn Ile Val Asn Ile Ala
885 890 895

Gly Asn Leu Thr Val Glu Ser Asn Ala Asn Phe Lys Ala Ile Thr Asn
900 905 910

Phe Thr Phe Asn Val Gly Gly Leu Phe Asp Asn Lys Gly Asn Ser Asn
915 920 925

Ile Ser Ile Ala Lys Gly Gly Ala Arg Phe Lys Asp Ile Asp Asn Ser
930 935 940

Lys Asn Leu Ser Ile Thr Thr Asn Ser Ser Ser Thr Tyr Arg Thr Ile
945 950 955 960

Ile Ser Gly Asn Ile Thr Asn Lys Asn Gly Asp Leu Asn Ile Thr Asn
965 970 975

Glu Gly Ser Asp Thr Glu Met Gln Ile Gly Gly Asp Val Ser Gln Lys
980 985 990

Glu Gly Asn Leu Thr Ile Ser Ser Asp Lys Ile Asn Ile Thr Lys Gln
995 1000 1005

Ile Thr Ile Lys Ala Gly Val Asp Gly Glu Asn Ser Asp Ser Asp Ala
1010 1015 1020

Thr Asn Asn Ala Asn Leu Thr Ile Lys Thr Lys Glu Leu Lys Leu Thr
1025 1030 1035 1040

Gln Asp Leu Asn Ile Ser Gly Phe Asn Lys Ala Glu Ile Thr Ala Lys
1045 1050 1055

Asp Gly Ser Asp Leu Thr Ile Gly Asn Thr Asn Ser Ala Asp Gly Thr
1060 1065 1070

Asn Ala Lys Lys Val Thr Phe Asn Gln Val Lys Asp Ser Lys Ile Ser
1075 1080 1085

Ala Asp Gly His Lys Val Thr Leu His Ser Lys Val Glu Thr Ser Gly
1090 1095 1100

Ser Asn Asn Asn Thr Glu Asp Ser Ser Asp Asn Asn Ala Gly Leu Thr
1105 1110 1115 1120

Ile Asp Ala Lys Asn Val Thr Val Asn Asn Asn Ile Thr Ser His Lys
1125 1130 1135

Ala Val Ser Ile Ser Ala Thr Ser Gly Glu Ile Thr Thr Lys Thr Gly
1140 1145 1150

Thr Thr Ile Asn Ala Thr Thr Gly Asn Val Glu Ile Thr Ala Gln Thr
1155 1160 1165

Gly Ser Ile Leu Gly Gly Ile Glu Ser Ser Ser Gly Ser Val Thr Leu
1170 1175 1180

Thr Ala Thr Glu Gly Ala Leu Ala Val Ser Asn Ile Ser Gly Asn Thr
1185 1190 1195 1200

Val Thr Val Thr Ala Asn Ser Gly Ala Leu Thr Thr Leu Ala Gly Ser
1205 1210 1215

-continued

Thr Ile Lys Gly Thr Glu Ser Val Thr Thr Ser Ser Gln Ser Gly Asp
1220 1225 1230

Ile Gly Gly Thr Ile Ser Gly Gly Thr Val Glu Val Lys Ala Thr Glu
1235 1240 1245

Ser Leu Thr Thr Gln Ser Asn Ser Lys Ile Lys Ala Thr Thr Gly Glu
1250 1255 1260

Ala Asn Val Thr Ser Ala Thr Gly Thr Ile Gly Gly Thr Ile Ser Gly
1265 1270 1275 1280

Asn Thr Val Asn Val Thr Ala Asn Ala Gly Asp Leu Thr Val Gly Asn
1285 1290 1295

Gly Ala Glu Ile Asn Ala Thr Glu Gly Ala Ala Thr Leu Thr Thr Ser
1300 1305 1310

Ser Gly Lys Leu Thr Thr Glu Ala Ser Ser His Ile Thr Ser Ala Lys
1315 1320 1325

Gly Gln Val Asn Leu Ser Ala Gln Asp Gly Ser Val Ala Gly Ser Ile
1330 1335 1340

Asn Ala Ala Asn Val Thr Leu Asn Thr Thr Gly Thr Leu Thr Thr Val
1345 1350 1355 1360

Lys Gly Ser Asn Ile Asn Ala Thr Ser Gly Thr Leu Val Ile Asn Ala
1365 1370 1375

Lys Asp Ala Glu Leu Asn Gly Ala Ala Leu Gly Asn His Thr Val Val
1380 1385 1390

Asn Ala Thr Asn Ala Asn Gly Ser Gly Ser Val Ile Ala Thr Thr Ser
1395 1400 1405

Ser Arg Val Asn Ile Thr Gly Asp Leu Ile Thr Ile Asn Gly Leu Asn
1410 1415 1420

Ile Ile Ser Lys Asn Gly Ile Asn Thr Val Leu Leu Lys Gly Val Lys
1425 1430 1435 1440

Ile Asp Val Lys Tyr Ile Gln Pro Gly Ile Ala Ser Val Asp Glu Val
1445 1450 1455

Ile Glu Ala Lys Arg Ile Leu Glu Lys Val Lys Asp Leu Ser Asp Glu
1460 1465 1470

Glu Arg Glu Ala Leu Ala Lys Leu Gly Val Ser Ala Val Arg Phe Ile
1475 1480 1485

Glu Pro Asn Asn Thr Ile Thr Val Asp Thr Gln Asn Glu Phe Ala Thr
1490 1495 1500

Arg Pro Leu Ser Arg Ile Val Ile Ser Glu Gly Arg Ala Cys Phe Ser
1505 1510 1515 1520

Asn Ser Asp Gly Ala Thr Val Cys Val Asn Ile Ala Asp Asn Gly Arg
1525 1530 1535

( 2 ) INFORMATION FOR SEQ ID NO:3:

( i ) SEQUENCE CHARACTERISTICS:
( A ) LENGTH: 4937 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:3:

TAAATATACA AGATAATAAA AATAAATCAA GATTTTTGTG ATGACAAACA ACAATTACAA 60

CACCTTTTTT GCAGTCTATA TGCAAATATT TTAAAAAAAT AGTATAAATC CGCCATATAA 120

AATGGTATAA TCTTTCATCT TTCATCTTTA ATCTTTCATC TTTCATCTTT CATCTTTCAT 180

CTTTCATCTT TCATCTTTCA TCTTTCATCT TTCATCTTTC ATCTTTCATC TTTCATCTTT 240

-continued

| | | | | | | |
|---|---|---|---|---|---|---|
| CACATGAAAT | GATGAACCGA | GGGAAGGGAG | GGAGGGGCAA | GAATGAAGAG | GGAGCTGAAC | 300 |
| GAACGCAAAT | GATAAAGTAA | TTTAATTGTT | CAACTAACCT | TAGGAGAAAA | TATGAACAAG | 360 |
| ATATATCGTC | TCAAATTCAG | CAAACGCCTG | AATGCTTTGG | TTGCTGTGTC | TGAATTGGCA | 420 |
| CGGGGTTGTG | ACCATTCCAC | AGAAAAAGGC | TTCCGCTATG | TTACTATCTT | TAGGTGTAAC | 480 |
| CACTTAGCGT | TAAAGCCACT | TTCCGCTATG | TTACTATCTT | TAGGTGTAAC | ATCTATTCCA | 540 |
| CAATCTGTTT | TAGCAAGCGG | CTTACAAGGA | ATGGATGTAG | TACACGGCAC | AGCCACTATG | 600 |
| CAAGTAGATG | GTAATAAAAC | CATTATCCGC | AACAGTGTTG | ACGCTATCAT | TAATTGGAAA | 660 |
| CAATTTAACA | TCGACCAAAA | TGAAATGGTG | CAGTTTTTAC | AAGAAAACAA | CAACTCCGCC | 720 |
| GTATTCAACC | GTGTTACATC | TAACCAAATC | TCCCAATTAA | AAGGGATTTT | AGATTCTAAC | 780 |
| GGACAAGTCT | TTTTAATCAA | CCCAAATGGT | ATCACAATAG | GTAAAGACGC | AATTATTAAC | 840 |
| ACTAATGGCT | TTACGGCTTC | TACGCTAGAC | ATTTCTAACG | AAAACATCAA | GGCGCGTAAT | 900 |
| TTCACCTTCG | AGCAAACCAA | AGATAAAGCG | CTCGCTGAAA | TTGTGAATCA | CGGTTTAATT | 960 |
| ACTGTCGGTA | AAGACGGCAG | TGTAAATCTT | ATTGGTGGCA | AAGTGAAAAA | CGAGGGTGTG | 1020 |
| ATTAGCGTAA | ATGGTGGCAG | CATTTCTTTA | CTCGCAGGGC | AAAAAATCAC | CATCAGCGAT | 1080 |
| ATAATAAACC | CAACCATTAC | TTACAGCATT | GCCGCGCCTG | AAAATGAAGC | GGTCAATCTG | 1140 |
| GGCGATATTT | TTGCCAAAGG | CGGTAACATT | AATGTCCGTG | CTGCCACTAT | TCGAAACCAA | 1200 |
| GGTAAACTTT | CTGCTGATTC | TGTAAGCAAA | GATAAAAGCG | GCAATATTGT | TCTTTCCGCC | 1260 |
| AAAGAGGGTG | AAGCGGAAAT | TGGCGGTGTA | ATTTCCGCTC | AAAATCAGCA | AGCTAAAGGC | 1320 |
| GGCAAGCTGA | TGATTACAGG | CGATAAAGTC | ACATTAAAAA | CAGGTGCAGT | TATCGACCTT | 1380 |
| TCAGGTAAAG | AAGGGGGAGA | AACTTACCTT | GGCGGTGACG | AGCGCGGCGA | AGGTAAAAAC | 1440 |
| GGCATTCAAT | TAGCAAAGAA | AACCTCTTTA | GAAAAAGGCT | CAACCATCAA | TGTATCAGGC | 1500 |
| AAAGAAAAAG | GCGGACGCGC | TATTGTGTGG | GGCGATATTG | CGTTAATTGA | CGGCAATATT | 1560 |
| AACGCTCAAG | GTAGTGGTGA | TATCGCTAAA | ACCGGTGGTT | TTGTGGAGAC | ATCGGGGCAT | 1620 |
| TATTTATCCA | TTGACAGCAA | TGCAATTGTT | AAAACAAAAG | AGTGGTTGCT | AGACCCTGAT | 1680 |
| GATGTAACAA | TTGAAGCCGA | AGACCCCCTT | CGCAATAATA | CCGGTATAAA | TGATGAATTC | 1740 |
| CCAACAGGCA | CCGGTGAAGC | AAGCGACCCT | AAAAAAAATA | GCGAACTCAA | AACAACGCTA | 1800 |
| ACCAATACAA | CTATTTCAAA | TTATCTGAAA | AACGCCTGGA | CAATGAATAT | AACGGCATCA | 1860 |
| AGAAAACTTA | CCGTTAATAG | CTCAATCAAC | ATCGGAAGCA | ACTCCCACTT | AATTCTCCAT | 1920 |
| AGTAAAGGTC | AGCGTGGCGG | AGGCGTTCAG | ATTGATGGAG | ATATTACTTC | TAAAGGCGGA | 1980 |
| AATTTAACCA | TTTATTCTGG | CGGATGGGTT | GATGTTCATA | AAAATATTAC | GCTTGATCAG | 2040 |
| GGTTTTTTAA | ATATTACCGC | CGCTTCCGTA | GCTTTTGAAG | GTGGAAATAA | CAAAGCACGC | 2100 |
| GACGCGGCAA | ATGCTAAAAT | TGTCGCCCAG | GGCACTGTAA | CCATTACAGG | AGAGGGAAAA | 2160 |
| GATTTCAGGG | CTAACAACGT | ATCTTTAAAC | GGAACGGGTA | AAGGTCTGAA | TATCATTTCA | 2220 |
| TCAGTGAATA | ATTTAACCCA | CAATCTTAGT | GGCACAATTA | ACATATCTGG | GAATATAACA | 2280 |
| ATTAACCAAA | CTACGAGAAA | GAACACCTCG | TATTGGCAAA | CCAGCCATGA | TTCGCACTGG | 2340 |
| AACGTCAGTG | CTCTTAATCT | AGAGACAGGC | GCAAATTTTA | CCTTTATTAA | ATACATTTCA | 2400 |
| AGCAATAGCA | AAGGCTTAAC | AACACAGTAT | AGAAGCTCTG | CAGGGGTGAA | TTTTAACGGC | 2460 |
| GTAAATGGCA | ACATGTCATT | CAATCTCAAA | GAAGGAGCGA | AAGTTAATTT | CAAATTAAAA | 2520 |
| CCAAACGAGA | ACATGAACAC | AAGCAAACCT | TTACCAATTC | GGTTTTTAGC | CAATATCACA | 2580 |
| GCCACTGGTG | GGGGCTCTGT | TTTTTTTGAT | ATATATGCCA | ACCATTCTGG | CAGAGGGGCT | 2640 |

-continued

GAGTTAAAAA TGAGTGAAAT TAATATCTCT AACGGCGCTA ATTTTACCTT AAATTCCCAT 2700
GTTCGCGGCG ATGACGCTTT TAAAATCAAC AAAGACTTAA CCATAAATGC AACCAATTCA 2760
AATTTCAGCC TCAGACAGAC GAAAGATGAT TTTTATGACG GGTACGCACG CAATGCCATC 2820
AATTCAACCT ACAACATATC CATTCTGGGC GGTAATGTCA CCCTTGGTGG ACAAAACTCA 2880
AGCAGCAGCA TTACGGGGAA TATTACTATC GAGAAAGCAG CAAATGTTAC GCTAGAAGCC 2940
AATAACGCCC CTAATCAGCA AAACATAAGG GATAGAGTTA TAAAACTTGG CAGCTTGCTC 3000
GTTAATGGGA GTTTAAGTTT AACTGGCGAA AATGCAGATA TTAAAGGCAA TCTCACTATT 3060
TCAGAAAGCG CCACTTTTAA AGGAAAGACT AGAGATACCC TAAATATCAC CGGCAATTTT 3120
ACCAATAATG GCACTGCCGA AATTAATATA ACACAAGGAG TGGTAAAACT TGGCAATGTT 3180
ACCAATGATG GTGATTTAAA CATTACCACT CACGCTAAAC GCAACCAAAG AAGCATCATC 3240
GGCGGAGATA TAATCAACAA AAAAGGAAGC TTAAATATTA CAGACAGTAA TAATGATGCT 3300
GAAATCCAAA TTGGCGGCAA TATCTCGCAA AAAGAAGGCA ACCTCACGAT TTCTTCCGAT 3360
AAAATTAATA TCACCAAACA GATAACAATC AAAAAGGGTA TTGATGGAGA GGACTCTAGT 3420
TCAGATGCGA CAAGTAATGC CAACCTAACT ATTAAAACCA AAGAATTGAA ATTGACAGAA 3480
GACCTAAGTA TTTCAGGTTT CAATAAAGCA GAGATTACAG CCAAAGATGG TAGAGATTTA 3540
ACTATTGGCA ACAGTAATGA CGGTAACAGC GGTGCCGAAG CCAAAACAGT AACTTTTAAC 3600
AATGTTAAAG ATTCAAAAAT CTCTGCTGAC GGTCACAATG TGACACTAAA TAGCAAAGTG 3660
AAAACATCTA GCAGCAATGG CGGACGTGAA AGCAATAGCG ACAACGATAC CGGCTTAACT 3720
ATTACTGCAA AAAATGTAGA AGTAAACAAA GATATTACTT CTCTCAAAAC AGTAAATATC 3780
ACCGCGTCGG AAAAGGTTAC CACCACAGCA GGCTCGACCA TTAACGCAAC AAATGGCAAA 3840
GCAAGTATTA CAACCAAAAC AGGTGATATC AGCGGTACGA TTTCCGGTAA CACGGTAAGT 3900
GTTAGCGCGA CTGGTGATTT AACCACTAAA TCCGGCTCAA AAATTGAAGC GAAATCGGGT 3960
GAGGCTAATG TAACAAGTGC AACAGGTACA ATTGGCGGTA CAATTTCCGG TAATACGGTA 4020
AATGTTACGG CAAACGCTGG CGATTTAACA GTTGGGAATG GCGCAGAAAT TAATGCGACA 4080
GAAGGAGCTG CAACCTTAAC CGCAACAGGG AATACCTTGA CTACTGAAGC CGGTTCTAGC 4140
ATCACTTCAA CTAAGGGTCA GGTAGACCTC TTGGCTCAGA ATGGTAGCAT CGCAGGAAGC 4200
ATTAATGCTG CTAATGTGAC ATTAAATACT ACAGGCACCT TAACCACCGT GGCAGGCTCG 4260
GATATTAAAG CAACCAGCGG CACCTTGGTT ATTAACGCAA AAGATGCTAA GCTAAATGGT 4320
GATGCATCAG GTGATAGTAC AGAAGTGAAT GCAGTCAACG CAAGCGGCTC TGGTAGTGTG 4380
ACTGCGGCAA CCTCAAGCAG TGTGAATATC ACTGGGGATT TAAACACAGT AAATGGGTTA 4440
AATATCATTT CGAAAGATGG TAGAAACACT GTGCGCTTAA GAGGCAAGGA AATTGAGGTG 4500
AAATATATCC AGCCAGGTGT AGCAAGTGTA GAAGAAGTAA TTGAAGCGAA ACGCGTCCTT 4560
GAAAAAGTAA AAGATTTATC TGATGAAGAA AGAGAAACAT TAGCTAAACT TGGTGTAAGT 4620
GCTGTACGTT TTGTTGAGCC AAATAATACA ATTACAGTCA ATACACAAAA TGAATTTACA 4680
ACCAGACCGT CAAGTCAAGT GATAATTTCT GAAGGTAAGG CGTGTTTCTC AAGTGGTAAT 4740
GGCGCACGAG TATGTACCAA TGTTGCTGAC GATGGACAGC CGTAGTCAGT AATTGACAAG 4800
GTAGATTTCA TCCTGCAATG AAGTCATTTT ATTTTCGTAT TATTTACTGT GTGGGTTAAA 4860
GTTCAGTACG GGCTTTACCC ATCTTGTAAA AAATTACGGA GAATACAATA AAGTATTTTT 4920
AACAGGTTAT TATTATG 4937

( 2 ) INFORMATION FOR SEQ ID NO:4:

( i ) SEQUENCE CHARACTERISTICS:
( A ) LENGTH: 1477 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:4:

| | | | | | | | | | | | | | | | |
|---|---|---|---|---|---|---|---|---|---|---|---|---|---|---|---|
| Met | Asn | Lys | Ile | Tyr | Arg | Leu | Lys | Phe | Ser | Lys | Arg | Leu | Asn | Ala | Leu |
| 1 | | | | 5 | | | | | 10 | | | | | 15 | |
| Val | Ala | Val | Ser | Glu | Leu | Ala | Arg | Gly | Cys | Asp | His | Ser | Thr | Glu | Lys |
| | | | 20 | | | | | 25 | | | | | 30 | | |
| Gly | Ser | Glu | Lys | Pro | Ala | Arg | Met | Lys | Val | Arg | His | Leu | Ala | Leu | Lys |
| | | 35 | | | | | 40 | | | | | 45 | | | |
| Pro | Leu | Ser | Ala | Met | Leu | Leu | Ser | Leu | Gly | Val | Thr | Ser | Ile | Pro | Gln |
| | 50 | | | | | 55 | | | | | 60 | | | | |
| Ser | Val | Leu | Ala | Ser | Gly | Leu | Gln | Gly | Met | Asp | Val | Val | His | Gly | Thr |
| 65 | | | | | 70 | | | | | 75 | | | | | 80 |
| Ala | Thr | Met | Gln | Val | Asp | Gly | Asn | Lys | Thr | Ile | Ile | Arg | Asn | Ser | Val |
| | | | | 85 | | | | | 90 | | | | | 95 | |
| Asp | Ala | Ile | Ile | Asn | Trp | Lys | Gln | Phe | Asn | Ile | Asp | Gln | Asn | Glu | Met |
| | | | 100 | | | | | 105 | | | | | 110 | | |
| Val | Gln | Phe | Leu | Gln | Glu | Asn | Asn | Asn | Ser | Ala | Val | Phe | Asn | Arg | Val |
| | | 115 | | | | | 120 | | | | | 125 | | | |
| Thr | Ser | Asn | Gln | Ile | Ser | Gln | Leu | Lys | Gly | Ile | Leu | Asp | Ser | Asn | Gly |
| | 130 | | | | | 135 | | | | | 140 | | | | |
| Gln | Val | Phe | Leu | Ile | Asn | Pro | Asn | Gly | Ile | Thr | Ile | Gly | Lys | Asp | Ala |
| 145 | | | | | 150 | | | | | 155 | | | | | 160 |
| Ile | Ile | Asn | Thr | Asn | Gly | Phe | Thr | Ala | Ser | Thr | Leu | Asp | Ile | Ser | Asn |
| | | | | 165 | | | | | 170 | | | | | 175 | |
| Glu | Asn | Ile | Lys | Ala | Arg | Asn | Phe | Thr | Phe | Glu | Gln | Thr | Lys | Asp | Lys |
| | | | 180 | | | | | 185 | | | | | 190 | | |
| Ala | Leu | Ala | Glu | Ile | Val | Asn | His | Gly | Leu | Ile | Thr | Val | Gly | Lys | Asp |
| | | 195 | | | | | 200 | | | | | 205 | | | |
| Gly | Ser | Val | Asn | Leu | Ile | Gly | Gly | Lys | Val | Lys | Asn | Glu | Gly | Val | Ile |
| | 210 | | | | | 215 | | | | | 220 | | | | |
| Ser | Val | Asn | Gly | Gly | Ser | Ile | Ser | Leu | Leu | Ala | Gly | Gln | Lys | Ile | Thr |
| 225 | | | | | 230 | | | | | 235 | | | | | 240 |
| Ile | Ser | Asp | Ile | Ile | Asn | Pro | Thr | Ile | Thr | Tyr | Ser | Ile | Ala | Ala | Pro |
| | | | | 245 | | | | | 250 | | | | | 255 | |
| Glu | Asn | Glu | Ala | Val | Asn | Leu | Gly | Asp | Ile | Phe | Ala | Lys | Gly | Gly | Asn |
| | | | 260 | | | | | 265 | | | | | 270 | | |
| Ile | Asn | Val | Arg | Ala | Ala | Thr | Ile | Arg | Asn | Gln | Gly | Lys | Leu | Ser | Ala |
| | | 275 | | | | | 280 | | | | | 285 | | | |
| Asp | Ser | Val | Ser | Lys | Asp | Lys | Ser | Gly | Asn | Ile | Val | Leu | Ser | Ala | Lys |
| | 290 | | | | | 295 | | | | | 300 | | | | |
| Glu | Gly | Glu | Ala | Glu | Ile | Gly | Gly | Val | Ile | Ser | Ala | Gln | Asn | Gln | Gln |
| 305 | | | | | 310 | | | | | 315 | | | | | 320 |
| Ala | Lys | Gly | Gly | Lys | Leu | Met | Ile | Thr | Gly | Asp | Lys | Val | Thr | Leu | Lys |
| | | | | 325 | | | | | 330 | | | | | 335 | |
| Thr | Gly | Ala | Val | Ile | Asp | Leu | Ser | Gly | Lys | Glu | Gly | Gly | Glu | Thr | Tyr |
| | | | 340 | | | | | 345 | | | | | 350 | | |
| Leu | Gly | Gly | Asp | Glu | Arg | Gly | Glu | Gly | Lys | Asn | Gly | Ile | Gln | Leu | Ala |
| | | 355 | | | | | 360 | | | | | 365 | | | |

-continued

| | | | | | | | | | | | | | | | |
|---|---|---|---|---|---|---|---|---|---|---|---|---|---|---|---|
| Lys | Lys | Thr | Scr | Lcu | Glu | Lys | Gly | Scr | Thr | Ilc | Asn | Val | Scr | Gly | Lys |
| | 370 | | | | | 375 | | | | | 380 | | | | |
| Glu | Lys | Gly | Gly | Phc | Ala | Ilc | Val | Trp | Gly | Asp | Ilc | Ala | Lcu | Ilc | Asp |
| 385 | | | | | 390 | | | | | 395 | | | | | 400 |
| Gly | Asn | Ilc | Asn | Ala | Gln | Gly | Scr | Gly | Asp | Ilc | Ala | Lys | Thr | Gly | Gly |
| | | | | 405 | | | | | 410 | | | | | 415 | |
| Phc | Val | Glu | Thr | Scr | Gly | His | Asp | Lcu | Phc | Ilc | Lys | Asp | Asn | Ala | Ilc |
| | | | 420 | | | | | 425 | | | | | 430 | | |
| Val | Asp | Ala | Lys | Glu | Trp | Lcu | Lcu | Asp | Phc | Asp | Asn | Val | Scr | Ilc | Asn |
| | | 435 | | | | | 440 | | | | | 445 | | | |
| Ala | Glu | Asp | Pro | Lcu | Phc | Asn | Asn | Thr | Gly | Ilc | Asn | Asp | Glu | Phc | Pro |
| | 450 | | | | | 455 | | | | | 460 | | | | |
| Thr | Gly | Thr | Gly | Glu | Ala | Scr | Asp | Pro | Lys | Lys | Asn | Scr | Glu | Lcu | Lys |
| 465 | | | | | 470 | | | | | 475 | | | | | 480 |
| Thr | Thr | Lcu | Thr | Asn | Thr | Thr | Ilc | Scr | Asn | Tyr | Lcu | Lys | Asn | Ala | Trp |
| | | | | 485 | | | | | 490 | | | | | 495 | |
| Thr | Mct | Asn | Ilc | Thr | Ala | Scr | Arg | Lys | Lcu | Thr | Val | Asn | Scr | Scr | Ilc |
| | | | 500 | | | | | 505 | | | | | 510 | | |
| Asn | Ilc | Gly | Scr | Asn | Scr | His | Lcu | Ilc | Lcu | His | Scr | Lys | Gly | Gln | Arg |
| | | 515 | | | | | 520 | | | | | 525 | | | |
| Gly | Gly | Gly | Val | Gln | Ilc | Asp | Gly | Asp | Ilc | Thr | Scr | Lys | Gly | Gly | Asn |
| | 530 | | | | | 535 | | | | | 540 | | | | |
| Lcu | Thr | Ilc | Tyr | Scr | Gly | Gly | Trp | Val | Asp | Val | His | Lys | Asn | Ilc | Thr |
| 545 | | | | | 550 | | | | | 555 | | | | | 560 |
| Lcu | Asp | Gln | Gly | Phc | Lcu | Asn | Ilc | Thr | Ala | Ala | Scr | Val | Ala | Phc | Glu |
| | | | | 565 | | | | | 570 | | | | | 575 | |
| Gly | Gly | Asn | Asn | Lys | Ala | Arg | Asp | Ala | Ala | Asn | Ala | Lys | Ilc | Val | Ala |
| | | | 580 | | | | | 585 | | | | | 590 | | |
| Gln | Gly | Thr | Val | Thr | Ilc | Thr | Gly | Glu | Gly | Lys | Asp | Phc | Arg | Ala | Asn |
| | | 595 | | | | | 600 | | | | | 605 | | | |
| Asn | Val | Scr | Lcu | Asn | Gly | Thr | Gly | Lys | Gly | Lcu | Asn | Ilc | Ilc | Scr | Scr |
| | 610 | | | | | 615 | | | | | 620 | | | | |
| Val | Asn | Asn | Lcu | Thr | His | Asn | Lcu | Scr | Gly | Thr | Ilc | Asn | Ilc | Scr | Gly |
| 625 | | | | | 630 | | | | | 635 | | | | | 640 |
| Asn | Ilc | Thr | Ilc | Asn | Gln | Thr | Thr | Arg | Lys | Asn | Thr | Scr | Tyr | Trp | Gln |
| | | | | 645 | | | | | 650 | | | | | 655 | |
| Thr | Scr | His | Asp | Scr | His | Trp | Asn | Val | Scr | Ala | Lcu | Asn | Lcu | Glu | Thr |
| | | | 660 | | | | | 665 | | | | | 670 | | |
| Gly | Ala | Asn | Phc | Thr | Phc | Ilc | Lys | Tyr | Ilc | Scr | Scr | Asn | Scr | Lys | Gly |
| | | 675 | | | | | 680 | | | | | 685 | | | |
| Lcu | Thr | Thr | Gln | Tyr | Arg | Scr | Scr | Ala | Gly | Val | Asn | Phc | Asn | Gly | Val |
| | 690 | | | | | 695 | | | | | 700 | | | | |
| Asn | Gly | Asn | Mct | Scr | Phc | Asn | Lcu | Lys | Glu | Gly | Ala | Lys | Val | Asn | Phc |
| 705 | | | | | 710 | | | | | 715 | | | | | 720 |
| Lys | Lcu | Lys | Pro | Asn | Glu | Asn | Mct | Asn | Thr | Scr | Lys | Pro | Lcu | Pro | Ilc |
| | | | | 725 | | | | | 730 | | | | | 735 | |
| Arg | Phc | Lcu | Ala | Asn | Ilc | Thr | Ala | Thr | Gly | Gly | Gly | Scr | Val | Phc | Phc |
| | | | 740 | | | | | 745 | | | | | 750 | | |
| Asp | Ilc | Tyr | Ala | Asn | His | Scr | Gly | Arg | Gly | Ala | Glu | Lcu | Lys | Mct | Scr |
| | | 755 | | | | | 760 | | | | | 765 | | | |
| Glu | Ilc | Asn | Ilc | Scr | Asn | Gly | Ala | Asn | Phc | Thr | Lcu | Asn | Scr | His | Val |
| | 770 | | | | | 775 | | | | | 780 | | | | |
| Arg | Gly | Asp | Asp | Ala | Phc | Lys | Ilc | Asn | Lys | Asp | Lcu | Thr | Ilc | Asn | Ala |

-continued 785 790 795 800

Thr Asn Ser Asn Phe Ser Leu Arg Gln Thr Lys Asp Asp Phe Tyr Asp
805 810 815

Gly Tyr Ala Arg Asn Ala Ile Asn Ser Thr Tyr Asn Ile Ser Ile Leu
820 825 830

Gly Gly Asn Val Thr Leu Gly Gly Gln Asn Ser Ser Ser Ser Ile Thr
835 840 845

Gly Asn Ile Thr Ile Glu Lys Ala Ala Asn Val Thr Leu Glu Ala Asn
850 855 860

Asn Ala Pro Asn Gln Gln Asn Ile Arg Asp Arg Val Ile Lys Leu Gly
865 870 875 880

Ser Leu Leu Val Asn Gly Ser Leu Ser Leu Thr Gly Glu Asn Ala Asp
885 890 895

Ile Lys Gly Asn Leu Thr Ile Ser Glu Ser Ala Thr Phe Lys Gly Lys
900 905 910

Thr Arg Asp Thr Leu Asn Ile Thr Gly Asn Phe Thr Asn Asn Gly Thr
915 920 925

Ala Glu Ile Asn Ile Thr Gln Gly Val Val Lys Leu Gly Asn Val Thr
930 935 940

Asn Asp Gly Asp Leu Asn Ile Thr Thr His Ala Lys Arg Asn Gln Arg
945 950 955 960

Ser Ile Ile Gly Gly Asp Ile Ile Asn Lys Lys Gly Ser Leu Asn Ile
965 970 975

Thr Asp Ser Asn Asn Asp Ala Glu Ile Gln Ile Gly Gly Asn Ile Ser
980 985 990

Gln Lys Glu Gly Asn Leu Thr Ile Ser Ser Asp Lys Ile Asn Ile Thr
995 1000 1005

Lys Gln Ile Thr Ile Lys Lys Gly Ile Asp Gly Glu Asp Ser Ser Ser
1010 1015 1020

Asp Ala Thr Ser Asn Ala Asn Leu Thr Ile Lys Thr Lys Glu Leu Lys
1025 1030 1035 1040

Leu Thr Glu Asp Leu Ser Ile Ser Gly Phe Asn Lys Ala Glu Ile Thr
1045 1050 1055

Ala Lys Asp Gly Arg Asp Leu Thr Ile Gly Asn Ser Asn Asp Gly Asn
1060 1065 1070

Ser Gly Ala Glu Ala Lys Thr Val Thr Phe Asn Asn Val Lys Asp Ser
1075 1080 1085

Lys Ile Ser Ala Asp Gly His Asn Val Thr Leu Asn Ser Lys Val Lys
1090 1095 1100

Thr Ser Ser Ser Asn Gly Gly Arg Glu Ser Asn Ser Asp Asn Asp Thr
1105 1110 1115 1120

Gly Leu Thr Ile Thr Ala Lys Asn Val Glu Val Asn Lys Asp Ile Thr
1125 1130 1135

Ser Leu Lys Thr Val Asn Ile Thr Ala Ser Glu Lys Val Thr Thr Thr
1140 1145 1150

Ala Gly Ser Thr Ile Asn Ala Thr Asn Gly Lys Ala Ser Ile Thr Thr
1155 1160 1165

Lys Thr Gly Asp Ile Ser Gly Thr Ile Ser Gly Asn Thr Val Ser Val
1170 1175 1180

Ser Ala Thr Val Asp Leu Thr Thr Lys Ser Gly Ser Lys Ile Glu Ala
1185 1190 1195 1200

Lys Ser Gly Glu Ala Asn Val Thr Ser Ala Thr Gly Thr Ile Gly Gly
1205 1210 1215

-continued

```
Thr Ile Ser Gly Asn Thr Val Asn Val Thr Ala Asn Ala Gly Asp Leu
            1220                1225                1230

Thr Val Gly Asn Gly Ala Glu Ile Asn Ala Thr Glu Gly Ala Ala Thr
        1235                1240                1245

Leu Thr Ala Thr Gly Asn Thr Leu Thr Thr Glu Ala Gly Ser Ser Ile
    1250                1255                1260

Thr Ser Thr Lys Gly Gln Val Asp Leu Leu Ala Gln Asn Gly Ser Ile
1265                1270                1275                1280

Ala Gly Ser Ile Asn Ala Ala Asn Val Thr Leu Asn Thr Thr Gly Thr
                1285                1290                1295

Leu Thr Thr Val Ala Gly Ser Asp Ile Lys Ala Thr Ser Gly Thr Leu
            1300                1305                1310

Val Ile Asn Ala Lys Asp Ala Lys Leu Asn Gly Asp Ala Ser Gly Asp
        1315                1320                1325

Ser Thr Glu Val Asn Ala Val Asn Ala Ser Gly Ser Gly Ser Val Thr
    1330                1335                1340

Ala Ala Thr Ser Ser Ser Val Asn Ile Thr Gly Asp Leu Asn Thr Val
1345                1350                1355                1360

Asn Gly Leu Asn Ile Ile Ser Lys Asp Gly Arg Asn Thr Val Arg Leu
                1365                1370                1375

Arg Gly Lys Glu Ile Glu Val Lys Tyr Ile Gln Pro Gly Val Ala Ser
            1380                1385                1390

Val Glu Glu Val Ile Glu Ala Lys Arg Val Leu Glu Lys Val Lys Asp
        1395                1400                1405

Leu Ser Asp Glu Glu Arg Glu Thr Leu Ala Lys Leu Gly Val Ser Ala
    1410                1415                1420

Val Arg Phe Val Glu Pro Asn Asn Thr Ile Thr Val Asn Thr Gln Asn
1425                1430                1435                1440

Glu Phe Thr Thr Arg Pro Ser Ser Gln Val Ile Ile Ser Glu Gly Lys
                1445                1450                1455

Ala Cys Phe Ser Ser Gly Asn Gly Ala Arg Val Cys Thr Asn Val Ala
            1460                1465                1470

Asp Asp Gly Gln Pro
        1475
```

( 2 ) INFORMATION FOR SEQ ID NO:5:

( i ) SEQUENCE CHARACTERISTICS:
( A ) LENGTH: 9171 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:5:

```
ACAGCGTTCT CTTAATACTA GTACAAACCC ACAATAAAAT ATGACAAACA ACAATTACAA    60
CACCTTTTTT GCAGTCTATA TGCAAATATT TTAAAAAATA GTATAAATCC GCCATATAAA   120
ATGGTATAAT CTTTCATCTT TCATCTTTCA TCTTTCATCT TTCATCTTTC ATCTTTCATC   180
TTTCATCTTT CATCTTTCAT CTTTCATCTT TCATCTTTCA TCTTTCATCT TTCATCTTTC   240
ACATGAAATG ATGAACCGAG GGAAGGGAGG GAGGGGCAAG AATGAAGAGG GAGCTGAACG   300
AACGCAAATG ATAAAGTAAT TTAATTGTTC AACTAACCTT AGGAGAAAAT ATGAACAAGA   360
TATATCGTCT CAAATTCAGC AAACGCCTGA ATGCTTTGGT TGCTGTGTCT GAATTGGCAC   420
GGGGTTGTGA CCATTCCACA GAAAAAGGCA GCGAAAAACC TGCTCGCATG AAAGTGCGTC   480
```

-continued

| | | | | | | |
|---|---|---|---|---|---|---|
| ACTTAGCGTT | AAAGCCACTT | TCCGCTATGT | TACTATCTTT | AGGTGTAACA | TCTATTCCAC | 540 |
| AATCTGTTTT | AGCAAGCGGC | TTACAAGGAA | TGGATGTAGT | ACACGGCACA | GCCACTATGC | 600 |
| AAGTAGATGG | TAATAAAACC | ATTATCCGCA | ACAGTGTTGA | CGCTATCATT | AATTGGAAAC | 660 |
| AATTTAACAT | CGACCAAAAT | GAAATGGTGC | AGTTTTTACA | AGAAAACAAC | AACTCCGCCG | 720 |
| TATTCAACCG | TGTTACATCT | AACCAAATCT | CCCAATTAAA | AGGGATTTTA | GATTCTAACG | 780 |
| GACAAGTCTT | TTTAATCAAC | CCAAATGGTA | TCACAATAGG | TAAAGACGCA | ATTATTAACA | 840 |
| CTAATGGCTT | TACGGCTTCT | ACGCTAGACA | TTTCTAACGA | AAACATCAAG | GCGCGTAATT | 900 |
| TCACCTTCGA | GCAAACCAAA | GATAAAGCGC | TCGCTGAAAT | TGTGAATCAC | GGTTTAATTA | 960 |
| CTGTCGGTAA | AGACGGCAGT | GTAAATCTTA | TTGGTGGCAA | AGTGAAAAAC | GAGGGTGTGA | 1020 |
| TTAGCGTAAA | TGGTGGCAGC | ATTTCTTTAC | TCGCAGGGCA | AAAAATCACC | ATCAGCGATA | 1080 |
| TAATAAACCC | AACCATTACT | TACAGCATTG | CCGCGCCTGA | AAATGAAGCG | GTCAATCTGG | 1140 |
| GCGATATTTT | TGCCAAAGGC | GGTAACATTA | ATGTCCGTGC | TGCCACTATT | CGAAACCAAG | 1200 |
| CTTTCCGCCA | AAGAGGGTGA | AGCGGAAATT | GGCGGTGTAA | TTTCCGCTCA | AAATCAGCAA | 1260 |
| GCTAAAGGCG | GCAAGCTGAT | GATTACAGGC | GATAAAGTCA | CATTAAAAAC | AGGTGCAGTT | 1320 |
| ATCGACCTTT | CAGGTAAAGA | AGGGGGAGAA | ACTTACCTTG | GCGGTGACGA | GCGCGGCGAA | 1380 |
| GGTAAAAACG | GCATTCAATT | AGCAAAGAAA | ACCTCTTTAG | AAAAAGGCTC | AACCATCAAT | 1440 |
| GTATCAGGCA | AAGAAAAAGG | CGGACGCGCT | ATTGTGTGGG | GCGATATTGC | GTTAATTGAC | 1500 |
| GGCAATATTA | ACGCTCAAGG | TAGTGGTGAT | ATCGCTAAAA | CCGGTGGTTT | TGTGGAGACG | 1560 |
| TCGGGGCATG | ATTTATTCAT | CAAAGACAAT | GCAATTGTTG | ACGCCAAAGA | GTGGTTGTTA | 1620 |
| GACCCGGATA | ATGTATCTAT | TAATGCAGAA | ACAGCAGGAC | GCAGCAATAC | TTCAGAAGAC | 1680 |
| GATGAATACA | CGGGATCCGG | GAATAGTGCC | AGCACCCCAA | AACGAAACAA | AGAAAAGACA | 1740 |
| ACATTAACAA | ACACAACTCT | TGAGAGTATA | CTAAAAAAAG | GTACCTTTGT | TAACATCACT | 1800 |
| GCTAATCAAC | GCATCTATGT | CAATAGCTCC | ATTAATTTAT | CCAATGGCAG | CTTAACTCTT | 1860 |
| TGGAGTGAGG | GTCGGAGCGG | TGGCGGCGTT | GAGATTAACA | ACGATATTAC | CACCGGTGAT | 1920 |
| GATACCAGAG | GTGCAAACTT | AACAATTTAC | TCAGGCGGCT | GGGTTGATGT | TCATAAAAAT | 1980 |
| ATCTCACTCG | GGGCGCAAGG | TAACATAAAC | ATTACAGCTA | AACAAGATAT | CGCCTTTGAG | 2040 |
| AAAGGAAGCA | ACCAAGTCAT | TACAGGTCAA | GGGACTATTA | CCTCAGGCAA | TCAAAAAGGT | 2100 |
| TTTAGATTTA | ATAATGTCTC | TCTAAACGGC | ACTGGCAGCG | GACTGCAATT | CACCACTAAA | 2160 |
| AGAACCAATA | AATACGCTAT | CACAAATAAA | TTTGAAGGGA | CTTTAAATAT | TTCAGGGAAA | 2220 |
| GTGAACATCT | CAATGGTTTT | ACCTAAAAAT | GAAAGTGGAT | ATGATAAATT | CAAAGGACGC | 2280 |
| ACTTACTGGA | ATTTAACCTC | GAAAGTGGAT | ATGATAAATT | CAAAGGACGC | CCTCACTATT | 2340 |
| GACTCCAGAG | GAAGCGATAG | TGCAGGCACA | CTTACCCAGC | CTTATAATTT | AAACGGTATA | 2400 |
| TCATTCAACA | AAGACACTAC | CTTTAATGTT | GAACGAAATG | CAAGAGTCAA | CTTTGACATC | 2460 |
| AAGGCACCAA | TAGGGATAAA | TAAGTATTCT | AGTTTGAATT | ACGCATCATT | TAATGGAAAC | 2520 |
| ATTTCAGTTT | CGGGAGGGGG | GAGTGTTGAT | TTCACACTTC | TCGCCTCATC | CTCTAACGTC | 2580 |
| CAAACCCCCG | GTGTAGTTAT | AAATTCTAAA | TACTTTAATG | TTTCAACAGG | GTCAAGTTTA | 2640 |
| AGATTTAAAA | CTTCAGGCTC | AACAAAAACT | GGCTTCTCAA | TAGAGAAAGA | TTTAACTTTA | 2700 |
| AATGCCACCG | GAGGCAACAT | AACACTTTTG | CAAGTTGAAG | GCACCGATGG | AATGATTGGT | 2760 |
| AAAGGCATTG | TAGCCAAAAA | AAACATAACC | TTTGAAGGAG | GTAAGATGAG | GTTTGGCTCC | 2820 |
| AGGAAAGCCG | TAACAGAAAT | CGAAGGCAAT | GTTACTATCA | ATAACAACGC | TAACGTCACT | 2880 |

-continued

| | | | | | | |
|---|---|---|---|---|---|---|
| CTTATCGGTT | CGGATTTTGA | CAACCATCAA | AAACCTTTAA | CTATTAAAAA | AGATGTCATC | 2940 |
| ATTAATAGCG | GCAACCTTAC | CGCTGGAGGC | AATATTGTCA | ATATAGCCGG | AAATCTTACC | 3000 |
| GTTGAAAGTA | ACGCTAATTT | CAAAGCTATC | ACAAATTTCA | CTTTTAATGT | AGGCGGCTTG | 3060 |
| TTTGACAACA | AAGGCAATTC | AAATATTTCC | ATTGCCAAAG | GAGGGGCTCG | CTTTAAAGAC | 3120 |
| ATTGATAATT | CCAAGAATTT | AAGCATCACC | ACCAACTCCA | GCTCCACTTA | CCGCACTATT | 3180 |
| ATAAGCGGCA | ATATAACCAA | TAAAAACGGT | GATTTAAATA | TTACGAACGA | AGGTAGTGAT | 3240 |
| ACTGAAATGC | AAATTGGCGG | CGATGTCTCG | CAAAAAGAAG | GTAATCTCAC | GATTTCTTCT | 3300 |
| GACAAAATCA | ATATTACCAA | ACAGATAACA | ATCAAGGCAG | GTGTTGATGG | GGAGAATTCC | 3360 |
| GATTCAGACG | CGACAAACAA | TGCCAATCTA | ACCATTAAAA | CCAAAGAATT | GAAATTAACG | 3420 |
| CAAGACCTAA | ATATTTCAGG | TTTCAATAAA | GCAGAGATTA | CAGCTAAAGA | TGGTAGTGAT | 3480 |
| TTAACTATTG | GTAACACCAA | TAGTGCTGAT | GGTACTAATG | CCAAAAAAGT | AACCTTTAAC | 3540 |
| CAGGTTAAAG | ATTCAAAAAT | CTCTGCTGAC | GGTCACAAGG | TGACACTACA | CAGCAAAGTG | 3600 |
| GAAACATCCG | GTAGTAATAA | CAACACTGAA | GATAGCAGTG | ACAATAATGC | CGGCTTAACT | 3660 |
| ATCGATGCAA | AAAATGTAAC | AGTAAACAAC | AATATTACTT | CTCACAAAGC | AGTGAGCATC | 3720 |
| TCTGCGACAA | GTGGAGAAAT | TACCACTAAA | ACAGGTACAA | CCATTAACGC | AACCACTGGT | 3780 |
| AACGTGGAGA | TAACCGCTCA | AACAGGTAGT | ATCCTAGGTG | GAATTGAGTC | CAGCTCTGGC | 3840 |
| TCTGTAACAC | TTACTGCAAC | CGAGGGCGCT | CTTGCTGTAA | GCAATATTTC | GGGCAACACC | 3900 |
| GTTACTGTTA | CTGCAAATAG | CGGTGCATTA | ACCACTTTGG | CAGGCTCTAC | AATTAAAGGA | 3960 |
| ACCGAGAGTG | TAACCACTTC | AAGTCAATCA | GGCGATATCG | GCGGTACGAT | TTCTGGTGGC | 4020 |
| ACAGTAGAGG | TTAAAGCAAC | CGAAAGTTTA | ACCACTCAAT | CCAATTCAAA | AATTAAAGCA | 4080 |
| ACAACAGGCG | AGGCTAACGT | AACAAGTGCA | ACAGGTACAA | TTGGTGGTAC | GATTTCCGGT | 4140 |
| AATACGGTAA | ATGTTACGGC | AAACGCTGGC | GATTTAACAG | TTGGGAATGG | CGCAGAAATT | 4200 |
| AATGCGACAG | AAGGAGCTGC | AACCTTAACT | ACATCATCGG | GCAAATTAAC | TACCGAAGCT | 4260 |
| AGTTCACACA | TTACTTCAGC | CAAGGGTCAG | GTAAATCTTT | CAGCTCAGGA | TGGTAGCGTT | 4320 |
| GCAGGAAGTA | TTAATGCCGC | CAATGTGACA | CTAAATACTA | CAGGCACTTT | AACTACCGTG | 4380 |
| AAGGGTTCAA | ACATTAATGC | AACCAGCGGT | ACCTTGGTTA | TTAACGCAAA | AGACGCTGAG | 4440 |
| CTAAATGGCG | CAGCATTGGG | TAACCACACA | GTGGTAAATG | CAACCAACGC | AAATGGCTCC | 4500 |
| GGCAGCGTAA | TCGCGACAAC | CTCAAGCAGA | GTGAACATCA | CTGGGGATTT | AATCACAATA | 4560 |
| AATGGATTAA | ATATCATTTC | AAAAAACGGT | ATAAACACCG | TACTGTTAAA | AGGCGTTAAA | 4620 |
| ATTGATGTGA | AATACATTCA | ACCGGGTATA | GCAAGCGTAG | ATGAAGTAAT | TGAAGCGAAA | 4680 |
| CGCATCCTTG | AGAAGGTAAA | AGATTTATCT | GATGAAGAAA | GAGAAGCGTT | AGCTAAACTT | 4740 |
| GGCGTAAGTG | CTGTACGTTT | TATTGAGCCA | AATAATACAA | TTACAGTCGA | TACACAAAAT | 4800 |
| GAATTTGCAA | CCAGACCATT | AAGTCGAATA | GTGATTTCTG | AAGGCAGGGC | GTGTTTCTCA | 4860 |
| AACAGTGATG | GCGCGACGGT | GTGCGTTAAT | ATCGCTGATA | ACGGGCGGTA | GCGGTCAGTA | 4920 |
| ATTGACAAGG | TAGATTTCAT | CCTGCAATGA | AGTCATTTTA | TTTTCGTATT | ATTTACTGTG | 4980 |
| TGGGTTAAAG | TTCAGTACGG | GCTTTACCCA | TCTTGTAAAA | AATTACGGAG | AATACAATAA | 5040 |
| AGTATTTTTA | ACAGGTTATT | ATTATGAAAA | ATATAAAAAG | CAGATTAAAA | CTCAGTGCAA | 5100 |
| TATCAGTATT | GCTTGGCCTG | GCTTCTTCAT | CATTGTATGC | AGAAGAAGCG | TTTTTAGTAA | 5160 |
| AAGGCTTTCA | GTTATCTGGT | GCACTTGAAA | CTTTAAGTGA | AGACGCCCAA | CTGTCTGTAG | 5220 |
| CAAAATCTTT | ATCTAAATAC | CAAGGCTCGC | AAACTTTAAC | AAACCTAAAA | ACAGCACAGC | 5280 |

-continued

```
TTGAATTACA GGCTGTGCTA GATAAGATTG AGCCAAATAA GTTTGATGTG ATATTGCCAC   5340
AACAAACCAT TACGGATGGC AATATTATGT TTGAGCTAGT CTCGAAATCA GCCGCAGAAA   5400
GCCAAGTTTT TTATAAGGCG AGCCAGGGTT ATAGTGAAGA AAATATCGCT CGTAGCCTGC   5460
CATCTTTGAA ACAAGGAAAA GTGTATGAAG ATGGTCGTCA GTGGTTCGAT TTGCGTGAAT   5520
TCAATATGGC AAAAGAAAAT CCACTTAAAG TCACTCGCGT GCATTACGAG TTAAACCCTA   5580
AAAACAAAAC CTCTGATTTG GTAGTTGCAG GTTTTTCGCC TTTTGGCAAA ACGCGTAGCT   5640
TTGTTTCCTA TGATAATTTC GGCGCAAGGG AGTTTAACTA TCAACGTGTA AGTCTAGGTT   5700
TTGTAAATGC CAATTTGACC GGACATGATG ATGTATTAAA TCTAAACGCA TTGACCAATG   5760
TAAAAGCACC ATCAAAATCT TATGCGGTAG GCATAGGATA TACTTATCCG TTTTATGATA   5820
AACACCAATC CTTAAGTCTT TATACCAGCA TGAGTTATGC TGATTCTAAT GATATCGACG   5880
GCTTACCAAG TGCGATTAAT CGTAAATTAT CAAAAGGTCA ATCTATCTCT GCGAATCTGA   5940
AATGGAGTTA TTATCTCCCG ACATTTAACC TTGGAATGGA AGACCAGTTT AAAATTAATT   6000
TAGGCTACAA CTACCGCCAT ATTAATCAAA CATCCGAGTT AAACACCCTG GGTGCAACGA   6060
AGAAAAAATT TGCAGTATCA GGCGTAAGTG CAGGCATTGA TGGACATATC CAATTTACCC   6120
CTAAAACAAT CTTTAATATT GATTTAACTC ATCATTATTA CGCGAGTAAA TTACCAGGCT   6180
CTTTTGGAAT GGAGCGCATT GGCGAAACAT TTAATCGCAG CTATCACATT AGCACAGCCA   6240
GTTTAGGGTT GAGTCAAGAG TTTGCTCAAG GTTGGCATTT TAGCAGTCAA TTATCGGGTC   6300
AGTTTACTCT ACAAGATATA AGTAGCATAG ATTTATTCTC TGTAACAGGT ACTTATGGCG   6360
TCAGAGGCTT TAAATACGGC GGTGCAAGTG GTGAGCGCGG TCTTGTATGG CGTAATGAAT   6420
TAAGTATGCC AAAATACACC CGCTTTCAAA TCAGCCCTTA TGCGTTTTAT GATGCAGGTC   6480
AGTTCCGTTA TAATAGCGAA AATGCTAAAA CTTACGGCGA AGATATGCAC ACGGTATCCT   6540
CTGCGGGTTT AGGCATTAAA ACCTCTCCTA CACAAAACTT AAGCTTAGAT GCTTTTGTTG   6600
CTCGTCGCTT TGCAAATGCC AATAGTGACA ATTTGAATGG CAACAAAAAA CGCACAAGCT   6660
CACCTACAAC CTTCTGGGGT AGATTAACAT TCAGTTTCTA ACCCTGAAAT TTAATCAACT   6720
GGTAAGCGTT CCGCCTACCA GTTTATAACT ATATGCTTTA CCCGCCAATT TACAGTCTAT   6780
ACGCAACCCT GTTTTCATCC TTATATATCA AACAAACTAA GCAAACCAAG CAAACCAAGC   6840
AAACCAAGCA AACCAAGCAA ACCAAGCAAA CCAAGCAAAC CAAGCAAACC AAGCAAACCA   6900
AGCAAACCAA GCAAACCAAG CAAACCAAGC AAACCAAGCA ATGCTAAAAA ACAATTTATA   6960
TGATAAACTA AAACATACTC CATACCATGG CAATACAAGG GATTTAATAA TATGACAAAA   7020
GAAAATTTAC AAAGTGTTCC ACAAAATACG ACCGCTTCAC TTGTAGAATC AAACAACGAC   7080
CAAACTTCCC TGCAAATACT TAAACAACCA CCCAAACCCA ACCTATTACG CCTGGAACAA   7140
CATGTCGCCA AAAAAGATTA TGAGCTTGCT TGCCGCGAAT TAATGGCGAT TTTGGAAAAA   7200
ATGGACGCTA ATTTTGGAGG CGTTCACGAT ATTGAATTTG ACGCACCTGC TCAGCTGGCA   7260
TATCTACCCG AAAAACTACT AATTCATTTT GCCACTCGTC TCGCTAATGC AATTACAACA   7320
CTCTTTTCCG ACCCCGAATT GGCAATTTCC GAAGAAGGGG CATTAAAGAT GATTAGCCTG   7380
CAACGCTGGT TGACGCTGAT TTTTGCCTCT TCCCCCTACG TTAACGCAGA CCATATTCTC   7440
AATAAATATA ATATCAACCC AGATTCCGAA GGTGGCTTTC ATTTAGCAAC AGACAACTCT   7500
TCTATTGCTA AATTCTGTAT TTTTTACTTA CCCGAATCCA ATGTCAATAT GAGTTTAGAT   7560
GCGTTATGGG CAGGGAATCA ACAACTTTGT GCTTCATTGT GTTTTGCGTT GCAGTCTTCA   7620
CGTTTTATTG GTACTGCATC TGCGTTTCAT AAAAGAGCGG TGGTTTTACA GTGGTTTCCT   7680
```

```
AAAAAACTCG CCGAAATTGC TAATTTAGAT GAATTGCCTG CAAATATCCT TCATGATGTA 7740
TATATGCACT GCAGTTATGA TTTAGCAAAA AACAAGCACG ATGTTAAGCG TCCATTAAAC 7800
GAACTTGTCC GCAAGCATAT CCTCACGCAA GGATGGCAAG ACCGCTACCT TTACACCTTA 7860
GGTAAAAAGG ACGGCAAACC TGTGATGATG GTACTGCTTG AACATTTTAA TTCGGGACAT 7920
TCGATTTATC GCACGCATTC AACTTCAATG ATTGCTGCTC GAGAAAAATT CTATTTAGTC 7980
GGCTTAGGCC ATGAGGGCGT TGATAACATA GGTCGAGAAG TGTTTGACGA GTTCTTTGAA 8040
ATCAGTAGCA ATAATATAAT GGAGAGACTG TTTTTTATCC GTAAACAGTG CGAAACTTTC 8100
CAACCCGCAG TGTTCTATAT GCCAAGCATT GGCATGGATA TTACCACGAT TTTTGTGAGC 8160
AACACTCGGC TTGCCCCTAT TCAAGCTGTA GCCTTGGGTC ATCCTGCCAC TACGCATTCT 8220
GAATTTATTG ATTATGTCAT CGTAGAAGAT GATTATGTGG GCAGTGAAGA TTGTTTTAGC 8280
GAAACCCTTT TACGCTTACC CAAAGATGCC CTACCTTATG TACCATCTGC ACTCGCCCCA 8340
CAAAAAGTGG ATTATGTACT CAGGGAAAAC CCTGAAGTAG TCAATATCGG TATTGCCGCT 8400
ACCACAATGA AATTAAACCC TGAATTTTTG CTAACATTGC AAGAAATCAG AGATAAAGCT 8460
AAAGTCAAAA TACATTTTCA TTTCGCACTT GGACAATCAA CAGGCTTGAC ACACCCTTAT 8520
GTCAAATGGT TTATCGAAAG CTATTTAGGT GACGATGCCA CTGCACATCC CCACGCACCT 8580
TATCACGATT ATCTGGCAAT ATTGCGTGAT TGCGATATGC TACTAAATCC GTTTCCTTTC 8640
GGTAATACTA ACGGCATAAT TGATATGGTT ACATTAGGTT TAGTTGGTGT ATGCAAAACG 8700
GGGGATGAAG TACATGAACA TATTGATGAA GGTCTGTTTA AACGCTTAGG ACTACCAGAA 8760
TGGCTGATAG CCGACACACG AGAAACATAT ATTGAATGTG CTTTGCGTCT AGCAGAAAAC 8820
CATCAAGAAC GCCTTGAACT CCGTCGTTAC ATCATAGAAA ACAACGGCTT ACAAAAGCTT 8880
TTTACAGGCG ACCCTCGTCC ATTGGGCAAA ATACTGCTTA AGAAAACAAA TGAATGGAAG 8940
CGGAAGCACT TGAGTAAAAA ATAACGGTTT TTTAAAGTAA AAGTGCGGTT AATTTTCAAA 9000
GCGTTTTAAA AACCTCTCAA AAATCAACCG CACTTTTATC TTTATAACGC TCCCGCGCGC 9060
TGACAGTTTA TCTCTTTCTT AAAATACCCA TAAAATTGTG GCAATAGTTG GGTAATCAAA 9120
TTCAATTGTT GATACGGCAA ACTAAAGACG GCGCGTTCTT CGGCAGTCAT C 9171
```

( 2 ) INFORMATION FOR SEQ ID NO:6:

( i ) SEQUENCE CHARACTERISTICS:
( A ) LENGTH: 9323 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:6:

```
CGCCACTTCA ATTTTGGATT GTTGAAATTC AACTAACCAA AAAGTGCGGT TAAAATCTGT 60
GGAGAAAATA GGTTGTAGTG AAGAACGAGG TAATTGTTCA AAAGGATAAA GCTCTCTTAA 120
TTGGGCATTG GTTGGCGTTT CTTTTTCGGT TAATAGTAAA TTATATTCTG GACGACTATG 180
CAATCCACCA ACAACTTTAC CGTTGGTTTT AAGCGTTAAT GTAAGTTCTT GCTCTTCTTG 240
GCGAATACGT AATCCCATTT TTTGTTTAGC AAGAAAATGA TCGGGATAAT CATAATAGGT 300
GTTGCCCAAA AATAAATTTT GATGTTCTAA AATCATAAAT TTTGCAAGAT ATTGTGGCAA 360
TTCAATACCT ATTTGTGGCG AAATCGCCAA TTTTAATTCA ATTTCTTGTA GCATAATATT 420
TCCCACTCAA ATCAACTGGT TAAATATACA AGATAATAAA AATAAATCAA GATTTTTGTG 480
ATGACAAACA ACAATTACAA CACCTTTTTT GCAGTCTATA TGCAAATATT TTAAAAAAAT 540
```

-continued

```
AGTATAAATC CGCCATATAA AATGGTATAA TCTTTCATCT TTCATCTTTC ATCTTTCATC   600
TTTCATCTTT CATCTTTCAT CTTTCATCTT TCATCTTTCA TCTTTCATCT TTCATCTTTC   660
ATCTTTCATC TTTCATCTTT CACATGAAAT GATGAACCGA GGGAAGGGAG GGAGGGGCAA   720
GAATGAAGAG GGAGCTGAAC GAACGCAAAT GATAAAGTAA TTTAATTGTT CAACTAACCT   780
TAGGAGAAAA TATGAACAAG ATATATCGTC TCAAATTCAG CAAACGCCTG AATGCTTTGG   840
TTGCTGTGTC TGAATTGGCA CGGGGTTGTG ACCATTCCAC AGAAAAAGGC AGCGAAAAAC   900
CTGCTCGCAT GAAAGTGCGT CACTTAGCGT TAAAGCCACT TTCCGCTATG TTACTATCTT   960
TAGGTGTAAC ATCTATTCCA CAATCTGTTT TAGCAAGCGG CAATTTAACA TCGACCAAAA  1020
TGAAATGGTG CAGTTTTTAC AAGAAAACAA GTAATAAAAC CATTATCCGC AACAGTGTTG  1080
ACGCTATCAT TAATTGGAAA CAATTTAACA TCGACCAAAA TGAAATGGTG CAGTTTTTAC  1140
AAGAAAACAA CAACTCCGCC GTATTCAACC GTGTTACATC TAACCAAATC TCCCAATTAA  1200
AAGGGATTTT AGATTCTAAC GGACAAGTCT TTTTAATCAA CCCAAATGGT ATCACAATAG  1260
GTAAAGACGC AATTATTAAC ACTAATGGCT TTACGGCTTC TACGCTAGAC ATTTCTAACG  1320
AAAACATCAA GGCGCGTAAT TTCACCTTCG AGCAAACCAA AGATAAAGCG CTCGCTGAAA  1380
TTGTGAATCA CGGTTTAATT ACTGTCGGTA AAGACGGCAG TGTAAATCTT ATTGGTGGCA  1440
AAGTGAAAAA CGAGGGTGTG ATTAGCGTAA ATGGTGGCAG CATTTCTTTA CTCGCAGGGC  1500
AAAAAATCAC CATCAGCGAT ATAATAAACC CAACCATTAC TTACAGCATT GCCGCGCCTG  1560
AAAATGAAGC GGTCAATCTG GGCGATATTT TTGCCAAAGG CGGTAACATT AATGTCCGTG  1620
CTGCCACTAT TCGAAACCAA GGTAAACTTT CTGCTGATTC TGTAAGCAAA GATAAAAGCG  1680
GCAATATTGT TCTTTCCGCC AAAGAGGGTG AAGCGGAAAT TGGCGGTGTA ATTTCCGCTC  1740
AAAATCAGCA AGCTAAAGGC GGCAAGCTGA TGATAAAGTC CGATAAAGTC ACATTAAAAA  1800
CAGGTGCAGT TATCGACCTT TCAGGTAAAG AAGGGGGAGA AACTTACCTT GGCGGTGACG  1860
AGCGCGGCGA AGGTAAAAAC GGCATTCAAT TAGCAAAGAA AACCTCTTTA GAAAAAGGCT  1920
CAACCATCAA TGTATCAGGC AAAGAAAAAG GCGGACGCGC TATTGTGTGG GGCGATATTG  1980
CGTTAATTGA CGGCAATATT AACGCTCAAG GTAGTGGTGA TATCGCTAAA ACCGGTGGTT  2040
TTGTGGAGAC ATCGGGGCAT TATTTATCCA TTGACAGCAA TGCAATTGTT AAAACAAAAG  2100
AGTGGTTGCT AGACCCTGAT GATGTAACAA TTGAAGCCGA AGACCCCCTT CGCAATAATA  2160
CCGGTATAAA TGATGAATTC CCAACAGGCA CCGGTGAAGC AAGCGACCCT AAAAAAAATA  2220
GCGAACTCAA AACAACGCTA ACCAATACAA CTATTTCAAA TTATCTGAAA AACGCCTGGA  2280
CAATGAATAT AACGGCATCA AGAAAACTTA CCGTTAATAG CTCAATCAAC ATCGGAAGCA  2340
ACTCCCACTT AATTCTCCAT AGTAAAGGTC AGCGTGGCGG AGGCGTTCAG ATTGATGGAG  2400
ATATTACTTC TAAAGGCGGA AATTTAACCA TTTATTCTGG CGGATGGGTT GATGTTCATA  2460
AAAATATTAC GCTTGATCAG GGTTTTTTAA ATATTACCGC CGCTTCCGTA GCTTTTGAAG  2520
GTGGAAATAA CAAAGCACGC GACGCGGCAA ATGCTAAAAT TGTCGCCCAG GGCACTGTAA  2580
CCATTACAGG AGAGGGAAAA GATTTCAGGG CTAACAACGT ATCTTTAAAC GGAACGGGTA  2640
AAGGTCTGAA TATCATTTCA TCAGTGAATA ATTTAACCCA CAATCTTAGT GGCACAATTA  2700
ACATATCTGG GAATATAACA ATTAACCAAA CTACGAGAAA GAACACCTCG TATTGGCAAA  2760
CCAGCCATGA TTCGCACTGG AACGTCAGTG CTCTTAATCT AGAGACAGGC GCAAATTTTA  2820
CCTTTATTAA ATACATTTCA AGCAATAGCA AAGGCTTAAC AACACAGTAT AGAAGCTCTG  2880
CAGGGGTGAA TTTTAACGGC GTAAATGGCA ACATGTCATT CAATCTCAAA GAAGGAGCGA  2940
```

```
AAGTTAATTT CAAATTAAAA CCAAACGAGA ACATGAACAC AAGCAAACCT TTACCAATTC 3000
GGTTTTTAGC CAATATCACA GCCACTGGTG GGGGCTCTGT TTTTTTTGAT ATATATGCCA 3060
ACCATTCTGG CAGAGGGGCT GAGTTAAAAA TGAGTGAAAT TAATATCTCT AACGGCGCTA 3120
ATTTTACCTT AAATTCCCAT GTTCGCGGCG ATGACGCTTT TAAAATCAAC AAAGACTTAA 3180
CCATAAATGC AACCAATTCA AATTTCAGCC TCAGACAGAC GAAAGATGAT TTTTATGACG 3240
GGTACGCACG CAATGCCATC AATTCAACCT ACAACATATC CATTCTGGGC GGTAATGTCA 3300
CCCTTGGTGG ACAAAACTCA AGCAGCAGCA TTACGGGGAA TATTACTATC GAGAAAGCAG 3360
CAAATGTTAC GCTAGAAGCC AATAACGCCC CTAATCAGCA AAACATAAGG GATAGAGTTA 3420
TAAAACTTGG CAGCTTGCTC GTTAATGGGA GTTTAAGTTT AACTGGCGAA AATGCAGATA 3480
TTAAAGGCAA TCTCACTATT TCAGAAAGCG CCACTTTTAA AGGAAAGACT AGAGATACCC 3540
TAAATATCAC CGGCAATTTT ACCAATAATG GCACTGCCGA AATTAATATA ACACAAGGAG 3600
TGGTAAAACT TGGCAATGTT ACCAATGATG GTGATTTAAA CATTACCACT CACGCTAAAC 3660
GCAACCAAAG AAGCATCATC GGCGGAGATA TAATCAACAA AAAAGGAAGC TTAAATATTA 3720
CAGACAGTAA TAATGATGCT GAAATCCAAA TTGGCGGCAA TATCTCGCAA AAAGAAGGCA 3780
ACCTCACGAT TTCTTCCGAT AAAATTAATA TCACCAAACA GATAACAATC AAAAAGGGTA 3840
TTGATGGAGA GGACTCTAGT TCAGATGCGA CAAGTAATGC CAACCTAACT ATTAAAACCA 3900
AAGAATTGAA ATTGACAGAA GACCTAAGTA TTTCAGGTTT CAATAAAGCA GAGATTACAG 3960
CCAAAGATGG TAGAGATTTA ACTATTGGCA ACAGTAATGA CGGTAACAGC GGTGCCGAAG 4020
CCAAAACAGT AACTTTTAAC AATGTTAAAG ATTCAAAAAT CTCTGCTGAC GGTCACAATG 4080
TGACACTAAA TAGCAAAGTG AAAACATCTA GCAGCAATGG CGGACGTGAA AGCAATAGCG 4140
ACAACGATAC CGGCTTAACT ATTACTGCAA AAAATGTAGA AGTAAACAAA GATATTACTT 4200
CTCTCAAAAC AGTAAATATC ACCGCGTCGG AAAAGGTTAC CACCACAGCA GGCTCGACCA 4260
TTAACGCAAC AAATGGCAAA GCAAGTATTA CAACCAAAAC AGGTGATATC AGCGGTACGA 4320
TTTCCGGTAA CACGGTAAGT GTTAGCGCGA CTGGTGATTT AACCACTAAA TCCGGCTCAA 4380
AAATTGAAGC GAAATCGGGT GAGGCTAATG TAACAAGTGC AACAGGTACA ATTGGCGGTA 4440
CAATTTCCGG TAATACGGTA AATGTTACGG CAAACGCTGG CGATTTAACA GTTGGGAATG 4500
GCGCAGAAAT TAATGCGACA GAAGGAGCTG CAACCTTAAC CGCAACAGGG AATACCTTGA 4560
CTACTGAAGC CGGTTCTAGC ATCACTTCAA CTAAGGGTCA GGTAGACCTC TTGGCTCAGA 4620
ATGGTAGCAT CGCAGGAAGC ATTAATGCTG CTAATGTGAC ATTAAATACT ACAGGCACCT 4680
TAACCACCGT GGCAGGCTCG GATATTAAAG CAACCAGCGG CACCTTGGTT ATTAACGCAA 4740
AAGATGCTAA GCTAAATGGT GATGCATCAG GTGATAGTAC AGAAGTGAAT GCAGTCAACG 4800
ACTGGGGATT TGGTAGTGTG ACTGCGGCAA CCTCAAGCAG TGTGAATATC ACTGGGGATT 4860
TAAACACAGT AAATGGGTTA AATATCATTT CGAAAGATGG TAGAAACACT GTGCGCTTAA 4920
GAGGCAAGGA AATTGAGGTG AAATATATCC AGCCAGGTGT AGCAAGTGTA GAAGAAGTAA 4980
TTGAAGCGAA ACGCGTCCTT GAAAAAGTAA AAGATTTATC TGATGAAGAA AGAGAAACAT 5040
TAGCTAAACT TGGTGTAAGT GCTGTACGTT TTGTTGAGCC AAATAATACA ATTACAGTCA 5100
ATACACAAAA TGAATTTACA ACCAGACCGT CAAGTCAAGT GATAATTTCT GAAGGTAAGG 5160
CGTGTTTCTC AAGTGGTAAT GGCGCACGAG TATGTACCAA TGTTGCTGAC GATGGACAGC 5220
CGTAGTCAGT AATTGACAAG GTAGATTTCA TCCTGCAATG AAGTCATTTT ATTTTCGTAT 5280
TATTTACTGT GTGGGTTAAA GTTCAGTACG GGCTTTACCC ATCTTGTAAA AAATTACGGA 5340
```

-continued

GAATACAATA AAGTATTTTT AACAGGTTAT TATTATGAAA AATATAAAAA GCAGATTAAA 5400
ACTCAGTGCA ATATCAGTAT TGCTTGGCCT GGCTTCTTCA TCATTGTATG CAGAAGAAGC 5460
GTTTTTAGTA AAAGGCTTTC AGTTATCTGG TGCACTTGAA ACTTTAAGTG AAGACGCCCA 5520
ACTGTCTGTA GCAAAATCTT TATCTAAATA CCAAGGCTCG CAAACTTTAA CAAACCTAAA 5580
AACAGCACAG CTTGAATTAC AGGCTGTGCT AGATAAGATT GAGCCAAATA AATTTGATGT 5640
GATATTGCCG CAACAAACCA TTACGGATGG CAATATCATG TTTGAGCTAG TCTCGAAATC 5700
AGCCGCAGAA AGCCAAGTTT TTTATAAGGC GAGCCAGGGT TATAGTGAAG AAAATATCGC 5760
TCGTAGCCTG CCATCTTTGA AACAAGGAAA AGTGTATGAA GATGGTCGTC AGTGGTTCGA 5820
TTTGCGTGAA TTTAATATGG CAAAAGAAAA CCCGCTTAAG GTTACCCGTG TACATTACGA 5880
ACTAAACCCT AAAAACAAAA CCTCTAATTT GATAATTGCG GGCTTCTCGC CTTTTGGTAA 5940
AACGCGTAGC TTTATTTCTT ATGATAATTT CGGCGCGAGA GAGTTTAACT ACCAACGTGT 6000
AAGCTTGGGT TTTGTTAATG CCAATTTAAC TGGTCATGAT GATGTGTTAA TTATACCAGT 6060
ATGAGTTATG CTGATTCTAA TGATATCGAC GGCTTACCAA GTGCGATTAA TCGTAAATTA 6120
TCAAAAGGTC AATCTATCTC TGCGAATCTG AAATGGAGTT ATTATCTCCC AACATTTAAC 6180
CTTGGCATGG AAGACCAATT TAAAATTAAT TTAGGCTACA ACTACCGCCA TATTAATCAA 6240
ACCTCCGCGT TAAATCGCTT GGGTGAAACG AAGAAAAAAT TTGCAGTATC AGGCGTAAGT 6300
GCAGGCATTG ATGGACATAT CCAATTTACC CCTAAAACAA TCTTTAATAT TGATTTAACT 6360
CATCATTATT ACGCGAGTAA ATTACCAGGC TCTTTTGGAA TGGAGCGCAT TGGCGAAACA 6420
TTTAATCGCA GCTATCACAT TAGCACAGCC AGTTTAGGGT TGAGTCAAGA GTTTGCTCAA 6480
GGTTGGCATT TTAGCAGTCA ATTATCAGGT CAATTTACTC TACAAGATAT TAGCAGTATA 6540
GATTTATTCT CTGTAACAGG TACTTATGGC GTCAGAGGCT TTAAATACGG CGGTGCAAGT 6600
GGTGAGCGCG GTCTTGTATG GCGTAATGAA TTAAGTATGC CAAAATACAC CCGCTTCCAA 6660
ATCAGCCCTT ATGCGTTTTA TGATGCAGGT CAGTTCCGTT ATAATAGCGA AAATGCTAAA 6720
ACTTACGGCG AAGATATGCA CACGGTATCC TCTGCGGGTT TAGGCATTAA AACCTCTCCT 6780
ACACAAAACT TAAGCCTAGA TGCTTTTGTT GCTCGTCGCT TTGCAAATGC CAATAGTGAC 6840
AATTTGAATG GCAACAAAAA ACGCACAAGC TCACCTACAA CCTTCTGGGG GAGATTAACA 6900
TTCAGTTTCT AACCCTGAAA TTTAATCAAC TGGTAAGCGT TCCGCCTACC AGTTTATAAC 6960
TATATGCTTT ACCCGCCAAT TTACAGTCTA TAGGCAACCC TGTTTTTACC CTTATATATC 7020
AAATAAACAA GCTAAGCTGA GCTAAGCAAA CCAAGCAAAC TCAAGCAAGC CAAGTAATAC 7080
TAAAAAAACA ATTTATATGA TAAACTAAAG TATACTCCAT GCCATGGCGA TACAAGGGAT 7140
TTAATAATAT GACAAAAGAA AATTTGCAAA ACGCTCCTCA AGATGCGACC GCTTTACTTG 7200
CGGAATTAAG CAACAATCAA ACTCCCCTGC GAATATTTAA ACAACCACGC AAGCCCAGCC 7260
TATTACGCTT GGAACAACAT ATCGCAAAAA AAGATTATGA GTTTGCTTGT CGTGAATTAA 7320
TGGTGATTCT GGAAAAAATG GACGCTAATT TTGGAGGCGT TCACGATATT GAATTTGACG 7380
CACCCGCTCA GCTGGCATAT CTACCCGAAA AATTACTAAT TTATTTTGCC ACTCGTCTCG 7440
CTAATGCAAT TACAACACTC TTTTCCGACC CCGAATTGGC AATTTCTGAA GAAGGGGCGT 7500
TAAAGATGAT TAGCCTGCAA CGCTGGTTGA CGCTGATTTT TGCCTCTTCC CCCTACGTTA 7560
ACGCAGACCA TATTCTCAAT AAATATAATA TCAACCCAGA TTCCGAAGGT GGCTTTCATT 7620
TAGCAACAGA CAACTCTTCT ATTGCTAAAT TCTGTATTTT TTACTTACCC GAATCCAATG 7680
TCAATATGAG TTTAGATGCG TTATGGGCAG GGAATCAACA ACTTTGTGCT TCATTGTGTT 7740

-continued

```
TTGCGTTGCA GTCTTCACGT TTTATTGGTA CCGCATCTGC GTTTCATAAA AGAGCGGTGG 7800
TTTTACAGTG GTTTCCTAAA AAACTCGCCG AAATTGCTAA TTTAGATGAA TTGCCTGCAA 7860
ATATCCTTCA TGATGTATAT ATGCACTGCA GTTATGATTT AGCAAAAAAC AAGCACGATG 7920
TTAAGCGTCC ATTAAACGAA CTTGTCCGCA AGCATATCCT CACGCAAGGA TGGCAAGACC 7980
GCTACCTTTA CACCTTAGGT AAAAAGGACG GCAAACCTGT GATGATGGTA CTGCTTGAAC 8040
ATTTTAATTC GGGACATTCG ATTTATCGTA CACATTCAAC TTCAATGATT GCTGCTCGAG 8100
AAAAATTCTA TTTAGTCGGC TTAGGCCATG AGGGCGTTGA TAAAATAGGT CGAGAAGTGT 8160
TTGACGAGTT CTTTGAAATC AGTAGCAATA ATATAATGGA GAGACTGTTT TTTATCCGTA 8220
AACAGTGCGA AACTTTCCAA CCCGCAGTGT TCTATATGCC AAGCATTGGC ATGGATATTA 8280
CCACGATTTT TGTGAGCAAC ACTCGGCTTG CCCCTATTCA AGCTGTAGCC CTGGGTCATC 8340
CTGCCACTAC GCATTCTGAA TTTATTGATT ATGTCATCGT AGAAGATGAT TATGTGGGCA 8400
GTGAAGATTG TTTCAGCGAA ACCCTTTTAC GCTTACCCAA AGATGCCCTA CCTTATGTAC 8460
CTTCTGCACT CGCCCCACAA AAAGTGGATT ATGTACTCAG GGAAAACCCT GAAGTAGTCA 8520
ATATCGGTAT TGCCGCTACC ACAATGAAAT TAAACCCTGA ATTTTTGCTA ACATTGCAAG 8580
AAATCAGAGA TAAAGCTAAA GTCAAAATAC ATTTTCATTT CGCACTTGGA CAATCAACAG 8640
GCTTGACACA CCCTTATGTC AAATGGTTTA TCGAAAGCTA TTTAGGTGAC GATGCCACTG 8700
CACATCCCCA CGCACCTTAT CACGATTATC TGGCAATATT GCGTGATTGC GATATGCTAC 8760
TAAATCCGTT TCCTTTCGGT AATACTAACG GCATAATTGA TATGGTTACA TTAGGTTTAG 8820
TTGGTGTATG CAAAACGGGG GATGAAGTAC ATGAACATAT TGATGAAGGT CTGTTTAAAC 8880
GCTTAGGACT ACCAGAATGG CTGATAGCCG ACACACGAGA AACATATATT GAATGTGCTT 8940
TGCGTCTAGC AGAAAACCAT CAAGAACGCC TTGAACTCCG TCGTTACATC ATAGAAAACA 9000
ACGGCTTACA AAAGCTTTTT ACAGGCGACC CTCGTCCATT GGGCAAAATA CTGCTTAAGA 9060
AAACAAATGA ATGGAAGCGG AAGCACTTGA GTAAAAAATA ACGGTTTTTT AAAGTAAAAG 9120
TGCGGTTAAT TTTCAAAGCG TTTTAAAAAC CTCTCAAAAA TCAACCGCAC TTTTATCTTT 9180
ATAACGATCC CGCACGCTGA CAGTTTATCA GCCTCCCGCC ATAAAACTCC GCCTTTCATG 9240
GCGGAGATTT TAGCCAAAAC TGGCAGAAAT TAAAGGCTAA AATCACCAAA TTGCACCACA 9300
AAATCACCAA TACCCACAAA AAA                                         9323
```

( 2 ) INFORMATION FOR SEQ ID NO:7:

( i ) SEQUENCE CHARACTERISTICS:
( A ) LENGTH: 4287 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:7:

```
GATCAATCTG GGCGATATTT TTGCCAAAGG TGGTAACATT AATGTCCGCG CTGCCACTAT 60
TCGCAATAAA GGTAAACTTT CTGCCGACTC TGTAAGCAAA GATAAAAGTG GTAACATTGT 120
TCTCTCTGCC AAAGAAGGTG AAGCGGAAAT TGGCGGTGTA ATTTCCGCTC AAAATCAGCA 180
AGCCAAAGGT GGTAAGTTGA TGATTACAGG CGATAAAGTT ACATTGAAAA CGGGTGCACT 240
TATCGACCTT TCGGGTAAAG AAGGGGGAGA AACTTATCTT GGCGGTGACG AGCGTGGCGA 300
AGGTAAAAAC GGCATTCAAT TAGCAAAGAA AACCACTTTA GAAAAAGGCT CAACAATTAA 360
```

-continued

| | | | | | | |
|---|---|---|---|---|---|---|
| TGTGTCAGGT | AAAGAAAAAG | CTGGGCGCGC | TATTGTATGG | GGCGATATTG | CGTTAATTGA | 420 |
| CGGCAATATT | AATGCCCAAG | GTAAAGATAT | CGCTAAAACT | GGTGGTTTTG | TGGAGACGTC | 480 |
| GGGGCATTAC | TTATCCATTG | ATGATAACGC | AATTGTTAAA | ACAAAAGAAT | GGCTACTAGA | 540 |
| CCCAGAGAAT | GTGACTATTG | AAGCTCCTTC | CGCTTCTCGC | GTCGAGCTGG | GTGCCGATAG | 600 |
| GAATTCCCAC | TCGGCAGAGG | TGATAAAAGT | GACCCTAAAA | AAAAATAACA | CCTCCTTGAC | 660 |
| AACACTAACC | AATACAACCA | TTTCAAATCT | TCTGAAAAGT | GCCCACGTGG | TGAACATAAC | 720 |
| GGCAAGGAGA | AAACTTACCG | TTAATAGCTC | TATCAGTATA | GAAAGAGGCT | CCCACTTAAT | 780 |
| TCTCCACAGT | GAAGGTCAGG | GCGGTCAAGG | TGTTCAGATT | GATAAAGATA | TTACTTCTGA | 840 |
| AGGCGGAAAT | TTAACCATTT | ATTCTGGCGG | ATGGGTTGAT | GTTCATAAAA | ATATTACGCT | 900 |
| TGGTAGCGGC | TTTTTAAACA | TCACAACTAA | AGAAGGAGAT | ATCGCCTTCG | AAGACAAGTC | 960 |
| TGGACGGAAC | AACCTAACCA | TTACAGCCCA | AGGGACCATC | ACCTCAGGTA | ATAGTAACGG | 1020 |
| CTTTAGATTT | AACAACGTCT | CTCTAAACAG | CCTTGGCGGA | AAGCTGAGCT | TTACTGACAG | 1080 |
| CAGAGAGGAC | AGAGGTAGAA | GAACTAAGGG | TAATATCTCA | AACAAATTTG | ACGGAACGTT | 1140 |
| AAACATTTCC | GGAACTGTAG | ATATCTCAAT | GAAAGCACCC | AAAGTCAGCT | GGTTTTACAG | 1200 |
| AGACAAAGGA | CGCACCTACT | GGAACGTAAC | CACTTTAAAT | GTTACCTCGG | GTAGTAAATT | 1260 |
| TAACCTCTCC | ATTGACAGCA | CAGGAAGTGG | CTCAACAGGT | CCAAGCATAC | GCAATGCAGA | 1320 |
| ATTAAATGGC | ATAACATTTA | ATAAAGCCAC | TTTTAATATC | GCACAAGGCT | CAACAGCTAA | 1380 |
| CTTTAGCATC | AAGGCATCAA | TAATGCCCTT | TAAGAGTAAC | GCTAACTACG | CATTATTTAA | 1440 |
| TGAAGATATT | TCAGTCTCAG | GGGGGGGTAG | CGTTAATTTC | AAACTTAACG | CCTCATCTAG | 1500 |
| CAACATACAA | ACCCCTGGCG | TAATTATAAA | ATCTCAAAAC | TTTAATGTCT | CAGGAGGGTC | 1560 |
| AACTTTAAAT | CTCAAGGCTG | AAGGTTCAAC | AGAAACCGCT | TTTTCAATAG | AAAATGATTT | 1620 |
| AAACTTAAAC | GCCACCGGTG | GCAATATAAC | AATCAGACAA | GTCGAGGGTA | CCGATTCACG | 1680 |
| CGTCAACAAA | GGTGTCGCAG | CCAAAAAAAA | CATAACTTTT | AAAGGGGGTA | ATATCACCTT | 1740 |
| CGGCTCTCAA | AAAGCCACAA | CAGAAATCAA | AGGCAATGTT | ACCATCAATA | AAAACACTAA | 1800 |
| CGCTACTCTT | CGTGGTGCGA | ATTTTGCCGA | AAACAAATCG | CCTTTAAATA | TAGCAGGAAA | 1860 |
| TGTTATTAAT | AATGGCAACC | TTACCACTGC | CGGCTCCATT | ATCAATATAG | CCGGAAATCT | 1920 |
| TACTGTTTCA | AAAGGCGCTA | ACCTTCAAGC | TATAACAAAT | TACACTTTTA | ATGTAGCCGG | 1980 |
| CTCATTTGAC | AACAATGGCG | CTTCAAACAT | TTCCATTGCC | AGAGGAGGGG | CTAAATTTAA | 2040 |
| AGATATCAAT | AACACCAGTA | GCTTAAATAT | TACCACCAAC | TCTGATACCA | CTTACCGCAC | 2100 |
| CATTATAAAA | GGCAATATAT | CCAACAAATC | AGGTGATTTG | AATATTATTG | ATAAAAAAAG | 2160 |
| CGACGCTGAA | ATCCAAATTG | GCGGCAATAT | CTCACAAAAA | GAAGGCAATC | TCACAATTTC | 2220 |
| TTCTGATAAA | GTAAATATTA | CCAATCAGAT | AACAATCAAA | GCAGGCGTTG | AAGGGGGGCG | 2280 |
| TTCTGATTCA | AGTGAGGCAG | AAAATGCTAA | CCTAACTATT | CAAACCAAAG | AGTTAAAATT | 2340 |
| GGCAGGAGAC | CTAAATATTT | CAGGCTTTAA | TAAAGCAGAA | ATTACAGCTA | AAAATGGCAG | 2400 |
| TGATTTAACT | ATTGGCAATG | CTAGCGGTGG | TAATGCTGAT | GCTAAAAAAG | TGACTTTTGA | 2460 |
| CAAGGTTAAA | GATTCAAAAA | TCTCGACTGA | CGGTCACAAT | GTAACACTAA | ATAGCGAAGT | 2520 |
| GAAAACGTCT | AATGGTAGTA | GCAATGCTGG | TAATGATAAC | AGCACCGGTT | TAACCATTTC | 2580 |
| CGCAAAAGAT | GTAACGGTAA | ACAATAACGT | TACCTCCCAC | AAGACAATAA | ATATCTCTGC | 2640 |
| CGCAGCAGGA | AATGTAACAA | CCAAAGAAGG | CACAACTATC | AATGCAACCA | CAGGCAGCGT | 2700 |
| GGAAGTAACT | GCTCAAAATG | GTACAATTAA | AGGCAACATT | ACCTCGCAAA | ATGTAACAGT | 2760 |

-continued

| | | | | | | |
|---|---|---|---|---|---|---|
| GACAGCAACA | GAAAATCTTG | TTACCACAGA | GAATGCTGTC | ATTAATGCAA | CCAGCGGCAC | 2820 |
| AGTAAACATT | AGTACAAAAA | CAGGGGATAT | TAAAGGTGGA | ATTGAATCAA | CTTCCGGTAA | 2880 |
| TGTAAATATT | ACAGCGAGCG | GCAATACACT | TAAGGTAAGT | AATATCACTG | GTCAAGATGT | 2940 |
| AACAGTAACA | GCGGATGCAG | GAGCCTTGAC | AACTACAGCA | GGCTCAACCA | TTAGTGCGAC | 3000 |
| AACAGGCAAT | GCAAATATTA | CAACCAAAAC | AGGTGATATC | AACGGTAAAG | TTGAATCCAG | 3060 |
| CTCCGGCTCT | GTAACACTTG | TTGCAACTGG | AGCAACTCTT | GCTGTAGGTA | ATATTTCAGG | 3120 |
| TAACACTGTT | ACTATTACTG | CGGATAGCGG | TAAATTAACC | TCCACAGTAG | GTTCTACAAT | 3180 |
| TAATGGGACT | AATAGTGTAA | CCACCTCAAG | CCAATCAGGC | GATATTGAAG | GTACAATTTC | 3240 |
| TGGTAATACA | GTAAATGTTA | CAGCAAGCAC | TGGTGATTTA | ACTATTGGAA | ATAGTGCAAA | 3300 |
| AGTTGAAGCG | AAAAATGGAG | CTGCAACCTT | AACTGCTGAA | TCAGGCAAAT | TAACCACCCA | 3360 |
| AACAGGCTCT | AGCATTACCT | CAAGCAATGG | TCAGACAACT | CTTACAGCCA | AGGATAGCAG | 3420 |
| TATCGCAGGA | AACATTAATG | CTGCTAATGT | GACGTTAAAT | ACCACAGGCA | CTTTAACTAC | 3480 |
| TACAGGGGAT | TCAAAGATTA | ACGCAACCAG | TGGTACCTTA | ACAATCAATG | CAAAAGATGC | 3540 |
| CAAATTAGAT | GGTGCTGCAT | CAGGTGACCG | CACAGTAGTA | AATGCAACTA | ACGCAAGTGG | 3600 |
| CTCTGGTAAC | GTGACTGCGA | AAACCTCAAG | CAGCGTGAAT | ATCACCGGGG | ATTTAAACAC | 3660 |
| AATAAATGGG | TTAAATATCA | TTTCGGAAAA | TGGTAGAAAC | ACTGTGCGCT | TAAGAGGCAA | 3720 |
| GGAAATTGAT | GTGAAATATA | TCCAACCAGG | TGTAGCAAGC | GTAGAAGAGG | TAATTGAAGC | 3780 |
| GAAACGCGTC | CTTGAGAAGG | TAAAAGATTT | ATCTGATGAA | GAAAGAGAAA | CACTAGCCAA | 3840 |
| ACTTGGTGTA | AGTGCTGTAC | GTTTCGTTGA | GCCAAATAAT | GCCATTACGG | TTAATACACA | 3900 |
| AAACGAGTTT | ACAACCAAAC | CATCAAGTCA | AGTGACAATT | TCTGAAGGTA | AGGCGTGTTT | 3960 |
| CTCAAGTGGT | AATGGCGCAC | GAGTATGTAC | CAATGTTGCT | GACGATGGAC | AGCAGTAGTC | 4020 |
| AGTAATTGAC | AAGGTAGATT | TCATCCTGCA | ATGAAGTCAT | TTTATTTTCG | TATTATTTAC | 4080 |
| TGTGTGGGTT | AAAGTTCAGT | ACGGGCTTTA | CCCACCTTGT | AAAAAATTAC | GAAAAATACA | 4140 |
| ATAAAGTATT | TTTAACAGGT | TATTATTATG | AAAAACATAA | AAAGCAGATT | AAAACTCAGT | 4200 |
| GCAATATCAA | TATTGCTTGG | CTTGGCTTCT | TCATCGACGT | ATGCAGAAGA | AGCGTTTTTA | 4260 |
| GTAAAAGGCT | TTCAGTTATC | TGGCGCG | | | | 4287 |

( 2 ) INFORMATION FOR SEQ ID NO:8:

( i ) SEQUENCE CHARACTERISTICS:
( A ) LENGTH: 4702 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:8:

| | | | | | | |
|---|---|---|---|---|---|---|
| GGGAATGAGC | GTCGTACACG | GTACAGCAAC | CATGCAAGTA | GACGGCAATA | AAACCACTAT | 60 |
| CCGTAATAGC | ATCAATGCTA | TCATCAATTG | GAAACAATTT | AACATTGACC | AAAATGAAAT | 120 |
| GGAGCAGTTT | TTACAAGAAA | GCAGCAACTC | TGCCGTTTTC | AACCGTGTTA | CATCTGACCA | 180 |
| AATCTCCCAA | TTAAAAGGGA | TTTTAGATTC | TAACGGACAA | GTCTTTTTAA | TCAACCCAAA | 240 |
| TGGTATCACA | ATAGGTAAAG | ACGCAATTAT | TAACACTAAT | GGCTTTACTG | CTTCTACGCT | 300 |
| AGACATTTCT | AACGAAAACA | TCAAGGCGCG | TAATTTCACC | CTTGAGCAAA | CCAAGGATAA | 360 |
| AGCACTCGCT | GAAATCGTGA | ATCACGGTTT | AATTACCGTT | GGTAAAGACG | GTAGCGTAAA | 420 |
| CCTTATTGGT | GGCAAAGTGA | AAAACGAGGG | CGTGATTAGC | GTAAATGGCG | GTAGTATTTC | 480 |

-continued

```
TTTACTTGCA GGGCAAAAAA TCACCATCAG CGATATAATA AATCCAACCA TCACTTACAG    540
CATTGCTGCA CCTGAAAACG AAGCGATCAA TCTGGGCGAT ATTTTTGCCA AAGGTGGTAA    600
CATTAATGTC CGCGCTGCCA CTATTCGCAA TAAAGGTAAA CTTTCTGCCG ACTCTGTAAG    660
CAAAGATAAA AGTGGTAACA TTGTTCTCTC TGCCAAAGAA GGTGAAGCGG AAATTGGCGG    720
TGTAATTTCC GCTCAAAATC AGCAAGCCAA AGGTGGTAAG TTGATGATTA CAGGTGATAA    780
AGTCACATTA AAAACAGGTG CAGTTATCGA CCTTTCAGGT AAAGAAGGGG GAGAGACTTA    840
TCTTGGCGGT GATGAGCGTG GCGAAGGTAA AAATGGTATT CAATTAGCGA AGAAAACCTC    900
TTTAGAAAAA GGCTCGACAA TTAATGTATC AGGCAAAGAA AAAGGCGGGC GCGCTATTGT    960
ATGGGGCGAT ATTGCATTAA TTAATGGTAA CATTAATGCT CAAGGTAGCG ATATTGCTAA   1020
AACTGGCGGC TTTGTGGAAA CATCAGGACA TGACTTATCC ATTGGTGATG ATGTGATTGT   1080
TGACGCTAAA GAGTGGTTAT TAGACCCAGA TGATGTGTCC ATTGAAACTC TTACATCTGG   1140
ACGCAATAAT ACCGGCGAAA ACCAAGGATA TACAACAGGA GATGGGACTA AAGAGTCACC   1200
TAAAGGTAAT AGTATTTCTA AACCTACATT AACAAACTCA ACTCTTGAGC AAATCCTAAG   1260
AAGAGGTTCT TATGTTAATA TCACTGCTAA TAATAGAATT TATGTTAATA GCTCCATCAA   1320
CTTATCTAAT GGCAGTTTAA CACTTCACAC TAAACGAGAT GGAGTTAAAA TTAACGGTGA   1380
TATTACCTCA AACGAAAATG GTAATTTAAC CATTAAAGCA GGCTCTTGGG TTGATGTTCA   1440
TAAAAACATC ACGCTTGGTA CGGGTTTTTT CAATATTGTC GCTGGGGATT CTGTAGCTTT   1500
TGAGAGAGAG GGCGATAAAG CACGTAACGC AACAGATGCT CAAATTACCG CACAAGGGAC   1560
GATAACCGTC AATAAAGATG ATAAACAATT TAGATTCAAT AATGTATCTA TTAACGGGAC   1620
GGGCAAGGGT TTAAAGTTTA TTGCAAATCA AAATAATTTC ACTCATAAAT TTGATGGCGA   1680
AATTAACATA TCTGGAATAG TAACAATTAA CCAAACCACG AAAAAAGATG TTAAATACTG   1740
GAATGCATCA AAAGACTCTT ACTGGAATGT TTCTTCTCTT ACTTTGAATA CGGTGCAAAA   1800
ATTTACCTTT ATAAAATTCG TTGATAGCGG CTCAAATTCC CAAGATTTGA GGTCATCACG   1860
TAGAAGTTTT GCAGGCGTAC ATTTTAACGG CATCGGAGGC AAAACAAACT TCAACATCGG   1920
AGCTAACGCA AAAGCCTTAT TTAAATTAAA ACCAAACGCC GCTACAGACC CAAAAAAAGA   1980
ATTACCTATT ACTTTTAACG CCAACATTAC AGCTACCGGT AACAGTGATA GCTCTGTGAT   2040
GTTTGACATA CACGCCAATC TTACCTCTAG AGCTGCCGGC ATAAACATGG ATTCAATTAA   2100
CATTACCGGC GGGCTTGACT TTTCCATAAC ATCCCATAAT CGCAATAGTA ATGCTTTTGA   2160
AATCAAAAAA GACTTAACTA TAAATGCAAC TGGCTCGAAT TTTAGTCTTA AGCAAACGAA   2220
AGATTCTTTT TATAATGAAT ACAGCAAACA CGCCATTAAC TCAAGTCATA ATCTAACCAT   2280
TCTTGGCGGC AATGTCACTC TAGGTGGGGA AAATTCAAGC AGTAGCATTA CGGGCAATAT   2340
CAATATCACC AATAAAGCAA ATGTTACATT ACAAGCTGAC ACCAGCAACA GCAACACAGG   2400
CTTGAAGAAA AGAACTCTAA CTCTTGGCAA TATATCTGTT GAGGGGAATT TAAGCCTAAC   2460
TGGTGCAAAT GCAAACATTG TCGGCAATCT TTCTATTGCA GAAGATTCCA CATTTAAAGG   2520
AGAAGCCAGT GACAACCTAA ACATCACCGG CACCTTTACC AACAACGGTA CCGCCAACAT   2580
TAATATAAAA CAAGGAGTGG TAAAACTCCA AGGCGATATT ATCAATAAAG GTGGTTTAAA   2640
TATCACTACT AACGCCTCAG GCACTCAAAA AACCATTATT AACGGAAATA TAACTAACGA   2700
AAAAGGCGAC TTAAACATCA AGAATATTAA AGCCGACGCC GAAATCCAAA TTGGCGGCAA   2760
TATCTCACAA AAAGAAGGCA ATCTCACAAT TTCTTCTGAT AAAGTAAATA TTACCAATCA   2820
GATAACAATC AAAGCAGGCG TTGAAGGGGG GCGTTCTGAT TCAAGTGAGG CAGAAAATGC   2880
```

-continued

| | | | | | | |
|---|---|---|---|---|---|---|
| TAACCTAACT | ATTCAAACCA | AAGAGTTAAA | ATTGGCAGGA | GACCTAAATA | TTTCAGGCTT | 2940 |
| TAATAAAGCA | GAAATTACAG | CTAAAAATGG | CAGTGATTTA | ACTATTGGCA | ATGCTAGCGG | 3000 |
| TGGTAATGCT | GATGCTAAAA | AAGTGACTTT | TGACAAGGTT | AAAGATTCAA | AAATCTCGAC | 3060 |
| TGACGGTCAC | AATGTAACAC | TAAATAGCGA | AGTGAAAACG | TCTAATGGTA | GTAGCAATGC | 3120 |
| TGGTAATGAT | AACAGCACCG | GTTTAACCAT | TTCCGCAAAA | GATGTAACGG | TAAACAATAA | 3180 |
| CGTTACCTCC | CACAAGACAA | TAAATATCTC | TGCCGCAGCA | GGAAATGTAA | CAACCAAAGA | 3240 |
| AGGCACAACT | ATCAATGCAA | CCACAGGCAG | CGTGGAAGTA | ACTGCTCAAA | ATGGTACAAT | 3300 |
| TAAAGGCAAC | ATTACCTCGC | AAAATGTAAC | AGTGACAGCA | ACAGAAAATC | TTGTTACCAC | 3360 |
| AGAGAATGCT | GTCATTAATG | CAACCAGCGG | CACAGTAAAC | ATTAGTACAA | AAACAGGGGA | 3420 |
| TATTAAAGGT | GGAATTGAAT | CAACTTCCGG | TAATGTAAAT | ATTACAGCGA | GCGGCAATAC | 3480 |
| ACTTAAGGTA | AGTAATATCA | CTGGTCAAGA | TGTAACAGTA | ACAGCGGATG | CAGGAGCCTT | 3540 |
| GACAACTACA | GCAGGCTCAA | CCATTAGTGC | GACAACAGGC | AATGCAAATA | TTACAACCAA | 3600 |
| AACAGGTGAT | ATCAACGGTA | AAGTTGAATC | CAGCTCCGGC | TCTGTAACAC | TTGTTGCAAC | 3660 |
| TGGAGCAACT | CTTGCTGTAG | GTAATATTTC | AGGTAACACT | GTTACTATTA | CTGCGGATAG | 3720 |
| CGGTAAATTA | ACCTCCACAG | TAGGTTCTAC | AATTAATGGG | ACTAATAGTG | TAACCACCTC | 3780 |
| AAGCCAATCA | GGCGATATTG | AAGGTACAAT | TTCTGGTAAT | ACAGTAAATG | TTACAGCAAG | 3840 |
| CACTGGTGAT | TTAACTATTG | GAAATAGTGC | AAAAGTTGAA | GCGAAAAATG | GAGCTGCAAC | 3900 |
| CTTAACTGCT | GAATCAGGCA | AATTAACCAC | CCAAACAGGC | TCTAGCATTA | CCTCAAGCAA | 3960 |
| TGGTCAGACA | ACTCTTACAG | CCAAGGATAG | CAGTATCGCA | GGAAACATTA | ATGCTGCTAA | 4020 |
| TGTGACGTTA | AATACCACAG | GCACTTTAAC | TACTACAGGG | GATTCAAAGA | TTAACGCAAC | 4080 |
| CAGTGGTACC | TTAACAATCA | ATGCAAAAGA | TGCCAAATTA | GATGGTGCTG | CATCAGGTGA | 4140 |
| CCGCACAGTA | GTAAATGCAA | CTAACGCAAG | TGGCTCTGGT | AACGTGACTG | CGAAAACCTC | 4200 |
| AAGCAGCGTG | AATATCACCG | GGGATTTAAA | CACAATAAAT | GGGTTAAATA | TCATTTCGGA | 4260 |
| AAATGGTAGA | AACACTGTGC | GCTTAAGAGG | CAAGGAAATT | GATGTGAAAT | ATATCCAACC | 4320 |
| AGGTGTAGCA | AGCGTAGAAG | AGGTAATTGA | AGCGAAACGC | GTCCTTGAGA | AGGTAAAAGA | 4380 |
| TTTATCTGAT | GAAGAAAGAG | AAACACTAGC | CAAACTTGGT | GTAAGTGCTG | TACGTTTCGT | 4440 |
| TGAGCCAAAT | AATGCCATTA | CGGTTAATAC | ACAAAACGAG | TTTACAACCA | AACCATCAAG | 4500 |
| TCAAGTGACA | ATTTCTGAAG | GTAAGGCGTG | TTTCTCAAGT | GGTAATGGCG | CACGAGTATG | 4560 |
| TACCAATGTT | GCTGACGATG | GACAGCAGTA | GTCAGTAATT | GACAAGGTAG | ATTTCATCCT | 4620 |
| GCAATGAAGT | CATTTTATTT | TCGTATTATT | TACTGTGTGG | GTTAAAGTTC | AGTACGGGCT | 4680 |
| TTACCCACCT | TGTAAAAAAT | TA | | | | 4702 |